US012697360B2

(12) United States Patent
Lahusen et al.

(10) Patent No.: US 12,697,360 B2
(45) Date of Patent: Aug. 4, 2026

(54) VIRAL VECTORS FOR TREATING PARKINSON'S DISEASE

(71) Applicant: American Gene Technologies International Inc., Rockville, MD (US)

(72) Inventors: Tyler Lahusen, Rockville, MD (US); Charles David Pauza, Rockville, MD (US)

(73) Assignee: American Gene Technologies International Inc., Rockville, MD (US)

( * ) Notice: Subject to any disclaimer, the term of this patent is extended or adjusted under 35 U.S.C. 154(b) by 603 days.

(21) Appl. No.: 18/097,096

(22) Filed: Jan. 13, 2023

(65) Prior Publication Data

US 2023/0285480 A1 Sep. 14, 2023

Related U.S. Application Data

(62) Division of application No. 16/318,345, filed as application No. PCT/US2017/043157 on Jul. 20, 2017, now Pat. No. 11,583,562.

(60) Provisional application No. 62/365,316, filed on Jul. 21, 2016.

(51) Int. Cl.
| | |
|---|---|
| *A61K 35/76* | (2015.01) |
| *A61K 31/7105* | (2006.01) |
| *A61K 45/06* | (2006.01) |
| *C12N 9/10* | (2006.01) |
| *C12N 15/113* | (2010.01) |
| *C12N 15/86* | (2006.01) |

(52) U.S. Cl.
CPC .......... *A61K 35/76* (2013.01); *A61K 31/7105* (2013.01); *C12N 9/1077* (2013.01); *C12N 15/1137* (2013.01); *C12N 15/86* (2013.01); *A61K 45/06* (2013.01); *C12N 2310/14* (2013.01); *C12N 2310/531* (2013.01); *C12N 2320/32* (2013.01); *C12N 2330/51* (2013.01); *C12N 2740/16043* (2013.01); *C12Y 204/0203* (2013.01)

(58) Field of Classification Search
None
See application file for complete search history.

(56) References Cited

U.S. PATENT DOCUMENTS

| | | | |
|---|---|---|---|
| 5,654,195 | A | 8/1997 | Sodroski et al. |
| 5,668,255 | A | 9/1997 | Murphy |
| 5,674,703 | A | 10/1997 | Woo et al. |
| 6,156,514 | A | 12/2000 | Acevedo et al. |
| 6,399,383 | B1 | 6/2002 | Apt et al. |
| 6,635,472 | B1 | 10/2003 | Lauermann |
| 7,371,542 | B2 | 5/2008 | Ivanova et al. |
| 8,124,752 | B2 | 2/2012 | Bumcrot et al. |
| 8,287,857 | B2 | 10/2012 | Dudley et al. |
| 8,993,532 | B2 | 3/2015 | Hannon et al. |
| 9,522,176 | B2 | 12/2016 | DeRosa et al. |
| 9,527,904 | B2 | 12/2016 | Balazs et al. |
| 9,834,790 | B1 | 12/2017 | Pauza et al. |
| 9,834,791 | B2 | 12/2017 | Zhang et al. |
| 10,023,880 | B2 | 7/2018 | Pauza et al. |
| 10,036,038 | B2 | 7/2018 | Pauza et al. |
| 10,036,040 | B2 | 7/2018 | Pauza et al. |
| 10,137,144 | B2 | 11/2018 | Pauza et al. |
| 10,208,295 | B2 | 2/2019 | DeRosa et al. |
| 10,233,464 | B2 | 3/2019 | Pauza et al. |
| 2002/0168345 | A1 | 11/2002 | Dong |
| 2003/0013196 | A1 | 1/2003 | Engelman et al. |
| 2003/0096787 | A1 | 5/2003 | Perricaudet et al. |
| 2003/0119770 | A1 | 6/2003 | Lai et al. |
| 2003/0138444 | A1 | 7/2003 | Zavitz et al. |
| 2004/0142416 | A1 | 7/2004 | Laipis et al. |
| 2004/0161412 | A1 | 8/2004 | Penn et al. |
| 2004/0192629 | A1 | 9/2004 | Xu et al. |
| 2004/0214158 | A1 | 10/2004 | Sethi et al. |
| 2004/0248296 | A1 | 12/2004 | Beresford et al. |
| 2005/0019927 | A1 | 1/2005 | Hildinger et al. |
| 2005/0138677 | A1 | 6/2005 | Pfister et al. |
| 2006/0057553 | A1 | 3/2006 | Aguilar-Cordova |
| 2006/0183230 | A1 | 8/2006 | Silla et al. |
| 2006/0246520 | A1 | 11/2006 | Champagne et al. |
| 2007/0026521 | A1 | 2/2007 | Colosi |
| 2007/0141679 | A1 | 6/2007 | Sodroski et al. |
| 2007/0203333 | A1 | 8/2007 | McSwiggen et al. |

(Continued)

FOREIGN PATENT DOCUMENTS

| | | |
|---|---|---|
| BR | 2515 | 3/2019 |
| CN | 101516365 A | 8/2009 |

(Continued)

OTHER PUBLICATIONS

Meng, X.W. et al. 2014. Poly(ADP-ribose) polymerase inhibitors sensitize cancer cells to death receptor-mediated apoptosis by enhancing death receptor expression Journal of Biological Chemistry 289(30): 20543-20558; specif. pp. 20544, 20546, 20553 (Year: 2014).*

Hofig, I. et al. 2014. Systematic improvement of lentivirus transduction protocols by antibody fragments fused to VSV-G as envelope glycoprotein. Biomaterials 35: 4204-4212; specif. p. 4205 (Year: 2014).*

Yuan, K. et al. 2013. PARP-1 regulates resistance of pancreatic cancer to TRAIL therapy. Clinical Cancer Research 19(17): 4750-4759; specif. p. 4751 (Year: 2013).*

(Continued)

*Primary Examiner* — Louise W Humphrey
*Assistant Examiner* — Sharon M. Papciak
(74) *Attorney, Agent, or Firm* — COOLEY LLP

(57) ABSTRACT

A lentiviral vector system for expressing a lentiviral particle is disclosed. The lentiviral vector system includes a therapeutic vector, an envelope plasmid, and at least one helper plasmid. The lentiviral vector system can produce a lentiviral particle for inhibiting PARP expression in neuron cells of a subject afflicted with Parkinson's disease.

15 Claims, 8 Drawing Sheets

Specification includes a Sequence Listing.

(56) References Cited

U.S. PATENT DOCUMENTS

| 2008/0003225 A1 | 1/2008 | Vie et al. |
| 2008/0003682 A1 | 1/2008 | Lois-Caballe et al. |
| 2008/0039413 A1 | 2/2008 | Morris et al. |
| 2008/0131940 A1 | 6/2008 | Chiu et al. |
| 2008/0153737 A1 | 6/2008 | Lieberman et al. |
| 2008/0199961 A1 | 8/2008 | Rasko et al. |
| 2008/0227736 A1 | 9/2008 | Chen et al. |
| 2008/0293142 A1 | 11/2008 | Liu et al. |
| 2009/0148936 A1 | 6/2009 | Stout et al. |
| 2009/0304688 A1 | 12/2009 | Fournie et al. |
| 2010/0017911 A1 | 1/2010 | Dawson et al. |
| 2010/0069372 A1 | 3/2010 | Kazantsev |
| 2010/0119511 A1 | 5/2010 | Wang et al. |
| 2010/0120155 A1 | 5/2010 | Brennan et al. |
| 2010/0286166 A1 | 11/2010 | Pey Rodríguez et al. |
| 2010/0316676 A1 | 12/2010 | Sanders et al. |
| 2011/0008803 A1 | 1/2011 | Stockwell |
| 2011/0177155 A1 | 7/2011 | Peer et al. |
| 2011/0207226 A1 | 8/2011 | Ni et al. |
| 2012/0027725 A1 | 2/2012 | Galvin et al. |
| 2012/0034197 A1 | 2/2012 | Young |
| 2012/0053223 A1 | 3/2012 | Benkirane et al. |
| 2012/0114607 A1 | 5/2012 | Lai et al. |
| 2012/0201794 A1 | 8/2012 | Chen et al. |
| 2013/0078276 A1 | 3/2013 | Robinson et al. |
| 2013/0090371 A1 | 4/2013 | Lu |
| 2013/0122380 A1 | 5/2013 | Visco et al. |
| 2013/0142766 A1 | 6/2013 | Dodo et al. |
| 2013/0211380 A1 | 8/2013 | Cabrera Aquino et al. |
| 2014/0155468 A1 | 6/2014 | Gregory et al. |
| 2014/0162894 A1 | 6/2014 | Hatchwell et al. |
| 2014/0178340 A1 | 6/2014 | Robbins et al. |
| 2014/0234958 A1 | 8/2014 | Kasahara et al. |
| 2014/0248277 A1 | 9/2014 | Hoffman et al. |
| 2014/0336245 A1 | 11/2014 | Mingozzi et al. |
| 2015/0010578 A1 | 1/2015 | Balazs et al. |
| 2015/0018539 A1 | 1/2015 | Fellmann |
| 2015/0126580 A1 | 5/2015 | DePinho et al. |
| 2015/0132255 A1 | 5/2015 | Sorensen et al. |
| 2015/0176006 A1 | 6/2015 | Krause et al. |
| 2016/0060707 A1 | 3/2016 | Goldenberg et al. |
| 2016/0243169 A1 | 8/2016 | Chen et al. |
| 2016/0289681 A1 | 10/2016 | Ross et al. |
| 2017/0015976 A1 | 1/2017 | Nelson |
| 2017/0028036 A1 | 2/2017 | Mingozzi et al. |
| 2017/0037369 A1 | 2/2017 | Ramsborg et al. |
| 2017/0335344 A1 | 11/2017 | Pauza et al. |
| 2018/0010147 A1 | 1/2018 | Pauza et al. |
| 2018/0142257 A1 | 5/2018 | Pauza et al. |
| 2018/0142258 A1 | 5/2018 | Pauza et al. |
| 2018/0161455 A1 | 6/2018 | Pauza et al. |
| 2018/0177866 A1 | 6/2018 | Pauza |
| 2018/0195046 A1* | 7/2018 | Deng ..................... A61P 35/00 |
| 2018/0195050 A1 | 7/2018 | Szalay et al. |
| 2018/0256624 A1 | 9/2018 | Pauza et al. |
| 2018/0305716 A1 | 10/2018 | Pauza et al. |
| 2018/0355032 A1 | 12/2018 | Roberts et al. |
| 2019/0046633 A1 | 2/2019 | Pauza et al. |
| 2019/0062786 A1 | 2/2019 | Pauza et al. |
| 2019/0078096 A1 | 3/2019 | Lahusen et al. |
| 2019/0083523 A1 | 3/2019 | Pauza et al. |
| 2019/0388456 A1 | 12/2019 | Pauza et al. |
| 2020/0063161 A1 | 2/2020 | Pauza et al. |
| 2020/0087682 A1 | 3/2020 | Lahusen et al. |
| 2020/0109417 A1 | 4/2020 | Pauza et al. |
| 2020/0155590 A1 | 5/2020 | Lai et al. |
| 2020/0181645 A1 | 6/2020 | Pauza et al. |
| 2020/0318081 A1 | 10/2020 | Lahusen et al. |
| 2021/0047644 A1 | 2/2021 | Lahusen et al. |

FOREIGN PATENT DOCUMENTS

| CN | 101679466 A | 3/2010 |
| CN | 101805750 A | 8/2010 |
| CN | 103184224 A | 7/2013 |
| CN | 105112370 A | 12/2015 |
| CN | 108883100 A | 11/2018 |
| EP | 1647595 A1 | 4/2006 |
| EP | 3402483 A1 | 11/2018 |
| EP | 3413926 A1 | 12/2018 |
| EP | 3426777 A2 | 1/2019 |
| EP | 3468617 A1 | 4/2019 |
| EP | 3468618 A2 | 4/2019 |
| EP | 3481418 A1 | 5/2019 |
| EP | 3481435 A1 | 5/2019 |
| IN | 201947000153 | 2/2019 |
| JP | 2002506652 A | 3/2002 |
| JP | 2007527240 A | 9/2007 |
| JP | 2008518591 A | 6/2008 |
| JP | 2008538174 A | 10/2008 |
| JP | 2012508591 A | 4/2012 |
| JP | 2013530152 A | 7/2013 |
| JP | 2015518838 A | 7/2015 |
| JP | 2016502404 A | 1/2016 |
| WO | WO-9947691 A1 | 9/1999 |
| WO | WO-0220554 A2 | 3/2002 |
| WO | WO-03093436 A2 | 11/2003 |
| WO | WO-2004053137 A2 | 6/2004 |
| WO | WO-2005028634 A2 | 3/2005 |
| WO | WO-2005033282 A2 | 4/2005 |
| WO | WO-2006039721 A2 | 4/2006 |
| WO | WO-2006048215 A1 | 5/2006 |
| WO | WO-2007000668 A2 | 1/2007 |
| WO | WO-2007015122 A1 | 2/2007 |
| WO | WO-2007132292 A2 | 11/2007 |
| WO | WO-2007133674 A2 | 11/2007 |
| WO | WO-2008025025 A2 | 2/2008 |
| WO | WO-2008090185 A1 | 7/2008 |
| WO | WO-2009100928 A1 | 8/2009 |
| WO | WO-2009147445 A1 | 12/2009 |
| WO | WO-2010051521 A1 | 5/2010 |
| WO | WO-2010117974 A2 | 10/2010 |
| WO | WO-2010127166 A2 | 11/2010 |
| WO | WO-2011008348 A2 | 1/2011 |
| WO | WO-2011071476 A2 | 6/2011 |
| WO | WO-2011119942 A1 | 9/2011 |
| WO | WO-2012048303 A2 | 4/2012 |
| WO | WO-2012061075 A2 | 5/2012 |
| WO | WO-2012145624 A2 | 10/2012 |
| WO | WO-2013096455 A1 | 6/2013 |
| WO | WO-2014016817 A2 | 1/2014 |
| WO | WO-2014117050 A2 | 7/2014 |
| WO | WO-2014187881 A1 | 11/2014 |
| WO | WO-2015017755 A1 | 2/2015 |
| WO | WO-2015042308 A2 | 3/2015 |
| WO | WO-2015061491 A1 | 4/2015 |
| WO | WO-2015078999 A1 | 6/2015 |
| WO | WO-2015164759 A2 | 10/2015 |
| WO | WO-2016046234 A2 | 3/2016 |
| WO | WO-2016061232 A2 | 4/2016 |
| WO | WO-2016069716 A1 | 5/2016 |
| WO | WO-2016189159 A1 | 12/2016 |
| WO | WO-2016200997 A1 | 12/2016 |
| WO | WO-2017007994 A1 | 1/2017 |
| WO | WO-2017068077 A1 | 4/2017 |
| WO | WO-2017100551 A1 | 6/2017 |
| WO | WO-2017123918 A1 | 7/2017 |
| WO | WO-2017139065 A1 | 8/2017 |
| WO | WO-2017156311 A2 | 9/2017 |
| WO | WO-2017173453 A1 | 10/2017 |
| WO | WO-2017213697 A1 | 12/2017 |
| WO | WO-2017214327 A2 | 12/2017 |
| WO | WO-2018009246 A1 | 1/2018 |
| WO | WO-2018009847 A1 | 1/2018 |
| WO | WO-2018017882 A1 | 1/2018 |
| WO | WO-2018126112 A1 | 7/2018 |
| WO | WO-2018129540 A1 | 7/2018 |
| WO | WO-2018148443 A1 | 8/2018 |
| WO | WO-2018187231 A2 | 10/2018 |
| WO | WO-2018232359 A1 | 12/2018 |
| WO | WO-2019070674 A2 | 4/2019 |

(56)                References Cited

FOREIGN PATENT DOCUMENTS

WO    WO-2020097049 A1    5/2020
WO    WO-2020243717 A1    12/2020

OTHER PUBLICATIONS

Cookson, M.R. et al. 1999. Poly(ADP-ribose) polymerase is found in both the nucleus and cytoplasm of human CNS neurons. Brain Research 834: 182-185; specif. pp. 182, 184, 185 (Year: 1999).*
Jiao, S. et al. 1993. Long-term correction of rat model of Parkinson's disease in gene therapy. Nature 362: 450-453; specif. p. 450 (Year: 1993).*
Brumovsky, P.R. 2016. Dorsal root ganglion neurons and tyrosine hydroxylase—an intriguing association with implications for sensation and pain. Pain 157: 314-320; specif. p. 314 (Year: 2016).*
Sapru, M.K. et al. 2006. Silencing of human alpha-synuclein in vitro and in rat brain using lentiviral-mediated RNAi. Experimental Neurology 198: 382-390; specif. pp. 382, 387 (Year: 2006).*
JP; Office Action in the JP Application No. 2019-502170 dated May 28, 2021.
Non-Final Office Action for U.S. Appl. No. 16/318,345, mailed Nov. 18, 2020, 12 Pages.
Office Action for Japanese Patent Application No. 2022117082, mailed Jun. 27, 2023, 14 Pages.
Restriction Requirement for U.S. Appl. No. 16/318,345, mailed Jun. 26, 2020, 9 Pages.
Advisory Action for U.S. Appl. No. 13/333,882, mailed Nov. 16, 2018, 3 Pages.
Advisory Action for U.S. Appl. No. 15/736,284, mailed Jul. 23, 2019, 3 Pages.
Akinsheye I., et al., "Fetal Hemoglobin in Sickle Cell Anemia," Blood, Jul. 7, 2011, vol. 118, No. 1, pp. 19-27.
Altschul et al. "Basic Local Alignment Search Tool" 1990, J. Molecular Biology 215:403-410.
Altschul S.F., et al., "Gapped BLAST and PSI-BLAST: A New Generation of Protein Database Search Programs," Nucleic Acids Research, Jul. 1997, vol. 25, No. 17, pp. 3389-3402.
Anderson J.S., et al., "Preintegration HIV-1 Inhibition by a Combination Lentiviral Vector Containing a Chimeric TRIM5a Protein, a CCR5 shRNA, and TAR Decoy," Molecular Therapy, Dec. 2009, vol. 17, No. 12, pp. 2103-2114.
Ausubel F.M., et al., "Short Protocols in Molecular Biology: A Compendium of Methods from Current Protocols in Molecular Biology," Wiley, John & Sons, Inc., 1995, 1 Page.
Bartholome K., "Genetics and Biochemistry of the Phenylketonuria—Present State," Human Genetics, 1979, vol. 51, No. 03, pp. 241-245.
Benyamine A., et al., "BTN3A Molecules Considerably Improve Vy9V$\delta$2T Cells-based Immunotherapy in Acute Myeloid Leukemia," OncoImmunology, Oct. 2, 2016, vol. 5, No. 10, 10 Pages, (E1146843) *the whole document*.
Bergvall M., et al. "The E1 Proteins," Virology, 2013, vol. 445, pp. 35-56.
Blau N., et al., "Phenylketonuria," The Lancet, Oct. 23, 2010, vol. 376(9750), pp. 1417-1427.
Blick G., et al., "Cyclophosphamide Enhances SB-728-T Engraftment to Levels Associated with HIV-RNA Control," CROI Conference on Retroviruses and Opportunistic Infections, Mar. 3-6, 2014, 3 Pages.
Bourguigon P., et al., "Processing of Blood Samples Influences PBMC Viability and Outcome of Cell-mediated Immune Responses In Antiretroviral Therapy-naïve HIV-1-infected Patients," Journal of Immunological Methods, Dec. 1, 2014, vol. 414, pp. 1-10.
Brites C., et al., "Infection by HTLV-1 Is Associated with High Levels of Proinflammatory Cytokines in HIV-HCV-Coinfected Patients," Journal of Acquired Immune Deficiency Syndromes, Feb. 1, 2018, vol. 77, No. 2, pp. 230-234.
Briz V., et al., "Validation of Generation 4 Phosphorus-Containing Polycationic Dendrimer for Gene Delivery Against HIV-1," Current Medical Chemistry, 2012, vol. 19, No. 29, pp. 5044-5051.

Cannon J.R., et al., "Pseudotype-Dependent Lentiviral Transduction of Astrocytes or Neurons in the Rat Substantia Nigra," Experimental Neurology, Mar. 2011, vol. 228, No. 1, pp. 41-52.
Capietto A-H., et al., "Stimulated Y$\delta$ T Cells Increase the in Vivo Efficacy of Trastuzumab in HER-2+ Breast Cancer," Journal of Immunology, 2011, vol. 187(2), pp. 1031-1038.
Chandler R.J., et al., "Vector Design Influences Hepatic Genotoxicity After Adeno-Associated Virus Gene Therapy," Journal of Clinical Investigation, Feb. 2015, vol. 125, No. 2, pp. 870-880.
Charron C.E., et al., "Dominant-Negative Interference in the Pahenu2 Mouse Model of PKU: Effectiveness of Vectors Expressing Either Modified Forms of Phenylalanine Hydroxylase (PAH) or Ribozymes Plus a Hardened PAH mRNA," Molecular Therapy, 2005, vol. 11, pp. S163-S164.
Charron C.E., "Gene Therapy for Phenylketonuria: Dominant-Negative Interference in a Recessive Disease," Dissertation, University of Florida, 2005, 89 pages, [Retrieved on Jul. 26, 2018] Retrieved from URL: http://etd.fcla.edu/UF/UFE0011392/charron_c.pdf.
Chen Z., et al., "CD16+ Gammadelta T Cells Mediate Antibody Dependent Cellular Cytotoxicity: Potential Mechanism In The Pathogenesis of Multiple Sclerosis," Clinical Immunology, 2008, vol. 128(2), pp. 219-227.
Chiang C-M., et al., "Viral E1 and E2 Proteins Support Replication of Homologous and Heterologous Papillomaviral Origins," Proceedings of the National Academy of Sciences of the United States of America, Jul. 1, 1992, vol. 89, pp. 5799-5803.
Choi J-G., et al., "Multiplexing Seven miRNA-Based shRNAs to Suppress HIV Replication," Molecular Therapy : The Journal of the American Society of Gene Therapy, Feb. 2015, vol. 23, No. 02, pp. 310-320, DOI:10.1038/mt.2014.205, ISSN 1525-0016, XP055432740.
Christine, et al., Neurology, (20090000), vol. 73, No. 20, pp. 1662-1669.
Christophersen E.B., et al., "A Technique of Transumbilical Portal Vein Catheterization in Adults," The Archives of Surgery, 1967, vol. 95(6), pp. 960-963, (Abstract Only).
Clontech: "pLVX-shRNA1 Vector Information (PT4051-5 Catalog No. 632177, 2008)," Jul. 15, 2008, Retrieved from URL: http://www.takara.co.kr/file/ manual/pdf/PT4051-5.pdf.
Clontechniques: "High-Efficiency Lentiviral Packaging System," Jan. 2008, pp. 8-9, Retrieved from URL: https://catalog.takara-bio.co.jp/PDFFiles/200802_08.pdf.
Coligan, et al., "Short Protocols in Protein Science," Wiley, John & Sons, Inc, 2003.
Condiotti R., et al., "Prolonged Liver-Specific Transgene Expression by a Non-Primate Lentiviral Vector," Biochemical and Biophysical Research Communications, Jul. 30, 2004, vol. 320, No. 3, pp. 998-1006.
Corrected Notice of Allowance for U.S. Appl. No. 16/687,525, mailed Mar. 3, 2021, 2 Pages.
Couzi L., et al., "Antibody-Dependent Anti-Cytomegalovirus Activity of Human Gammadelta T Cells Expressing CD16 (FcgammaRIIIa)," Blood, 2012, vol. 119(6), pp. 1418-1427.
Craenenbroeck K.V., et al., "Episomal Vectors for Gene Expression in Mammalian Cells," European Journal Biochemistry, Jul. 14, 2000, vol. 267, pp. 5665-5678.
Cronin J., et al., "Altering The Tropism of Lentiviral Vectors Through Pseudotyping," Current Gene Therapy, Aug. 2005, vol. 5, No. 4, pp. 387-398.
Decision of Refusal for Japanese Patent Application No. 2019-502170, dated Mar. 28, 2022, 9 Pages. (with English translation).
Dickler H.B., et al., "Lymphocyte Binding of Aggregated IgG and Surface Ig Staining in Chronic Lymphocytic Leukaemia," Clinical and Experimental Immunology, 1973, vol. 14, No. 01, pp. 97-106.
Dieli F., et al., "Targeting Human γ$\delta$ T Cells with Zoledronate and Interleukin-2 for Immunotherapy of Hormone-Refractory Prostate Cancer," Europe PMC Funders Group, Cancer Research, Aug. 1, 2007, vol. 67, No. 15, pp. 7450-7457.
Ding Z., et al., "Administration-Route and Gender-Independent Longterm Therapeutic Correction of Phenylketonuria (PKU) in a Mouse Model by Recombinant Adeno-Associated Virus 8 Pseudotyped Vector-Mediated Gene Transfer," Gene Therapy, Dec. 1, 2005, vol. 13, pp. 587-593.

(56)         References Cited

OTHER PUBLICATIONS

Ding Z., et al., "Liver-Directed, AAV-and Lentivirus-Mediated Gene Therapy in the Phenylketonuria Mouse Model Pah-enu2," Molecular Therapy, May 2005, vol. 11, Supplement. 1, p. S348, XP055751452.

Donsante A., et al., "AAV Vector Integration Sites in Mouse Hepatocellular Carcinoma," Science, Jul. 27, 2007, vol. 317, No. 5837, p. 477.

Dorsey, E.R. et al., Neurology, (20070000), vol. 68, No. 5, pp. 384-386.

Douek D.C., et al., "HIV Preferentially Infects HIV-Specific CD4+ T Cells," Nature, May 2, 2002, vol. 417, No. 6884, pp. 95-98.

Eberling, et al., Neurology, (20080000), vol. 70, No. 21, pp. 1989-1993.

Eguchi K., et al., "Primary Sjogren's Syndrome with Antibodies to HTLV-I: Clinical and Laboratory Features," Annals of the Rheumatic Diseases, 1992, vol. 51, No. 6, pp. 769-776.

Eisensmith R.C., et al., "Multiple Origins for Phenylketonuria in Europe," American Journal of Human Genetics, 1992, vol. 51, No. 6, pp. 1355-1365.

Erdelyi K., et al., "Dual Role of Poly(ADP-ribose) Glycohydrolase in the Regulation of Cell Death in Oxidatively Stressed," FASEB Journal, 2009, vol. 23, No. 10, pp. 3553-3563, ISSN 0004521061.

Extended European Search Report for European Application No. 17750547.6, mailed Sep. 6, 2019, 6 Pages.

Extended European Search Report for European Application No. 17764128.9, mailed Aug. 12, 2019, 8 Pages.

Extended European Search Report for European Application No. 17810976.5, mailed Dec. 19, 2019, 8 Pages.

Extended European Search Report for European Application No. 17824652.6, mailed Feb. 6, 2020, 8 Pages.

Extended European Search Report for European Application No. 17825011.4, mailed Feb. 6, 2020, 8 Pages.

Extended European Search Report for European Application No. 17831904.2, mailed Mar. 11, 2020, 9 Pages.

Extended European Search Report for European Application No. 18736295.9, mailed Aug. 20, 2020, 12 Pages.

Extended European Search Report for European Application No. 18781288.8, mailed Dec. 8, 2020, 11 Pages.

Extended European Search Report for European Application No. 17739028.3, mailed Jun. 6, 2019, 8 Pages.

Extended European Search Report for European Application No. 16904834.5, mailed Dec. 19, 2019, 8 Pages.

Extended European Search Report for European Application No. 18817253.0, mailed Feb. 10, 2021, 8 Pages.

Extended European Search Report for European Application No. 16808223.8, mailed Dec. 13, 2018, 9 Pages.

Extended European Search Report for European Application No. 16822021.8, mailed Dec. 11, 2018, 8 Pages.

Fahn, S., Ann. N.Y. Acad. Sci., (20030000), vol. 991, pp. 1-14.

Final Office Action for U.S. Appl. No. 13/333,882, mailed Aug. 27, 2018, 11 Pages.

Final Office Action for U.S. Appl. No. 15/580,661, mailed Jun. 2, 2020, 16 Pages.

Final Office Action for U.S. Appl. No. 15/736,284, mailed May 2, 2019, 22 Pages.

Final Office Action for U.S. Appl. No. 16/076,655, mailed Jul. 27, 2020, 17 Pages.

Final Office Action for U.S. Appl. No. 16/132,247, mailed Jul. 1, 2019, 7 Pages.

Final Office Action for U.S. Appl. No. 16/182,443, mailed May 2, 2019, 07 Pages.

Final Office Action for U.S. Appl. No. 16/312,056, mailed Feb. 26, 2021, 22 Pages.

Final Office Action for U.S. Appl. No. 16/318,345, mailed Jun. 3, 2021, 13 Pages.

First Office Action in the CN Application No. 201780017712.6, mailed May 8, 2020, 10 Pages.

Fisher D.B., et al., "The Inhibition of Phenylalanine and Tyrosine Hydroxylases by High Oxygen Levels," Journal of Neurochemistry, May 1972, vol. 19, No. 5, pp. 1359-1365, (Abstract Only).

Fisher J.P.H., et al., "Effective Combination Treatment of GD2-Expressing Neuroblastoma and Ewing's Sarcoma Using Anti-GD2 ch14.18/CHO Antibody with Vγ9V52+ γT Cells," Oncolmmunology, 2016, vol. 5, Issue No. 1, e1025194, 32 Pages.

Fusetti F., et al., "Structure of Tetrameric Human Phenylalanine Hydroxylase and Its Implications for Phenylketonuria," Journal of Biological Chemistry, Jul. 3, 1998, vol. 273, No. 27, pp. 16962-16967, DOI: 10.1074/jbc.273.27.16962, XP055559179.

Futsch N., et al., "HTLV-1, the Other Pathogenic Yet Neglected Human Retrovirus: From Transmission to Therapeutic Treatment," Viruses, 2018, vol. 10, No. 01, 25 Pages.

GenBank Accession No. JG619773, "MNESC1NG-T3-001_L15_6FEB2009_054 Mnescing Cell Culture from Mahonia Nervosa Berberis Nervosa cDNA, mRNA Sequence," Feb. 13, 2014, 1 Page, Entire document, [Retrieved on Dec. 5, 2017], Retrieved from URL: https://www.ncbi.nlm.nih.gov/nucest/JG619773.

GenBank: "(long Control Region) [Human Papillomavirus, Type 16, Genomic, 860 nt]" GenBank Accession No. S60559, May 7, 1993, entire DNA sequence, pp. 1, [Located online Nov. 21, 2017] Retrieved from URL: https://ncbi.nlm.nih.gov/nuccore/S60559.

Gertner-Dardenne J., et al., "Bromohydrin Pyrophosphate Enhances Antibody-Dependent Cell-Mediated Cytotoxicity Induced by Therapeutic Antibodies," Blood, 2009, vol. 113(20), pp. 4875-4884.

Gessain A., et al., "Antibodies to Human T-Lymphotropic Virus Type-I in Patients with Tropical Spastic Paraparesis," The Lancet, Aug. 24, 1985, vol. 02, No. 8452, pp. 407-410.

Gessain A., et al., "Epidemiological Aspects and World Distribution of HTLV-1 Infection," Frontiers in Microbiology, Nov. 2012, vol. 03, Article 388, 23 Pages.

Gober H-J., et al., "Human T Cell Receptor γδ Cells Recognize Endogenous Mevalonate Metabolites in Tumor Cells," Journal of Experimental Medicine, Jan. 20, 2003, vol. 197, No. 2, pp. 163-168.

Goepfert P.A., et al., "Specificity and 6-Month Durability of Immune Responses Induced by DNA and Recombinant Modified Vaccinia Ankara Vaccines Expressing HIV-1 Virus-Like Particles," The Journal of Infectious Diseases, Jul. 1, 2014, vol. 210, pp. 99-110, XP055410056.

Goncalves D.U., et al., "Epidemiology, Treatment, and Prevention of Human T-Cell Leukemia Virus Type 1-Associated Diseases," Clinical Microbiology Reviews, Jul. 2010, vol. 23, No. 03, pp. 577-589.

Gorziglia M.I., et al., "Elimination of Both E1 and E2A from Adenovirus Vectors Further Improves Prospects for In Vivo Human gene Therapy," Journal of Virology, Jun. 1996, vol. 70, No. 6, pp. 4173-4178.

Grisch-Chan H.M., et al., "Low-Dose Gene Therapy for Murine PKU Using Episomal Naked DNA Vectors Expressing PAH from Its Endogenous Liver Promoter," Molecular Therapy Nucleic Acids, 2017, vol. 7, pp. 339-349.

Guldberg P., et al., "Aberrant Phenylalanine Metabolismin Phenylketonuria Heterozygotes," Journal of Inherited Metabolic Disease, 1998, vol. 21, No. 4, pp. 365-372.

Hafid A.Z., et al., "Phenylketonuria: A Review of Current and Future Treatments," Translational Pediatrics, 2015, vol. 4, No. 4 pp. 304-317.

Harlow E., et al., "Antibodies: A Laboratory Manual," Cold Spring Harbor Laboratory Press, 1988, 1 Page.

Harly C., et al., "Key Implication of CD277/butyrophilin-3 (BTN3A) in Cellular Stress Sensing by a Major Human T-cell Subset," Blood, Sep. 13, 2012, vol. 120, No. 11, pp. 2269-2279, DOI:10.1182/blood-2012-05-430470, ISSN 00064971, XP055081172.

Hassan G., et al., "Isolation of Umbilical Cord Mesenchymal Stem Cells Using Human Blood Derivative Accompanied With Explant Method," Stem Cell Investigation, 2019, pp. 1-8.

Hellstrom M., et al., "Cellular Tropism and Transduction Properties of Seven Adeno-Associated Viral Vector Serotypes in Adult Retina After Intravitreal Injection," Gene Therapy, 2009, vol. 16, pp. 521-532.

Huang Q., et al., "An Efficient Protocol to Generate Placental Chorionic Plate-derived Mesenchymal Stem Cells with Superior

(56) References Cited

OTHER PUBLICATIONS

Proliferative and Immunomodulatory Properties," Stem Cell Research & Therapy, 2019, vol. 10(301), pp. 1-15.

Hui Y., et al., "Construction of PARP-1 Gene Silencing Cell Lines by Lentiviral-Mediated RNA Interference Technology," Journal of Environmental Health, Apr. 2014, vol. 31, pp. 288-291, English abstract only.

International Preliminary Report on Patentability for International Application No. PCT/US2018/012998, mailed Jul. 18, 2019, 9 Pages.

International Preliminary Report on Patentability for International Application No. PCT/US2018/025733, mailed Oct. 17, 2019, 9 Pages.

International Search Report and Written Opinion for International Application No. PCT/US2019/024410, mailed Jul. 22, 2019, 10 Pages.

International Search Report and Written Opinion for International Application No. PCT/US2019/059828, mailed Feb. 14, 2020, 12 Pages.

International Preliminary Report on Patentability for International Application No. PCT/US2017/043157, mailed Jan. 31, 2019, 12 Pages.

International Search Report for International Application No. PCT/US2016/036519, mailed Nov. 7, 2016, 4 Pages.

International Search Report for International Application No. PCT/US2016/041456, mailed Oct. 19, 2016, 4 Pages.

International Search Report for International Application No. PCT/US2016/066185, mailed Jun. 9, 2017, 12 Pages.

International Search Report for International Application No. PCT/US2017/013019, mailed Jul. 17, 2017, 5 Pages.

International Search Report for International Application No. PCT/US2017/013024, mailed Jul. 14, 2017, 3 Pages.

International Search Report for International Application No. PCT/US2017/013399, mailed May 26, 2017, 4 Pages.

International Search Report for International Application No. PCT/US2017/021639, mailed Aug. 25, 2017, 5 Pages.

International Search Report for International Application No. PCT/US2017/036433, mailed Dec. 15, 2017, 5 Pages.

International Search Report for International Application No. PCT/US2017/041168, mailed Nov. 8, 2017, 4 Pages.

International Search Report for International Application No. PCT/US2017/043157, mailed Dec. 26, 2017, 7 Pages.

International Search Report for International Application No. PCT/US2018/012998, mailed May 29, 2018, 4 Pages.

International Search Report for International Application No. PCT/US2018/025733, mailed Sep. 24, 2018, 6 Pages.

International Search Report for International Application No. PCT/US2018/037924, mailed Nov. 9, 2018, 7 Pages.

International Search Report for International Application No. PCT/US2018/053919, mailed Apr. 12, 2019, 6 Pages.

Invitation to Pay Additional Fees and, Where Applicable, Protest Fee for International Application No. PCT/US2018/025733, mailed Jul. 17, 2018, 2 Pages.

Invitation to Pay Additional Fees and, where Applicable, Protest Fee for International Application No. PCT/US2018/037924, mailed Sep. 11, 2018, 3 Pages.

Invitation to Pay Additional Fees and, Where Applicable, Protest Fee for International Application No. PCT/US2018/053919, mailed Feb. 22, 2019, 3 Pages.

Jaalouk D.E., et al., "A Self-inactivating Retrovector Incorporating The IL-2 Promoter for Activation-Induced Transgene Expression Engineered T-cells," Virology, 2006, vol. 3, No. 97, 12 Pages.

Jakobsson J., et al., "Lentiviral Vectors for Use in the Central Nervous System," Molecular Therapy: The Journal of the American Society of Gene Therapy, Cell Press, US, Mar. 1, 2006, vol. 13, No. 3, pp. 484-493, DOI: 10.1016/J.YMTHE.2005.11.012, ISSN: 1525-0016, XP005326761.

Jiang X., et al., "A Novel EST-derived RNAi Screen Reveals a Critical Role for Farnesyl Diphosphate Synthase in Beta 2-adrenergic Receptor Internalization and Down-regulation," The FASEB Journal, Published Online on Jan. 27, 2012, vol. 26(5), pp. 1995-2007.

Kaalund S.S., et al., "Untreated Patients Dying With AIDS have Loss of Neocortical Neurons and Glia Cells," Frontiers in Neuroscience, vol. 13, Article. 1398, Jan. 2020, 10 Pages.

Kagdi H., et al., "Switching and Loss of Cellular Cytokine Producing Capacity Characterize In Vivo Viral Infection and Malignant Transformation In Human T-lymphotropic Virus Type 1 Infection," PLoS Pathogens, Feb. 14, 2018, vol. 14, No. 2, 25 Pages, e1006861.

Kagdi H.H., et al., "Risk Stratification of Adult T-Cell Leukemia/Lymphoma Using Immunophenotyping," Cancer Medicine, 2017, vol. 06, No. 01, pp. 298-309.

Kam T-I., et al., "Poly (ADP-ribose) Derived Pathologic [alpha]—Synuclein Neurodegeneration in Parkinson's disease," Science, US, Nov. 2, 2018, vol. 362, No. 6414, eaat8407, 12 pages, ISSN: 00368075, DOI: 10.1126/science.aat8407, XP55672116.

Kaplitt, et al., Lancet Neurol, (20070000), vol. 369, No. 9579, pp. 2097-2105.

Kaufman S., "A Model of Human Phenylalanine Metabolism in Normal Subjects and in Phenylketonuric Patients," Proceedings of the National Academy of Sciences, USA, Mar. 1999, vol. 96(6), pp. 3160-3164.

Kaufman S., et al., "Phenylalanine Hydroxylase Activity in Liver Biopsies from Hyperphenylalaninemia Heterozygotes: Deviation from Proportionality with Gene Dosage," Pediatric Research, 1975, vol. 9(8), pp. 632-634.

Kavanagh D.G., et al., "Expansion of HIV-specific CD4+ and CD8+ T Cells by Dendritic Cells Transfected with mRNA Encoding Cytoplasm- or lysosome-targeted Nef," Blood, American Society of Hematology, US, Mar. 2006, Oct. 25, 2005, vol. 107, No. 5, pp. 1963-1969, DOI: 10.1182/BLOOD-2005-04-1513, ISSN 0006-4971, XP008141565.

Kim H.Y., et al., "Farnesyl Diphosphate Synthase Is Important for The Maintenance of Glioblastoma Stemness," Experimental & Molecular Medicine, Published Online on Oct. 17, 2018, vol. 50, No. 10, 12 pages, DOI: 10.1038/s12276-018-0166-2, XP055605154.

Kopinmarkey, Annu. Rev. Neurosci, (19880000), vol. 11, pp. 81-96.

Krajinovic M., et al., "Sequencing Data on The Long Control Region of Human Papillomavirus Type 16," Journal of General Virology, 1991, vol. 72, pp. 2573-2576.

Lam S., et al., "T-cell Therapies for HIV," Immunotherapy, Future Medicine, London, Apr. 1, 2013, vol. 5, No. 4, pp. 407-414, DOI: 10.2217/IMT.13.23, ISSN 1750-7448, XP009182920.

Ledley F.D., et al., "Molecular Biology of Phenylalanine Hydroxylase and Phenylketonuria," Trends in Genetics, Elsevier Science Publishers, B.V. Amsterdam, NL, Nov. 1985, vol. 1, pp. 309-313, DOI: 10.1016/0168-9525(85)90121-0, ISSN 0168-9525, XP025943064.

Ledley F.D., et al., "Retroviral-Mediated Gene Transfer of Human Phenylalanine Hydroxylase Into Nih-3t3 and Hepatoma Cells," Proceedings of The National Academy of Sciences, National Academy of Sciences, Jan. 1986, vol. 83, No. 2, pp. 409-413.

Lee S-K., et al., "Lentiviral Delivery of Short Hairpin RNAs Protects CD4 Cells from Multiple Clades and Primary Isolates of HIV," Blood, Aug. 1, 2005, vol. 106, No. 3, pp. 818-826.

Lee Y., et al., "Poly (ADP-ribose) in the Pathogenesis of Parkinson's Disease," BMB Reports, Korean Society for Biochemistry and Molecular Biology, KR, Aug. 31, 2014, vol. 47, No. 8, pp. 424-432.

Li J., et al., "Reduced Expression of the Mevalonate Pathway Enzyme Farnesyl Pyrophosphate Synthase Unveils Recognition of Tumor Cells by V[gamma]9V[delta]2 T Cells," The Journal of Immunology, US, (20090603), Jun. 2009, vol. 182, No. 12, pp. 8118-8124.

Li Z., et al., "Inhibition Of Farnesyl Pyrophosphate Synthase Prevents Angiotensin II-induced Cardiac Fibrosis In Vitro," Clinical & Experimental Immunology, 2014, vol. 176, pp. 429-437.

Lin Y., et al., "Up-Regulation of Bcl-2 is Required for the Progression of Prostate Cancer Cells from an Androgen-Dependent to an Androgen-Independent Growth Stage," Cell Research, Apr. 3, 2007, vol. 17, pp. 531-536.

Liu F., et al., Effects of Poly (ADP-ribose) Polymerase-1 (PARP-1) Inhibition on Sulfur Mustard-Induced Cutaneous Injuries in Vitro and in Vivo, PeerJ, 2016, vol. 4, e1890, 30 Pages.

(56)        References Cited

OTHER PUBLICATIONS

Longo N., et al., "Single-Dose, Subcutaneous Recombinant Phenylalanine Ammonia Lyase Conjugated with Polyethylene Glycol in Adult Patients with Phenylketonuria: An Open-Label, Multicenter, Phase 1 Dose-Escalation Trial," The Lancet, Jul. 5, 2014, vol. 384(9937), pp. 37-44.

Lu R., et al., "Simian Virus 40-Based Replication of Catalytically Inactive Human Immunodeficiency Virus Type 1 Integrase Mutants in Nonpermissive T Cells and Monocyte-Derived Macrophages," Journal of Virology, Jan. 2004, pp. 658-668. DOI: 10.1128/JVI.78.2658-668.2004.

Lu X., et al., "Anti-sense-Mediated Inhibition of Human Immunodeficiency Virus (HIV) Replication by Use of an HIV Type 1-Based Vector Results in Severely Attenuated Mutants Incapable of Developing Resistance," Journal of Virology, Jul. 2004, vol. 79, No. 13, pp. 7079-7088.

MacNamara A., et al., "HLA Class I Binding of HBZ Determines Outcome in HTLV-1 Infection," PLoS Pathog, Sep. 2010, vol. 06, No. 09:e1001117, pp. 1-12.

Mandir A.S., et al., "Poly (ADP-ribose) Polymerase Activation Mediates 1-methyl-4-phenyl-1, 2,3,6-tetrahydropyridine (MPTP)-induced Parkinsonism," Proceedings of the National Academy of Sciences of the United States of America, May 11, 1999, vol. 96, No. 10, pp. 774-779.

Manel N., et al., "The Ubiquitous Glucose Transporter GLUT-1 is a Receptor for HTLV," Cell, Nov. 14, 2003, vol. 115, No. 04, pp. 449-459.

Marks Jr. et al., Lancet Neurol, (20100000), vol. 9, No. 12, pp. 1164-1172.

Martin K.A., et al., "Global Transcriptome Analysis Reveals That Poly (ADP-Ribose) Polymerase 1 Regulates Gene Expression through EZH2," Molecular and Cellular Biology, Dec. 2015, vol. 35, No. 23, 52 Pages.

Martinez M.P., et al., "Comparative Virology of HTLV-1 and HTLV-2," Retrovirology, Aug. 7, 2019, vol. 16, Article. 21, No. 1, 12 Pages.

Mason R.D., et al., "Inactivated Simian Immunodeficiency Virus-Pulsed Autologous Fresh Blood Cells as an Immunotherapy Strategy," Journal of Virology, Feb. 2009, vol. 83, No. 3, pp. 1501-1510.

McBride A.A, "The Papillomavirus E2 Proteins," Virology, Oct. 2013, vol. 445, No. 1-2, pp. 57-79.

Miettinen T.P., et al., "Mevalonate Pathway Regulates Cell Size Homeostasis and Proteostasis Through Autophagy," Cell Reports, Dec. 22, 2015, vol. 13(11), pp. 2610-2620.

Mochizuki M., et al., "HTLV-I Uveitis: A Distinct Clinical Entity Caused by HTLV-1," Japanese Journal of Cancer Research, Mar. 1992, vol. 83, No. 3, pp. 236-239.

Mochizuki S., et al., "Long-Term Correction of Hyperphenylalaninemia by AAV-Mediated Gene Transfer Leads to Behavioral Recovery in Phenylketonuria Mice," Gene Therapy, 2004, vol. 11 (13), pp. 1081-1086.

Moser B., et al., "y T Cells: Novel Initiators of Adaptive Immunity," Immunological Reviews, Feb. 2, 2007, vol. 215, pp. 89-102.

Mosley A.J., et al., "Cell-Mediated Immune Response to Human T-Lymphotropic Virus Type I," Viral Immunology, 2005, vol. 18, No. 2, pp. 293-305.

Munoz N.M., et al., "Ex Vivo Expansion and Lentiviral Transduction of Macaca Nemestrina CD4 + T Cells," Journal of Medical Primatology, Dec. 2009, vol. 38, No. 6, pp. 438-443.

Myers E.W., et al., "Optimal Alignments in Linear Space," Cabios, 1988, vol. 4, No. 1, pp. 11-17.

Nada M.H., et al., "Enhancing Adoptive Cancer Immunotherapy with Vγ2Vδ2 T Cells Through Pulse Zoledronate Stimulation," Journal for Immunotherapy of Cancer, Feb. 21, 2017, vol. 5, No. 1, pp. 1-23, DOI:10.1186/S40425-017-0209-6, XP021242440.

Nagai M., et al., "Human T-Cell Lymphotropic Virus Type I and Neurological Diseases," Journal of NeuroVirology, Apr. 2003, vol. 9, No. 2, pp. 228-235.

Nault J-C., et al., "Adeno-Associated Virus Type 2 as an Oncogenic Virus in Human Hepatocellular Carcinoma," Molecular & Cellular Oncology, 2016, vol. 3, No. 2, 4 Pages, e1095271.

NCBI: "Human Prothrombin Gene Liver-specific Enhancer," Nucleotide, Database Accession No. M65141.1, Apr. 27, 1993, 01 page, XP055613203, [Retrieved on Mar. 31, 2019] Retrieved from URL: https://www.ncbi.ntm.nih.gov/nuccore/M65141.1.

Needleman et al. "A General Method Applicable to the Search for Similarities in the Amino Acid Sequence of Two Proteins" Mar. 28, 1970, J. Molecular Biology 48(3):443-453.

Nie J., "DNA Repair Proteins Metnase and PARP1 Regulate DNA Integration," 2000-2019—CSU Theses and Dissertations[online] 2015, vol. Chapter 3, pp. 95-141, ISSN 0004521062.

Nishioka K., et al., "Chronic Inflammatory Arthropathy Associated With HTLV-1," The Lancet, Feb. 25, 1989, vol. 1, No. 8635, 1 Page.

Non-Final Office Action for U.S. Appl. No. 13/333,882, mailed Apr. 18, 2019, 11 Pages.

Non-Final Office Action for U.S. Appl. No. 13/333,882, mailed Feb. 22, 2018, 08 Pages.

Non-Final Office Action for U.S. Appl. No. 15/580,661, mailed Jan. 13, 2020, 11 Pages.

Non-Final Office Action for U.S. Appl. No. 15/580,661, mailed Feb. 19, 2021, 27 Pages.

Non-Final Office Action for U.S. Appl. No. 15/736,284, mailed Oct. 19, 2018, 26 Pages.

Non-Final Office Action for U.S. Appl. No. 15/736,284, mailed Oct. 29, 2020, 26 Pages.

Non-Final Office Action for U.S. Appl. No. 15/849,062, mailed Feb. 22, 2018, 05 Pages.

Non-Final Office Action for U.S. Appl. No. 15/850,937, mailed Feb. 22, 2018, 05 Pages.

Non-Final Office Action for U.S. Appl. No. 15/904,131, mailed Jun. 15, 2018, 07 Pages.

Non-Final Office Action for U.S. Appl. No. 16/008,991, mailed May 7, 2019, 07 Pages.

Non-Final Office Action for U.S. Appl. No. 16/011,550, mailed Sep. 17, 2018, 8 Pages.

Non-Final Office Action for U.S. Appl. No. 16/076,655, dated Feb. 21, 2020, 45 Pages.

Non-Final Office Action for U.S. Appl. No. 16/083,384, mailed Mar. 16, 2020, 9 Pages.

Non-Final Office Action for U.S. Appl. No. 16/132,247, mailed May 16, 2019, 06 Pages.

Non-Final Office Action for U.S. Appl. No. 16/182,443, mailed Dec. 31, 2018, 10 Pages.

Non-Final Office Action for U.S. Appl. No. 16/218,010, mailed May 24, 2019, 06 Pages.

Non-Final Office Action for U.S. Appl. No. 16/308,373, mailed Sep. 22, 2020, 32 Pages.

Non-Final Office Action for U.S. Appl. No. 16/312,056, mailed Jul. 6, 2020, 23 Pages.

Non-Final Office Action for U.S. Appl. No. 16/530,908, mailed Jun. 1, 2020, 6 Pages.

Non-Final Office Action for U.S. Appl. No. 16/563,738, mailed Mar. 12, 2021, 11 Pages.

Non-Final Office Action for U.S. Appl. No. 16/943,800, mailed Nov. 25, 2020, 08 Pages.

Notice of Allowance for U.S. Appl. No. 13/333,882, mailed Nov. 27, 2019, 3 Pages.

Notice of Allowance for U.S. Appl. No. 13/333,882, mailed Oct. 29, 2019, 8 Pages.

Notice of Allowance for U.S. Appl. No. 14/706,481, mailed Oct. 13, 2019, 05 Pages.

Notice of Allowance for U.S. Appl. No. 15/652,080, mailed Nov. 2, 2017, 05 Pages.

Notice of Allowance for U.S. Appl. No. 15/668,223, mailed Mar. 26, 2018, 07 Pages.

Notice of Allowance for U.S. Appl. No. 15/849,062, mailed Apr. 26, 2018, 05 Pages.

Notice of Allowance for U.S. Appl. No. 15/850,937, mailed Apr. 23, 2018, 05 Pages.

Notice of Allowance for U.S. Appl. No. 15/904,131, mailed Aug. 10, 2018, 05 Pages.

(56) References Cited

OTHER PUBLICATIONS

Notice of Allowance for U.S. Appl. No. 16/008,991, mailed Aug. 14, 2019, 5 Pages.

Notice of Allowance for U.S. Appl. No. 16/011,550, mailed Oct. 31, 2018, 5 Pages.

Notice of Allowance for U.S. Appl. No. 16/076,655 mailed Dec. 2, 2020, 3 Pages.

Notice of Allowance for U.S. Appl. No. 16/083,384, mailed May 18, 2020, 8 Pages.

Notice of Allowance for U.S. Appl. No. 16/132,247, mailed Jul. 19, 2019, 05 Pages.

Notice of Allowance for U.S. Appl. No. 16/182,443, mailed Jul. 3, 2019, 3 Pages.

Notice of Allowance for U.S. Appl. No. 16/182,443, mailed Jun. 18, 2019, 5 Pages.

Notice of Allowance for U.S. Appl. No. 16/218,010, mailed Sep. 25, 2019, 8 Pages.

Notice of Allowance for U.S. Appl. No. 16/530,908, mailed Jul. 10, 2020, 05 Pages.

Notice of Allowance for U.S. Appl. No. 16/593,882, dated Jan. 26, 2021, 8 Pages.

Notice of Allowance for U.S. Appl. No. 16/687,525, mailed Jan. 13, 2021, 8 Pages.

Notice of Allowance for U.S. Appl. No. 16/943,800, mailed Feb. 10, 2021, 7 Pages.

Notice of Final Rejection for Japanese Patent Application No. 2018-536892, dated Nov. 16, 2020, 8 Pages.

Notice of Reasons for Rejection for Japanese Patent Application No. 2018-547354, mailed Feb. 16, 2021, 22 Pages.

Nowacki P., et al., "The PAH Mutation Analysis Consortium Database: Update 1996," Nucleic Acids Research, Jan. 1, 1997, vol. 25, No. 1, pp. 139-142, DOI: 10.1093/nar/25.1.139, XP055707752.

Nucleotide: "Human Papillomavirus Type 16 (HPV16), Complete Genome," GenBank: K02718.1, Publication [online], Mar. 18, 1994, 4 Pages, Retrieved from URL: https://www.ncbi.nlm.nih.gov/nucleotide/333031?report=genbank&log$=nucltop&blast_rank=22&RID=H3E1THFU014.

Office Action for Chinese Application No. 202010396594.8, mailed Jan. 15, 2021, 12 Pages.

Office Action for Japanese Application No. 2017-564550, mailed Mar. 18, 2020, 12 Pages.

Office Action for Japanese Application No. 2017-567175, mailed Jun. 15, 2020, 7 Pages.

Office Action for Japanese Application No. 2018-536892, mailed Jun. 26, 2020, 07 Pages.

Office Action for Japanese Application No. 2018-563892 mailed Oct. 14, 2020, 11 Pages.

Office Action for Japanese Patent Application No. 2019-500475, mailed Jun. 12, 2020, 11 Pages.

Office Action in the EPO Application No. 16808223.8, mailed May 11, 2020, 5 Pages.

Office Action in the Japanese Application No. 2018-541270, mailed Jan. 8, 2021, 8 Pages.

Oh H-J., et al., "Reversal of Gene Expression Profile in the Phenylketonuria Mouse Model After Adeno-Associated Virus Vector-Mediated Gene Therapy," Molecular Genetics and Metabolism, 2005, vol. 86, Supplement. 1, pp. S124-S132.

Oh H-J., et al., "Long-Term Enzymatic and Phenotypic Correction in the Phenylketonuria Mouse Model by Adeno-Associated Virus Vector-Mediated Gene Transfer," Pediatric Research, 2004, vol. 56, No. 2, pp. 278-284.

Oh T., et al., "Lentiviral Vector Design Using Alternative RNA Export Elements," Retrovirology, Jun. 5, 2007, vol. 4:38, pp. 1-10.

Olsen A.L. et al., "PARP Inhibitors and Parkinson's Disease," Clinical Implications of Basic Research, Jan. 31, 2019, pp. 492-494, XP55672111, [Retrieved on Feb. 27, 2020], Retrieved from URL: https://mfprac.com/web2019/07literature/literature/Neurology/ParkinsonPARPI_Olsen.pdf, *the whole document*.

Osame M., et al., "HTLV-I Associated Myelopathy, A New Clinical Entity," The Lancet, May 3, 1986, vol. 1, No. 8488, pp. 1031-1032.

Ostertag D., et al., "Brain Tumor Eradication and Prolonged Survival from Intratumoral Conversion of 5-Fluorocytosine to 5-fluorouracil Using a Nonlytic Retroviral Replicating Vector," Neoro-Oncology, Feb. 2012, vol. 14(2), pp. 145-159.

Pallikkuth S., et al., "Human Immunodeficiency Virus (HIV) Gag Anti-Specific T-Helper and Granule-Dependent CD8 T-Cell Activities in Exposed but Uninfected Heterosexual Partners of HIV Type 1-Infected Individuals in North India," Clinical and Vaccine Immunology, Sep. 2007, vol. 14, No. 9, pp. 1196-1202.

Pan D., et al., "Biodistribution and Toxicity Studies of VSVG-Pseudotyped Lentiviral Vector After Intravenous Administration in Mice with the Observation of in Vivo Transduction of Bone Marrow," Molecular Therapy, Jul. 2002, vol. 6, No. 1, pp. 19-29.

PCT Application No. PCT/CN2016/094828, filed Aug. 12, 2016, 85 Pages.

Pearson et al. "Improved Tools for Biological Sequence Comparison" Apr. 1988, Proceedings of the National Academy of Sciences of the United States of America 85(8):2444-2448.

Poiesz B. J., et al., "Detection and Isolation of Type C Retrovirus Particles From Fresh and Cultured Lymphocytes of a Patient With Cutaneous T-cell Lymphoma," Proceedings of the National Academy of Sciences of the United States of America, Dec. 1980, vol. 77, No. 12, pp. 7415-7419.

Poiesz B.J., "T-cell Lines Established From Human T-lymphocytic Neoplasias by Direct Response to T-cell Growth Factor," Proceedings of the National Academy of Sciences of the United States of America, Nov. 1980, vol. 77, No. 11, pp. 6815-6819.

Poonia B., et al., "Gamma Delta T Cells From HIV+ Donors Can be Expanded In Vitro by Zoledronate/Interleukin-2 to Become Cytotoxic Effectors for Antibody-dependent Cellular Cytotoxicity," Cytotherapy, 2012, vol. 14, No. 2, pp. 173-181.

Porichis F., et al., "HIV-specific CD4 T Cells and Immune Control of Viral Replication," Current Opinion in HIV and AIDS, US, May 2011, vol. 6, No. 3, pp. 174-180.

Przedborski, et al., Proc. Natl. Acad. Sci. U.S.A., (19960000), vol. 93, pp. 44565-44571.

Quan J-J., et al., "Parp3 Interacts with FoxM1 to Confer Glioblastoma Cell Radio Resistance," Tumor Biology, Karger, BaseL CH, Published online on Jun. 4, 2015, vol. 36, No. 11, pp. 8617-8624, ISSN: 1010-4283, DOI: 10.1007/SI3277-015-3554-4, XP036217799.

Requirement for Restriction for U.S. Appl. No. 15/736,284, mailed Jul. 12, 2018, 9 Pages.

Restriction Requirement for U.S. Appl. No. 15/580,661, mailed Oct. 22, 2019, 14 Pages.

Restriction Requirement for U.S. Appl. No. 15/668,223, mailed Oct. 23, 2017, 06 Pages.

Restriction Requirement for U.S. Appl. No. 16/011,550, mailed Aug. 3, 2018, 06 Pages.

Restriction Requirement for U.S. Appl. No. 16/076,655, mailed Nov. 4, 2019, 8 Pages.

Restriction Requirement for U.S. Appl. No. 16/083,384, mailed Nov. 7, 2019, 8 Pages.

Restriction Requirement for U.S. Appl. No. 16/308,373, mailed Jun. 15, 2020, 16 Pages.

Restriction Requirement for U.S. Appl. No. 16/312,056, mailed Jan. 29, 2020, 7 Pages.

Restriction Requirement for U.S. Appl. No. 16/563,738, mailed Dec. 8, 2020, 6 Pages.

Restriction Requirement for U.S. Appl. No. 16/593,882, mailed Nov. 19, 2020, 06 Pages.

Roc L., et al., "Rapid Subacute Myelopathy Following Kidney Transplantation From Htlv-1 Donors: Role of Immunosuppresors and Failure of Antiretrovirals," Therapeutic Advances in Infectious Disease, Jan.-Dec. 2019, vol. 6, 11 Pages.

Rose R.D., et al., "Safety, Immunogenicity and Efficacy of Peptide-Pulsed Cellular Immunotherapy in Macaques," Journal of Medical Primatology, 2008, vol. 37(2), pp. 69-78.

Sambrook J., et al., "Molecular Cloning: A Laboratory Manual," 3rd edition, Cold Spring Harbor Laboratory Press, 2000, 2272 Pages.

Schiller C.B., et al., "CD19-Specific Triplebody SPM-1 Engages NK and y T Cells for Rapid and Efficient Lysis of Malignant B-Lymphoid Cells," Oncotarget, 2016, vol. 7(50), pp. 83392-83408.

(56)            References Cited

OTHER PUBLICATIONS

Schiller D.S., et al., "Parameters Influencing Measurement of the Gag Antigen-Specific T-Proliferative Response to HIV Type 1 Infection," AIDS Research and Human Retroviruses, US, 2000, vol. 16, No. 03, pp. 259-271, DOI:10.1089/088922200309359, ISSN 0889-2229, XP055617438.

Seedorf et al., "Human Papillomavirus Type 16 DNA Sequence," Virology, Aug. 1985, vol. 145, pp. 181-185.

Shedlovsky A., et al., "Mouse Models of Human Phenylketonuria," Genetics, Aug. 1993, vol. 134, No. 4, pp. 1205-1210.

Smith P.L., et al., "Developments in HIV-1 Immunotherapy and Therapeutic Vaccination," F1000Prime Reports, Jun. 2, 2014, vol. 06, No. 43, 12 Pages.

Soker S., et al., "Neuropilin-1 is Expressed by Endothelial and Tumor Cells as an Isoform-Specific Receptor for Vascular Endothelial Growth Factor," Cell, Mar. 20, 1998, vol. 92, No. 06, pp. 735-745.

Spartevello F., et al., "Development of Lentiviral Vectors Simultaneously Expressing Multiple siRNAs Against CCR5, vif and tat/rev Genes for an HIV-1 Gene Therapy Approach," Molecular Therapy—Nucleic Acids, Apr. 19, 2016, vol. 5, pp. 1-12.

Stunkel W., et al., "The Chromatin Structure of the Long Control Region of Human Papillomavirus Type 16 Represses Viral Oncoprotein Expression," Journal of Virology, Mar. 1999, vol. 73, No. 3, pp. 1918-1930.

Sverdrup FM., et al., "Development of Human Papillomavirus Plasmids Capable of Episomal Replication in Human Cell Lines," Gene Therapy, Mar. 26, 1999, pp. 1317-1321, Retrieved from URL: http://www.stockton-pressco.uk/gt.

Tebas P., et al., "Antiviral Effects of Autologous CD4 T Cells Genetically Modified With a Conditionally Replicating Lentiviral Vector Expressing Long Antisense to HIV," Pre published on Dec. 20, 2012, Blood, Feb. 28, 2013, vol. 121, No. 9, pp. 1524-1533, XP055345565.

Thompson K., et al., "Alkylamines Cause Vγ9Vδ2 T-cell Activation and Proliferation by Inhibiting the Mevalonate Pathway," Blood, Jan. 15, 2006, vol. 107, No. 2, pp. 651-654.

Tokuyama H., et al., "Vy9Vδ2 T Cell Cytotoxicity Against Tumor Cells is Enhanced by Monoclonal Antibody Drugs—Rituximab and Trastuzumab," International Journal of Cancer, 2008, vol. 122 (11), pp. 2526-2534.

Tolmachov O.E., et al., "Designing Lentiviral Gene Vectors," Viral Gene Therapy, Jul. 20, 2011, Chapter. 13, 23 Pages, ISBN: 978-953-307-539-6, Retrieved from URL: http://www.intechopen.com/books/viral-gene-therapy/designing-lentiviral-gene-vectors.

Twitty C.G., et al., "Retroviral Replicating Vectors Deliver Cytosine Deaminase Leading to Targeted 5-Fluorouracil-Mediated Cytotoxicity in Multiple Human Cancer Types," Human Gene Therapy Methods, Feb. 1, 2016, vol. 27, No. 1, pp. 17-31.

Uchiyama T., et al., "Adult T-Cell Leukemia: Clinical and Hematologic Features of 16 Cases," Blood, Sep. 1977, vol. 50, No. 03, pp. 481-492.

Vargas J., Jr., et al., "Novel Integrase-defective Lentiviral Episomal Vectors for Gene Transfer", Human Gene Therapy, Liebert, US, Apr. 2004, vol. 15, No. 4, pp. 361-372, DOI: 10.1089/104303404322959515, ISSN 1043-0342, XP001205920.

Vargas Jr J., et al., "Conditionally Replicating Lentiviral-Hybrid Episomal Vectors for Suicide Gene Therapy," Antiviral Research, Elsevier BV, NL, Dec. 1, 2008, Jul. 21, 2008, vol. 80, No. 3, pp. 288-294, DOI: 10.1016/J.ANTIVIRAL.2008.06.015, ISSN 0166-3542, XP025684743.

Wang H., et al., "Butyrophilin 3A1 Plays an Essential Role In Prenyl Pyrophosphate Stimulation of Human Vγ2Vδ2 T cell," The Journal of Immunology, 2013, vol. 191, No. 3, pp. 1029-1042, DOI:10.4049/jimmunol.1300658, ISSN 0004789817, XP055557660.

Wang H., et al., "Indirect Stimulation of Human Vy2Vδ2 T Cells through Alterations in Isoprenoid Metabolism," Journal of Immunology, 2011, vol. 187, pp. 5099-5113.

Wang H-B., et al., "HIV Vaccine Research: The Challenge and the Way Forward," Journal of Immunology Research, 2015, vol. 2015, Article. 503978, 5 pages.

Wang Y., et al., "Intravenous Delivery of SIRNA Targeting CD47 Effectively Inhibits Melanoma TumorGrmYth and Lung Metastasis," Molecular Therapy, Oct. 2013, vol. 21, No. 10, pp. 1919-1929.

Weintraub, D. et al., Am. J. Manag. Care, (20080000), vol. 14, pp. S40-S48.

Wendelburg B.J., et al., "An Enhanced EBNA1 Variant With Reduced IR3 Domain for Long-term Episomal Maintenance and Transgene Expression of Orip-based Plasmids in Human Cells," Gene Therapy, Nature Publishing Group, GB, Oct. 6, 1998, vol. 5, pp. 1389-1399.

Westerhout E.M., et al., "A Conditionally Replicating HIV-based Vector That Stably Expresses an Antiviral shRNA Against HIV-1 Replication," Molecular Therapy, The Journal of the American Society of Gene Therapy, Academic Press, Nature Publishing Group, US, May 11, 2006, vol. 14, No. 2, pp. 268-275, DOI:10.1016/J.YMTHE.2006.03.018, ISSN 1525-0016, XP005524738.

Written Opinion for International Application No. PCT/US2016/036519, mailed Nov. 7, 2016, 6 Pages.

Written Opinion for International Application No. PCT/US2016/041456, mailed Oct. 19, 2016, 6 Pages.

Written Opinion for International Application No. PCT/US2016/066185, mailed Jun. 9, 2017, 12 Pages.

Written Opinion for International Application No. PCT/US2017/013019, mailed Jul. 17, 2017, 5 Pages.

Written Opinion for International Application No. PCT/US2017/013024, mailed Jul. 14, 2017, 7 Pages.

Written Opinion for International Application No. PCT/US2017/013399, mailed May 26, 2017, 8 Pages.

Written Opinion for International Application No. PCT/US2017/021639, mailed Aug. 25, 2017, 7 Pages.

Written Opinion for International Application No. PCT/US2017/036433, mailed Dec. 15, 2017, 10 Pages.

Written Opinion for International Application No. PCT/US2017/041168, mailed Nov. 8, 2017, 8 Pages.

Written Opinion for International Application No. PCT/US2017/043157, mailed Dec. 26, 2017, 10 Pages.

Written Opinion for International Application No. PCT/US2018/012998, mailed May 29, 2018, 07 Pages.

Written Opinion for International Application No. PCT/US2018/025733, mailed Sep. 24, 2018, 07 Pages.

Written Opinion for International Application No. PCT/US2018/037924, mailed Nov. 9, 2018, 11 Pages.

Written Opinion for International Application No. PCT/US2018/053919, mailed Apr. 12, 2019, 8 Pages.

Wu X., et al., "Development of a Novel Trans-Lentiviral Vector That Affords Predictable Safety," Molecular Therapy, Jul. 2000, vol. 2, No. 1, pp. 47-55.

Yagi H., et al., "Complete Restoration of Phenylalanine Oxidation in Phenylketonuria Mouse by a Self-Complementary Adeno-Associated Virus Vector," Journal of Gene Medicine, 2011, vol. 13(2), pp. 114-122.

Yamano Y., et al., "Clinical Pathophysiology of Human T-Lymphotropic Virus-Type 1-Associated Myelopathy/Tropical Spastic Paraparesis," Frontiers in Microbiology, Nov. 9, 2012, vol. 3, Article. 389, pp. 1-10.

Yang J., et al., "Lentiviral-Mediated Silencing of Famelsyl Pyrophosphate Synthase through RNA Interference in Mice," Biomed Research International, 2015, vol. 2015, Article ID. 914026, 07 pages.

Yano S., et al., "Evaluation of Tetrahydrobiopterin Therapy with Large Neutral Amino Acid Supplementation in Phenylketonuria: Effects on Potential Peripheral Biomarkers, Melatonin and Dopamine, for Brain Monoamine Neurotransmitters," PLoS One, Aug. 11, 2016, vol. 11(8), e0160892, 14 pages.

Ye Y., et al., "Knockdown of Farnesylpyrophosphate Synthase Prevents Angiotensin II-Medicated Cardiac Hypertrophy," The International Journal of Biochemistry & Cell Biology, 2010, vol. 42, pp. 2056-2064.

Yoo L., et al., "PARP-1 Regulates the Expression of Caspase-11," Biochemical and Biophysical Research Communications, Apr. 22, 2011, vol. 408, No. 3, pp. 489-493, DOI: 10.1016/ J. BBRC.2011. 04.070, ISSN: 0006-291X, XP028209824.

(56) References Cited

OTHER PUBLICATIONS

Zufferey R., et al., "Self-Inactivating Lentivirus Vector for Safe and Efficient In Vivo Gene Delivery," Journal of Virology, Dec. 1998, vol. 72(12), pp. 9873-9880.

* cited by examiner

Experimental Vector

Helper Plasmid

Envelope Plasmid

AGT Helper plus Rev plasmid

AGT Envelope plasmid

Lentiviral vector expressing PARP1 shRNA and GFP

AGT Helper plasmid

AGT Rev plasmid

AGT Envelope plasmid

Lentiviral vector expressing PARP1 shRNA and GFP

AGT Helper plus Rev plasmid

AGT Envelope plasmid

Lentiviral vector expressing PARP1 shRNA

AGT Helper plasmid

AGT Rev plasmid                    AGT Envelope plasmid

Lentiviral vector expressing PARP1 shRNA

SEQUENCE LISTING

Sequence total quantity: 61
SEQ ID NO: 1              moltype = DNA  length = 21
FEATURE                   Location/Qualifiers
source                    1..21
                          mol_type = other DNA
                          organism = Homo sapiens
SEQUENCE: 1
cttcgttaga atgtctgcct t                                    21

SEQ ID NO: 2              moltype = DNA  length = 21
FEATURE                   Location/Qualifiers
source                    1..21
                          mol_type = other DNA
                          organism = Homo sapiens
SEQUENCE: 2
gcagcttcat aaccgaagat t                                    21

SEQ ID NO: 3              moltype = DNA  length = 21
FEATURE                   Location/Qualifiers
source                    1..21
                          mol_type = other DNA
                          organism = Homo sapiens
SEQUENCE: 3
ccgagaaatc tcttacctca a                                    21

SEQ ID NO: 4              moltype = DNA  length = 21
FEATURE                   Location/Qualifiers
source                    1..21
                          mol_type = other DNA
                          organism = Homo sapiens
SEQUENCE: 4
cgacctgatc tggaacatca a                                    21

-continued

```
SEQ ID NO: 5          moltype = DNA   length = 19
FEATURE               Location/Qualifiers
source                1..19
                      mol_type = other DNA
                      organism = Homo sapiens
SEQUENCE: 5
gttgctgatg ggtagtacc                                        19

SEQ ID NO: 6          moltype = DNA   length = 53
FEATURE               Location/Qualifiers
source                1..53
                      mol_type = other DNA
                      organism = Homo sapiens
SEQUENCE: 6
cttcgttaga atgtctgcct tctcgagaag gcagacattc taacgaagtt ttt     53

SEQ ID NO: 7          moltype = DNA   length = 53
FEATURE               Location/Qualifiers
source                1..53
                      mol_type = other DNA
                      organism = Homo sapiens
SEQUENCE: 7
gcagcttcat aaccgaagat tctcgagaat cttcggttat gaagctgctt ttt     53

SEQ ID NO: 8          moltype = DNA   length = 53
FEATURE               Location/Qualifiers
source                1..53
                      mol_type = other DNA
                      organism = Homo sapiens
SEQUENCE: 8
ccgagaaatc tcttacctca actcgagttg aggtaagaga tttctcggtt ttt     53

SEQ ID NO: 9          moltype = DNA   length = 53
FEATURE               Location/Qualifiers
source                1..53
                      mol_type = other DNA
                      organism = Homo sapiens
SEQUENCE: 9
cgacctgatc tggaacatca actcgagttg atgttccaga tcaggtcgtt ttt     53

SEQ ID NO: 10         moltype = DNA   length = 52
FEATURE               Location/Qualifiers
source                1..52
                      mol_type = other DNA
                      organism = Homo sapiens
SEQUENCE: 10
gttgctgatg ggtagtacct tcaagagagg tactacccat cagcaacttt tt      52

SEQ ID NO: 11         moltype = DNA   length = 21
FEATURE               Location/Qualifiers
source                1..21
                      mol_type = other DNA
                      organism = Mus musculus
SEQUENCE: 11
gcacttcatg aagctgtatg a                                      21

SEQ ID NO: 12         moltype = DNA   length = 21
FEATURE               Location/Qualifiers
source                1..21
                      mol_type = other DNA
                      organism = Mus musculus
SEQUENCE: 12
gcacagttat cggcagtaac a                                      21

SEQ ID NO: 13         moltype = DNA   length = 21
FEATURE               Location/Qualifiers
source                1..21
                      mol_type = other DNA
                      organism = Mus musculus
SEQUENCE: 13
ggaggcaagt tgacaggatc t                                      21

SEQ ID NO: 14         moltype = DNA   length = 21
FEATURE               Location/Qualifiers
source                1..21
                      mol_type = other DNA
                      organism = Mus musculus
SEQUENCE: 14
tcgacgtcaa ctacgagaaa c                                      21
```

```
SEQ ID NO: 15              moltype = DNA   length = 21
FEATURE                    Location/Qualifiers
source                     1..21
                           mol_type = other DNA
                           organism = Mus musculus
SEQUENCE: 15
gcccttggaa acatgtatga a                                        21

SEQ ID NO: 16              moltype = DNA   length = 53
FEATURE                    Location/Qualifiers
source                     1..53
                           mol_type = other DNA
                           organism = Mus musculus
SEQUENCE: 16
gcacttcatg aagctgtatg actcgagtca tacagcttca tgaagtgctt ttt     53

SEQ ID NO: 17              moltype = DNA   length = 53
FEATURE                    Location/Qualifiers
source                     1..53
                           mol_type = other DNA
                           organism = Mus musculus
SEQUENCE: 17
gcacagttat cggcagtaac actcgagtgt tactgccgat aactgtgctt ttt     53

SEQ ID NO: 18              moltype = DNA   length = 53
FEATURE                    Location/Qualifiers
source                     1..53
                           mol_type = other DNA
                           organism = Mus musculus
SEQUENCE: 18
ggaggcaagt tgacaggatc tctcgagaga tcctgtcaac ttgcctcctt ttt     53

SEQ ID NO: 19              moltype = DNA   length = 53
FEATURE                    Location/Qualifiers
source                     1..53
                           mol_type = other DNA
                           organism = Mus musculus
SEQUENCE: 19
tcgacgtcaa ctacgagaaa cctcgaggtt tctcgtagtt gacgtcgatt ttt     53

SEQ ID NO: 20              moltype = DNA   length = 53
FEATURE                    Location/Qualifiers
source                     1..53
                           mol_type = other DNA
                           organism = Mus musculus
SEQUENCE: 20
gcccttggaa acatgtatga actcgagttc atacatgttt ccaagggctt ttt     53

SEQ ID NO: 21              moltype = DNA   length = 228
FEATURE                    Location/Qualifiers
source                     1..228
                           mol_type = other DNA
                           organism = Rous Sarcoma virus
SEQUENCE: 21
gtagtcttat gcaatactct tgtagtcttg caacatggta acgatgagtt agcaacatgc   60
cttacaagga gagaaaaagc accgtgcatg ccgattggtg gaagtaaggt ggtacgatcg  120
tgccttatta ggaaggcaac agacgggtct gacatggatt ggacgaacca ctgaattgcc  180
gcattgcaga gatattgtat ttaagtgcct agctcgatac aataaacg            228

SEQ ID NO: 22              moltype = DNA   length = 180
FEATURE                    Location/Qualifiers
source                     1..180
                           mol_type = other DNA
                           organism = Rous Sarcoma virus
SEQUENCE: 22
ggtctctctg gttagaccag atctgagcct gggagctctc tggctaacta gggaacccac   60
tgcttaagcc tcaataaagc ttgccttgag tgcttcaagt agtgtgtgcc cgtctgttgt  120
gtgactctgg taactagaga tccctcagac ccttttagtc agtgtggaaa atctctagca  180

SEQ ID NO: 23              moltype = DNA   length = 1503
FEATURE                    Location/Qualifiers
source                     1..1503
                           mol_type = other DNA
                           organism = Human Immunodeficiency Virus
SEQUENCE: 23
atgggtgcga gagcgtcagt attaagcggg ggagaattag atcgatggga aaaaattcgg   60
ttaaggccag gggggaagaa aaaatataaa ttaaaacata tagtatgggc aagcagggag  120
ctagaacgat tcgcagttaa tcctggcctg ttagaaacat cagaaggctg tagacaaata  180
```

```
ctgggacagc tacaaccatc ccttcagaca ggatcagaag aacttagatc attatataat   240
acagtagcaa ccctctattg tgtgcatcaa aggatagaga taaaagacac caaggaagct   300
ttagacaaga tagaggaaga gcaaaacaaa agtaagaaaa aagcacagca agcagcagct   360
gacacaggac acagcaatca ggtcagccaa aattacccta tagtgcagaa catccagggg   420
caaatggtac atcaggccat atcacctaga actttaaatg catgggtaaa agtagtagaa   480
gagaaggctt tcagcccaga agtgataccc atgtttttcag cattatcaga aggagccacc   540
ccacaagatt taaacaccat gctaaacaca gtggggggac atcaagcagc catgcaaatg   600
ttaaaagaga ccatcaatga ggaagctgca gaatgggata gagtgcatcc agtgcatgca   660
gggcctattg caccaggcca gatgagagaa ccaaggggaa gtgacatagc aggaactact   720
agtacccttc aggaacaaat aggatggatg acacataatc cacctatccc agtaggagaa   780
atctataaaa gatggataat cctgggatta aataaaatag taagaatgta tagccctacc   840
agcattctgg acataagaca aggaccaaag gaacccttta gagactatgt agaccgattc   900
tataaaactc taagagccga gcaagcttca caagaggtaa aaaattggat gacagaaacc   960
ttgttggtcc aaaatgcgaa cccagattgt aagactattt taaaagcatt gggaccagga   1020
gcgacactag aagaaatgat gacagcatgt cagggagtgg ggggacccgg ccataaagca   1080
agagttttgg ctgaagcaat gagccaagta acaaatccag ctaccataat gatacagaaa   1140
ggcaatttta ggaaccaaag aaagactgtt aagtgtttca attgtggcaa agaagggcac   1200
atagccaaaa attgcagggc ccctaggaaa aagggctgtt ggaaatgtgg aaaggaagga   1260
caccaaatga aagattgtac tgagagacag gctaattttt tagggaagat ctggccttcc   1320
cacaagggaa ggccagggaa ttttcttcag agcagaccag agccaacagc cccaccagaa   1380
gagagcttca ggtttgggga agagacaaca actccctctc agaagcagga gccgatagac   1440
aaggaactgt atcctttagc ttccctcaga tcactctttg gcagcgaccc ctcgtcacaa   1500
taa                                                                 1503
```

SEQ ID NO: 24             moltype = DNA   length = 233
FEATURE                   Location/Qualifiers
source                    1..233
                          mol_type = other DNA
                          organism = Human Immunodeficiency Virus
SEQUENCE: 24

```
aggagctttg ttccttgggt tcttgggagc agcaggaagc actatgggcg cagcctcaat   60
gacgctgacg gtacaggcca gacaattatt gtctggtata gtgcagcagc agaacaattt   120
gctgagggct attgaggcgc aacagcatct gttgcaactc acagtctggg gcatcaagca   180
gctccaggca agaatcctgg ctgtggaaag atacctaaag gatcaacagc tcc          233
```

SEQ ID NO: 25             moltype = DNA   length = 1519
FEATURE                   Location/Qualifiers
source                    1..1519
                          mol_type = other DNA
                          organism = Vesicular Stomatitis Indiana Virus
SEQUENCE: 25

```
atgaagtgcc ttttgtactt agccttttta ttcattgggg tgaattgcaa gttcaccata   60
gtttttccac acaaccaaaa aggaaactgg aaaaatgttc cttctaatta ccattattgc   120
ccgtcaagct cagatttaaa ttggcataat gacttaatag gcacagcctt acaagtcaaa   180
atgcccaaga gtcacaaggc tattcaagca gacggttgga tgtgtcatgc ttccaaatgg   240
gtcactactg tgtgatttccg ctggtatgga ccgaagtata taacacattc catccgatcc   300
ttcactccat ctgtagaaca atgcaaggaa agcattgaac aaacgaaaca aggaacttgg   360
ctgaatccag gcttccctcc tcaaagttgt ggatatgcaa ctgtgacgga tgccgaagca   420
gtgattgtcc aggtgactcc tcaccatgtg ctggttgatg aatacacagg agaatgggtt   480
gattcacagt tcatcaacgg aaaatgcagc aattacatat gccccactgt ccataactct   540
acaacctggc attctgacta taaggtcaaa gggctatgtg attctaacct catttccatg   600
gacatcacct tcttctcaga ggacggagag ctatcatccc tgggaaagga gggcacaggg   660
ttcagaagta actactttgc ttatgaaact ggaggcaagg cctgcaaaat gcaatactgc   720
aagcattggg gagtcagact cccatcaggt gtctggttcg agatggctga taaggatctc   780
tttgctgcag ccagattccc tgaatgccca gaagggtcaa gtatctctgc tccatctcag   840
acctcagtgg atgtaagtct aattcaggac gttgagagga tcttggatta ttccctctgc   900
caagaaacct ggagcaaaat cagagcgggt cttccaatct ctccagtgga tctcagctat   960
cttgctccta aaaacccagg aaccggtcct gctttcacca taatcaatgg taccctaaaa   1020
tactttggaga ccagatacat cagagtcgat attgctgctc caatcctctc aagaatggtc   1080
ggaatgatca gtggaactac cacagaaagg gaactgtggg atgactgggc accatatgaa   1140
gacgtggaaa ttggacccaa tggagttctg aggaccagtt caggatataa gtttcctttta   1200
tacatgattg gacatggtat gttggactcc gatcttcatc ttagctcaaa ggctcaggtg   1260
ttcgaacatc ctcacattca agacgctgct tcgcaacttc ctgatgatga gagtttattt   1320
tttggtgata ctgggctatc caaaaatcca atcgagcttg tagaaggttg gttcagtagt   1380
tggaaaagct ctattgcctc tttttttcttt atcatagggt taatcattgg actattcttg   1440
gttctccgag ttggtatcca tctttgcatt aaattaaagc acaccaagaa aagacagatt   1500
tatacagaca tagagatga                                                1519
```

SEQ ID NO: 26             moltype = DNA   length = 118
FEATURE                   Location/Qualifiers
source                    1..118
                          mol_type = other DNA
                          organism = Rous Sarcoma virus
SEQUENCE: 26

```
ttttaaaaga aaaggggggga ttgggggggta cagtgcaggg gaaagaatag tagacataat   60
agcaacagac atacaaacta agaattaca aaaacaaatt acaaaattca aaattttta    118
```

SEQ ID NO: 27             moltype = DNA   length = 217
FEATURE                   Location/Qualifiers -continued

```
source                  1..217
                        mol_type = other DNA
                        organism = Rous Sarcoma virus
SEQUENCE: 27
gaacgctgac gtcatcaacc cgctccaagg aatcgcgggc ccagtgtcac taggcgggaa    60
cacccagcgc gcgtgcgccc tggcaggaag atggctgtga gggacagggg agtggcgccc    120
tgcaatattt gcatgtcgct atgtgttctg ggaaatcacc ataaacgtga aatgtctttg    180
gatttgggaa tcttataagt tctgtatgag accactt                             217

SEQ ID NO: 28             moltype = DNA  length = 532
FEATURE                   Location/Qualifiers
source                    1..532
                          mol_type = other DNA
                          organism = Rous Sarcoma virus
SEQUENCE: 28
gctccggtgc ccgtcagtgg gcagagcgca catcgcccac agtccccgag aagttggggg    60
gaggggtcgg caattgaacg ggtgcctaga aaggtggcg cggggtaaac tgggaaagtg    120
atgtcgtgta ctggctccgc ctttttcccg agggtggggg agaaccgtat ataagtgcag    180
tagtcgccgt gaacgttctt tttcgcaacg ggtttgccgc cagaacacag ctgaagcttc    240
gagggggctcg catctctcct tcacgcgccc gccgccctac ctgaggccgc catccacgcc    300
ggttgagtcg cgttctgccg cctcccgcct gtggtgcctc ctgaactgcg tccgccgtct    360
aggtaagttt aaagctcagg tcgagaccgg gcctttgtcc ggcgctccct tggagcctac    420
ctagactcag ccggctctcc acgctttgcc tgacctgct tgctcaactc tacgtctttg    480
tttcgttttc tgttctgcgc cgttacagat ccaagctgtg accggcgcct ac            532

SEQ ID NO: 29             moltype = DNA  length = 759
FEATURE                   Location/Qualifiers
source                    1..759
                          mol_type = other DNA
                          organism = Aequorea victoria
SEQUENCE: 29
atggagagcg acgagagcgg cctgcccgcc atggagatcg agtgccgcat caccggcacc    60
ctgaacggcg tggagttcga gctggtgggc ggcggagagg gcacccccaa gcagggccgc    120
atgaccaaca agatgaagag caccaaaggc gccctgacct tcagccccta cctgctgagc    180
cacgtgatgg gctacggctt ctaccacttc ggcacctacc ccagcggcta cgagaacccc    240
ttcctgcacg ccatcaacaa cggcggctac accaacacc gcatcgagaa gtacgaggac    300
ggcggcgtgc tgcacgtgag cttcagctac cgctacgagg ccggccgcgt gatcggcgac    360
ttcaaggtgg tgggcaccgg cttccccgag gacagcgtga tcttcaccga caagatcatc    420
cgcagcaacg ccaccgtgga gcacctgcac cccatgggcg ataacgtgct ggtgggcgac    480
ttcgcccgca ccttcagcct gcgcgacggc ggctactaca gcttcgtggt ggacagccac    540
atgcacttca agagcgccat ccacccagc atcctgcaga acgggggccc catgttcgcc    600
ttccgccgcg tggaggagct gcacagcaac accgagctgg gcatcgtgga gtaccagcac    660
gccttcaaga cccccatcgc cttcgccaga tcccgcgctc agtcgtccaa ttctgccgtg    720
gacggcaccg ccggacccgg ctccaccgga tctcgctaa                           759

SEQ ID NO: 30             moltype = DNA  length = 590
FEATURE                   Location/Qualifiers
source                    1..590
                          mol_type = other DNA
                          organism = Woodchuck hepatitis B virus
SEQUENCE: 30
aatcaacctc tgattacaaa atttgtgaaa gattgactgg tattcttaac tatgttgctc    60
cttttacgct atgtggatac gctgctttaa tgcctttgta tcatgctatt gcttcccgta    120
tggctttcat tttctcctcc ttgtataaat cctggttgct gtctctttat gaggagttgt    180
ggcccgttgt caggcaacgt ggcgtggtgt gcactgtgtt tgctgacgca acccccactg    240
gttggggcat gccaccacc tgtcagctcc tttccgggac tttcgctttc ccctcccta     300
ttgccacggc ggaactcatc gccgcctgcc ttgcccgctg ctggacaggg gctcggctgt    360
tgggcactga caattccgtg gtgttgtcgg ggaaatcatc gtcctttcct ggctgctcg     420
cctgtgttgc cacctggatt ctgcgcggga cgtccttctg ctacgtccct tcggccctca    480
atccagcgga ccttccttcc gcggcctgc tgccggctct tcccgcgtct tcc            540
gccttcgccc tcagacgagt cggatctccc tttgggccgc ctccccgcct              590

SEQ ID NO: 31             moltype = DNA  length = 250
FEATURE                   Location/Qualifiers
source                    1..250
                          mol_type = other DNA
                          organism = Human Immunodeficiency Virus
SEQUENCE: 31
tggaagggct aattcactcc caacgaagat aagatctgct ttttgcttgt actgggtctc    60
tctggttaga ccagatctga gcctgggagc tctctggcta actagggaac ccactgctta    120
agcctcaata aagcttgcct tgagtgcttc aagtagtgtg tgcccgtctg ttgtgtgact    180
ctggtaacta gagatccctc agacccttt agtcagtgtg gaaaatctct agcagtagta    240
gttcatgtca                                                            250

SEQ ID NO: 32             moltype = DNA  length = 352
FEATURE                   Location/Qualifiers
misc_feature             1..352
                          note = Helper/Rev CMV early (CAG) enhancer DNA construct
source                    1..352
```

-continued

```
                              mol_type = other DNA
                              organism = synthetic construct
SEQUENCE: 32
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggac tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tc          352

SEQ ID NO: 33          moltype = DNA   length = 290
FEATURE                Location/Qualifiers
misc_feature           1..290
                       note = Helper/Rev Chicken beta actin (CAG) promoter DNA
                        construct
source                 1..290
                       mol_type = other DNA
                       organism = synthetic construct
SEQUENCE: 33
gctattacca tgggtcgagg tgagccccac gttctgcttc actctcccca tctcccccc    60
ctccccaccc ccaattttgt atttatttat tttttaatta ttttgtgcag cgatgggggc   120
ggggggaggg ggggcgcgcg ccaggcgggg cggggcgggg cgagggggcg ggcggggcga   180
ggcggagagg tgcggcggca gccaatcaga gcggcgcgct ccgaaagttt cctttatgg   240
cgaggcggcg gcggcggcgg ccctataaaa agcgaagcgc gcggcgggcg              290

SEQ ID NO: 34          moltype = DNA   length = 960
FEATURE                Location/Qualifiers
misc_feature           1..960
                       note = Helper/Rev Chicken beta actin intron DNA construct
source                 1..960
                       mol_type = other DNA
                       organism = synthetic construct
SEQUENCE: 34
ggagtcgctg cgttgccttc gccccgtgcc ccgctccgcg ccgcctcgcg ccgcccgccc    60
cggctctgac tgaccgcgtt actcccacag gtgagccgcg gggacggcc ttctcctccg   120
ggctgtaatt agcgcttggt ttaatgacgg ctcgtttctt ttctgtggct gcgtgaaagc   180
cttaaagggc tccgggaggg ccctttgtgc ggggggagc ggctcgggggg gtgcgtgcgt   240
gtgtgtgtgc gtggggagcg ccgcgtgcgg cccgcgctgc ccggcggctg tgagcgctgc   300
gggcgcggcg cggggctttg tgcgctccgc gtgtgcgcga ggggagcgcg gccggggcga   360
gtgccccgcg gtgcgggggg gctgcgaggg gaacaaaggc tgcgtgcggg gtgtgtgcgt   420
ggggggggtga gcaggggtg tgggcgcggc ggtcgggctg taacccccc ctgcacccc    480
ctccccgagt tgctgagcac ggcccggctt cgggtgcggg gctccgtgcg gggcgtggcg   540
cggggctcgc cgtgccgggc gggggtggc ggcaggtggg ggtgccggc gggcgggc    600
cgcctcgggc cggggagggc tcgggggagg ggcgcggcgg ccccggagcg ccggcggctg   660
tcgaggcgcg gcgagccgca gccattgcct tttatggtaa tcgtgcgaga gggcgcaggg   720
acttcctttg tcccaaatct ggcggagccg aaatctggga ggcgccgcg cacccctct    780
agcgggcgcg ggcggaagcgg tgcggcgccg gcaggaagga aatgggcggg gagggccttc   840
gtgcgtcgcc gcgccgccgt ccccttctcc atctccagcc tcggggctgc cgcagggggga   900
cggctgcctt cgggggggac ggggcagggc ggggttcggc ttctggcgtg tgaccggcgg   960

SEQ ID NO: 35          moltype = DNA   length = 1872
FEATURE                Location/Qualifiers
misc_feature           1..1872
                       note = Helper/Rev HIV Pol DNA construct
source                 1..1872
                       mol_type = other DNA
                       organism = synthetic construct
SEQUENCE: 35
atgaatttgc caggaagatg gaaaccaaaa atgatagggg gaattggagg ttttatcaaa    60
gtaggacagt atgatcagat actcatagaa atctgcggac ataaagctat aggtacagta   120
ttagtaggac ctacacctgt caacataatt ggaagaaatc tgttgactca gattggctgc   180
actttaaatt ttcccattag tcctattgag actgtaccag taaaattaaa gccaggaatg   240
gatggcccaa aagttaaaca atggccattg acagaagaaa aaataaaagc attagtagaa   300
atttgtacag aaatggaaaa ggaaggaaaa atttcaaaa ttgggcctga aaatccatac   360
aatactccag tatttgccat aaagaaaaaa gacagtacta aatggagaaa attagtagat   420
ttcagagaac ttaataagag aactcaagat ttctgggaag ttcaattagg aataccacat   480
cctgcagggt taaaacagaa aaaatcagta acagtactgg atgtgggcga tgcatatttt   540
tcagttccct tagataaaga cttcaggaag tatactgcat ttaccatacc tagtataaac   600
aatgagacac cagggattag atatcagtac aatgtgcttc cacagggatg gaaaggatca   660
ccagcaatat tccagtgtag catgacaaaa atcttagagc cttttagaaa acaaaatcca   720
gacatagtca tctatcaata catggatgat ttgtatgtag gatctgactt agaaataggg   780
cagcatagaa caaaaataga ggaactgaga caacatctgt tgaggtgggg atttaccaca   840
ccagacaaaa aacatcagaa agaacctcca ttcctttgga tgggttatga actccatcct   900
gataaatgga cagtacagcc tatagtgctg ccagaaaaag acagctggac tgtcaatgac   960
atacagaaat tagtgggaaa attgaattgg gcaagtcaga tttatgcagg gattaaagta   1020
aggcaattat gtaaacttct tagggganacc aaagcactaa cagaagtagt accactaaca   1080
gaagaagcag agctagaact ggcagaaaac agggagattc taaaagaacc ggtacatgga   1140
gtgtattatg acccatcaaa agacttaata gcagaaatac agaagcaggg gcaaggccaa   1200
tggacatatc aaatttatca agagccattt aaaaatctga aaacaggaaa atatgcaaga   1260
```

```
atgaagggtg cccacactaa tgatgtgaaa caattaacag aggcagtaca aaaaatagcc  1320
acagaaagca tagtaatatg gggaaagact cctaaattta aattacccat acaaaaggaa  1380
acatgggaag catggtggac agagtattgg caagccacct ggattcctga gtgggagttt  1440
gtcaataccc ctcccttagt gaagttatgg taccagttag agaaagaacc cataatagga  1500
gcagaaactt tctatgtaga tggggcagcc aataggggaa ctaaattagg aaaagcagga  1560
tatgtaactg acagaggaag acaaaaagtt gtccccctaa cggacacaac aaatcagaag  1620
actgagttac aagcaattca tctagctttg caggattcgg gattagaagt aaacatagtg  1680
acagactcac aatatgcatt gggaatcatt caagcacaac cagataagag tgaatcagag  1740
ttagtcagtc aaataataga gcagttaata aaaaaggaaa aagtctacct ggcatgggta  1800
ccagcacaca aaggaattgg aggaaatgaa caagtagatg ggttggtcag tgctggaatc  1860
aggaaagtac ta                                                      1872
```

```
SEQ ID NO: 36              moltype = DNA  length = 867
FEATURE                    Location/Qualifiers
misc_feature              1..867
                           note = Helper Rev HIV Integrase DNA construct
source                     1..867
                           mol_type = other DNA
                           organism = synthetic construct
SEQUENCE: 36
tttttagatg gaatagataa ggcccaagaa gaacatgaga aatatcacag taattggaga  60
gcaatggcta gtgattttaa cctaccacct gtagtagcaa aagaaatagt agccagctgt  120
gataaatgtc agctaaaagg ggaagccatg catggacaag tagactgtag cccaggaata  180
tggcagctag attgtacaca tttagaagga aaagttatct tggtagcagt tcatgtagcc  240
agtggatata tagaagcaga agtaattcca gcagagacag ggcaagaaac agcatacttc  300
ctcttaaaat tagcaggaag atggccagta aaaacagta acagacaa tggcagcaat  360
ttcaccagta ctacagttaa ggccgcctgt tggtgggcgg ggatcaagca ggaatttggc  420
attccctaca atccccaaag tcaaggagta atagaatcta tgaataaaga attaaagaaa  480
attataggac aggtaagaga tcaggctgaa catcttaaga cagcagtaca aatggcagta  540
ttcatccaca atttttaaaag aaaaggggg attgggggat acagtgcagg ggaaagaata  600
gtagacataa tagcaacaga catacaaact aaagaattac aaaaacaaat tacaaaaatt  660
caaaattttc gggtttatta cagggacagc agagatccag tttggaaagg accagcaaag  720
ctcctctgga aaggtgaagg ggcagtagta atacaagata atagtgacat aaaagtagtg  780
ccaagaagaa aagcaaagat catcagggat tatggaaaac agatggcagg tgatgattgt  840
gtggcaagta gacaggatga ggattaa                                      867
```

```
SEQ ID NO: 37              moltype = DNA  length = 351
FEATURE                    Location/Qualifiers
misc_feature              1..351
                           note = Helper/Rev HIV Rev DNA construct
source                     1..351
                           mol_type = other DNA
                           organism = synthetic construct
SEQUENCE: 37
atggcaggaa gaagcggaga cagcgacgaa gaactcctca aggcagtcag actcatcaag  60
tttctctatc aaagcaaccc acctcccaat cccgaggg cccgacaggc ccgaaggaat  120
agaagagaa ggtggagaga gagacagaga cagatccatt cgattagtga acggatcctt  180
agcacttatc tgggacgatc tgcggagcct gtgcctcttc agctaccacc gcttgagaga  240
cttactcttg attgtaacga ggattgtgga acttctggga cgcagggggt gggaagccct  300
caaatattgt ggaatctcc tacaatattg gagtcaggag ctaaagaata g           351
```

```
SEQ ID NO: 38              moltype = DNA  length = 448
FEATURE                    Location/Qualifiers
misc_feature              1..448
                           note = Helper/Rev Rabbit beta globin poly A DNA construct
source                     1..448
                           mol_type = other DNA
                           organism = synthetic construct
SEQUENCE: 38
agatcttttt ccctctgcca aaaattatgg ggacatcatg aagccccttg agcatctgac  60
ttctggctaa taaaggaaat ttattttcat tgcaatagtg tgttggaatt ttttgtgtct  120
ctcactcgga aggacatatg ggagggcaaa tcatttaaaa catcagaatg agtatttggt  180
ttagagtttg gcaacatatg ccatatgctg ctgccatga acaaaggtgg ctataaagag  240
gtcatcagta tatgaaacag cccccctgctg tccattcctt attccataga aaagccttga  300
cttgaggtta gatttttttt atattttgtt ttgtgttatt ttttctttta acatccctaa  360
aatttttcctt acatgtttta ctagccagat ttttcctcct ctcctgacta ctcccagtca  420
tagctgtccc tcttctctta tgaagatc                                     448
```

```
SEQ ID NO: 39              moltype = DNA  length = 577
FEATURE                    Location/Qualifiers
source                     1..577
                           mol_type = other DNA
                           organism = Cytomegalovirus
SEQUENCE: 39
acattgatta ttgactagtt attaatagta atcaattacg gggtcattag ttcatagccc  60
atatatggag ttccgcgtta cataacttac ggtaaatggc ccgcctggct gaccgcccaa  120
cgacccccgc ccattgacgt caataatgac gtatgttccc atagtaacgc caatagggac  180
tttccattga cgtcaatggg tggagtattt acggtaaact gcccacttgg cagtacatca  240
agtgtatcat atgccaagta cgcccctat tgacgtcaat gacggtaaat ggcccgcctg  300
```

```
gcattatgcc cagtacatga ccttatggga ctttcctact tggcagtaca tctacgtatt   360
agtcatcgct attaccatgg tgatgcggtt ttggcagtac atcaatgggc gtggatagcg   420
gtttgactca cggggatttc caagtctcca ccccattgac gtcaatggga gtttgttttg   480
gcaccaaaat caacgggact ttccaaaatg tcgtaacaac tccgccccat tgacgcaaat   540
gggcggtagg cgtgtacggt gggaggtcta tataagc                            577

SEQ ID NO: 40           moltype = DNA  length = 573
FEATURE                 Location/Qualifiers
source                  1..573
                        mol_type = other DNA
                        organism = Homo sapiens
SEQUENCE: 40
gtgagtttgg ggacccttga ttgttctttc tttttcgcta ttgtaaaatt catgttatat   60
ggaggggggca aagttttcag ggtgttgttt agaatggaa gatgtccctt gtatcaccat   120
ggaccctcat gataattttg tttctttcac tttctactct gttgacaacc attgtctcct   180
cttattttct tttcattttc tgtaactttt tcgttaaact ttagcttgca tttgtaacga   240
attttaaat tcactttgt ttatttgtca gattgtaagt actttctcta atcactttt    300
tttcaaggca atcagggtat attatattgt acttcagcac agtttttagag aacaattgt   360
ataattaaat gataaggtag aatatttctg catataaatt ctggctggcg tggaaatatt   420
cttattggta gaaacaacta caccctggtc atcatcctgc ctttctcttt atggttacaa   480
tgatatacac tgtttgagat gaggataaaa tactctgagt ccaaaccggg cccctctgct   540
aaccatgttc atgccttctt ctctttccta cag                                573

SEQ ID NO: 41           moltype = DNA  length = 31
FEATURE                 Location/Qualifiers
misc_feature            1..31
                        note = Primer DNA fragment
source                  1..31
                        mol_type = other DNA
                        organism = synthetic construct
SEQUENCE: 41
taagcagaat tcatgaattt gccaggaaga t                                   31

SEQ ID NO: 42           moltype = DNA  length = 36
FEATURE                 Location/Qualifiers
misc_feature            1..36
                        note = Primer DNA fragment
source                  1..36
                        mol_type = other DNA
                        organism = synthetic construct
SEQUENCE: 42
ccatacaatg aatggacact aggcggccgc acgaat                              36

SEQ ID NO: 43           moltype = DNA  length = 2745
FEATURE                 Location/Qualifiers
misc_feature            1..2745
                        note = Gag, Pol, Integrase DNA fragment
source                  1..2745
                        mol_type = other DNA
                        organism = synthetic construct
SEQUENCE: 43
gaattcatga atttgccagg aagatggaaa ccaaaaatga tagggggaat tggaggtttt   60
atcaaagtaa gacagtatga tcagatactc atagaaatct gcggacataa agctataggg   120
acagtattag taggacctac acctgtcaac ataattggaa gaaatctgtt gactcagatt   180
ggctgcactt taaattttcc cattagtcct attgagactg taccagtaaa attaaagcca   240
ggaatggatg gcccaaaagt taaacaatgg ccattgacag aagaaaaaat aaaagcatta   300
gtagaaattt gtacagaaat ggaaaaggaa ggaaaaattt caaaaattgg gcctgaaaat   360
ccatacaata ctccagtatt tgccataaag aaaaaagaca gtactaaatg gagaaaatta   420
gtagatttca gagaacttaa taagagaact caagatttct gggaagttca attaggaata   480
ccacatcctg cagggttaaa acagaaaaaa tcagtaacag tactggatgt gggcgatgca   540
tatttttcag ttcccttaga taaagacttc aggaagtata ctgcatttac catacctagt   600
ataaacaatg agacaccagg gattagatat cagtacaatg tgcttccaca gggatggaaa   660
ggatcaccag caatattcca gtgtagcatg acaaaaatct tagagccttt tagaaaacaa   720
aatccagaca gtgtcatcta tcaatacatg gatgatttgt atgtaggatc tgacttagaa   780
ataggggcagc atagaacaaa aatagaggaa ctgagacaac atctgttgag gtggggattt   840
accacaccag acaaaaaaca tcagaaagaa cctccattcc tttggatggg ttatgaactc   900
catcctgata aatggacagt acagcctata gtgctgccag aaaaggacag ctggactgtc   960
aatgacatac agaaattagt gggaaaattg aattgggca gtcagattta tgcagggatt   1020
aaagtaaggc aattatgtaa acttcttagg ggaaccaaag cactaacaga agtagtacca   1080
ctaacagaag aagcagagct agaactggca gaaaacaggg agattctaaa agaaccggta   1140
catggagtgt attatgaccc atcaaaagac ttaatagcag aaatacagaa gcaggggcaa   1200
ggccaatgga catatcaaat ttatcaagag ccatttaaaa atctgaaaac aggaaagtat   1260
gcaagaatga agggtgccca cactaatgat gtaaacaat aacagaggc agtacaaaaa   1320
atagccacag aaagcatagt aatatgggga aagactccta aatttaaatt acccatacaa   1380
aaggaaacat gggaagcatg gtggacagag tattggcaag ccacctggat tcctgagtgg   1440
gagtttgtca atacccctcc cttagtgaag ttatggtacc agttagagaa agaacccata   1500
ataggagcag aaactttcta tgtagatggg gcagccaata gggaaactaa attaggaaaa   1560
gcaggatatg taactgacag aggaagacaa aaagttgtcc ccctaacgga cacaacaaat   1620
cagaagactg agttacaagc aattcatcta gctttgcagg attcgggatt agaagtaaac   1680
```

-continued

```
atagtgacag actcacaata tgcattggga atcattcaag cacaaccaga taagagtgaa   1740
tcagagttag tcagtcaaat aatagagcag ttaataaaaa aggaaaaagt ctacctggca   1800
tgggtaccag cacacaaagg aattggagga aatgaacaag tagataaatt ggtcagtgct   1860
ggaatcagga aagtactatt tttagatgga atagataagg cccaagaaga acatgagaaa   1920
tatcacagta attggagagc aatggctagt gattttaacc taccacctgt agtagcaaaa   1980
gaaatagtag ccagctgtga taaatgtcag ctaaaagggg aagccatgca tggacaagta   2040
gactgtagcc caggaatatg gcagctagat tgtacacatt tagaaggaaa agttatcttg   2100
gtagcagttc atgtagccag tggatatata gaagcagaag taattccagc agagacaggg   2160
caagaaacag catacttcct cttaaaatta gcaggaagat ggccagtaaa aacagtacat   2220
acagacaatg gcagcaattt caccagtact acagttaagg ccgcctgttg gtgggcgggg   2280
atcaagcagg aatttggcat tccctacaat ccccaaagtc aaggagtaat agaatctatg   2340
aataaagaat taaagaaaat tataggacag gtaagagatc aggctgaaca tcttaagaca   2400
gcagtacaaa tggcagtatt catccacaat tttaaaagaa aaggggggat tggggggtac   2460
agtgcagggg aaagaatagt agacataata gcaacagaca tacaaactaa agaattacaa   2520
aaacaaatta caaaaattca aaattttcgg gtttattaca gggacagcag agatccagtt   2580
tggaaaggac cagcaaagct cctctggaaa ggtgaagggg cagtagtaat acaagataat   2640
agtgacataa aagtagtgcc aagaagaaaa gcaaagatca tcaggggatta tggaaaacag   2700
atggcaggtg atgattgtgt ggcaagtaga caggatgagg attaa                    2745
```

```
SEQ ID NO: 44             moltype = DNA   length = 1586
FEATURE                   Location/Qualifiers
misc_feature              1..1586
                          note = Rev, RRE and rabbit beta globin poly A DNA fragment
source                    1..1586
                          mol_type = other DNA
                          organism = synthetic construct
SEQUENCE: 44
tctagaatgg caggaagaag cggagacagc gacgaagagc tcatcagaac agtcagactc   60
atcaagcttc tctatcaaag caacccacct cccaatcccg aggggacccg acaggcccga   120
aggaatagaa gaagaaggtg gagagagaga cagagacaga tccattcgat tagtgaacgg   180
atccttggca cttatctggg acgatctgcg gagcctgtgc ctcttcagct accaccgctt   240
gagagactta ctcttgattg taacgaggat tgtggaactt ctgggacgca gggggtggga   300
agccctcaaa tattggtgga atctcctaca atattggagt caggagctaa agaatagagg   360
agctttgttc cttgggttct tgggagcagc aggaagcact atgggcgcag cgtcaatgac   420
gctgacggta caggccagac aattattgtc tggtatagtg cagcagcaga acaatttgct   480
gagggctatt gaggcgcaac agcatctgtt gcaactcaca gtctggggca tcaagcagct   540
ccaggcaaga atcctggctg tggaaagata cctaaaggat caacagctcc tagatctttt   600
tccctctgcc aaaaattatg gggacatcat gaagcccctt gagcatctga cttctggcta   660
ataaaggaaa tttattttca ttgcaatagt gtgttggaat tttttgtgtc tctcactcgg   720
aaggacatat gggagggcaa atcatttaaa acatcagaat gagtatttgg tttagagttt   780
ggcaacatat gccatatgct ggctgccatg aacaaaggtg gctataaaga ggtcatcagt   840
atatgaaaca gccccctgct gtccattcct tattccatag aaaagccttg acttgaggtt   900
agattttttt tatattttgt tttgtgttat tttttctt aacatccca aaattttcct      960
tacatgtttt actagccaga ttttcctcc tctcctgact actcccagtc atagctgtcc    1020
ctcttctctt atgaagatcc ctcgacctgc agcccaagct tggcgtaatc atggtcatag   1080
ctgtttcctg tgtgaaattg ttatccgctc acaattccac acaacatacg agccggaagc   1140
ataaagtgta aagcctgggg tgcctaatga gtgagctaac tcacattaat tgcgttgcgc   1200
tcactgcccg ctttccagtc gggaaacctg tcgtgccagc ggatccgcat ctcaattagt   1260
cagcaaccat agtcccgccc ctaactccgc ccatcccgcc cctaactccg cccagttccg   1320
cccattctcc gccccatggc tgactaattt ttttatttta tgcagaggcc gaggccgcct   1380
cggcctctga gctattccag aagtagtgag gaggctttt tggaggccta ggcttttgca    1440
aaaagctaac ttgtttattg cagcttataa tggttacaaa taaagcaata gcatcacaaa   1500
tttcacaaat aaagcatttt tttcactgca ttctagttgt ggtttgtcca aactcatcaa   1560
tgtatcttat cagcggccgc cccggg                                         1586
```

```
SEQ ID NO: 45             moltype = DNA   length = 1614
FEATURE                   Location/Qualifiers
misc_feature              1..1614
                          note = CAG enhancer/promoter/intron sequence DNA fragment
source                    1..1614
                          mol_type = other DNA
                          organism = synthetic construct
SEQUENCE: 45
acgcgttagt tattaatagt aatcaattac ggggtcatta gttcatagcc catatatgga   60
gttccgcgtt acataactta cggtaaatgg cccgcctggc tgaccgccca acgacccccg   120
cccattgacg tcaataatga cgtatgttcc catagtaacg ccaatagga ctttccattg    180
acgtcaatgg gtggactatt tacggtaaac tgcccacttg gcagtacatc aagtgtatca   240
tatgccaagt acgccccta ttgacgtcaa tgacggtaaa tggcccgcct ggcattatgc    300
ccagtacatg acttatggg actttcctac ttggcagtac atctacgtat tagtcatcgc    360
tattaccatg gtcgaggtg agccccacgt tctgcttcac tctccccatc tcccccccct     420
cccacccccc aatttgtat ttatttattt tttaattatt ttgtgcagcg atggggggcgg    480
ggggggggg ggcgcgcgcc aggcggggcg gggcggggcg aggggcgggg cggggcgagg     540
cggagaggtg cggcggcagc caatcagagc ggcgcgctcc gaaagtttcc ttttatggcg    600
aggcggcggc ggcggcggcc ctataaaaag cgaagcgcgc ggcgggcggg agtcgctgcg    660
ttgccttcgc cccgtgcccc gctccgcgcc gcctcgcgcc gcccgccccg gctctgactg    720
accgcgttac tcccacaggt gagcgggcgg gacggccctt ctcctccggg ctgtaattag    780
cgcttggttt aatgacggct cgtttctttt ctgtggctgc gtgaaagcct taaagggctc    840
cgggagggcc ctttgtgcgg gggggagcgg ctcgggggt gcgtgcgtgt gtgtgtgcgt      900
ggggagcgc gcgtgcggcc cgcgctgccc ggcggctgtg agcgctgcgg gcgcggcgcg     960
```

-continued

```
gggctttgtg cgctccgcgt gtgcgcgagg ggagcgcggc cggggcgcggt gccccgcggt   1020
gcggggggggc tgcgaggggga acaaaggctg cgtgcggggt gtgtgcgtgg ggggggtgagc   1080
aggggggtgtg ggcgcggcgg tcgggctgta accccccct gcacccccct ccccgagttg   1140
ctgagcacgg cccggcttcg ggtgcggggc tccgtgcggg gcgtggcgcg gggctcgccg   1200
tgccgggcgg gggggtggcgg caggtggggg tgccggggcg cctcgggccg   1260
gggagggctc gggggagggg cgcggcggcc ccggagcgcc ggcggctgtc gaggcgcggc   1320
gagccgcagc cattgccttt tatggtaatc gtgcgagagg gcgcagggac ttcctttgtc   1380
ccaaatctgg cggagccgaa atctgggagg cgccgccgca cccctctag cgggcgcggg   1440
cgaagcggtg cggcgccggc aggaaggaaa tgggcgggga gggccttcgt gcgtcgccgc   1500
gccgccgtcc ccttctccat ctccagcctc ggggctgccg cagggggacg gctgccttcg   1560
gggggggacgg ggcagggcgg ggttcggctt ctggcgtgtg accggcggga attc   1614
```

SEQ ID NO: 46          moltype = DNA  length = 1531
FEATURE                Location/Qualifiers
source                 1..1531
                       mol_type = other DNA
                       organism = Vesicular Stomatitis Indiana Virus
SEQUENCE: 46

```
gaattcatga agtgcctttt gtacttagcc tttttattca ttggggtgaa ttgcaagttc   60
accatagttt ttccacacaa ccaaaaagga aactggaaaa atgttccttc taattaccat   120
tattgcccgt caagctcaga tttaaattgg cataatgact taataggcac agccttacaa   180
gtcaaaatgc ccaagagtca caaggctatt caagcagacg gttggatgtg tcatgcttcc   240
aaatgggtca ctacttgtga tttccgctgg tatggaccga agtatataac acattccatc   300
cgatccttca ctccatctgt agaacaatgc aaggaaagca ttgaacaaac gaaacaagga   360
acttggctga atccaggctt ccctcctcaa agttgtggat atgcaactgt gacggatgcc   420
gaagcagtga ttgtccaggt gactcctcac catgtgctgg ttgatgaata cacaggagaa   480
tgggttgatt cacagttcat caacggaaaa tgcagcaatt acatatgccc cactgtccat   540
aactctacaa cctggcattc tgactataag gtcaaagggc tatgtgattc taacctcatt   600
tccatggaca tcaccttctt ctcagaggac ggagagctat catccctggg aaaggagggc   660
acagggttca gaagtaacta ctttgcttat gaaactgagg gcaaggcctg caaaatgcaa   720
tactggcaagc attggggagt cagactccca tcaggtgtct ggttcgagat ggctgataag   780
gatctctttg ctgcagccag attccctgaa tgcccagaag ggtcaagtat ctctgctcca   840
tctcagacct cagtggatgt aagtctaatt caggacgttg agaggatctt ggattattcc   900
ctctgccaag aaacctggag caaaatcaga gcgggtcttc caatctctcc agtggatctc   960
agctatcttg ctcctaaaaa cccaggaacc ggtcctgctt tcaccataat caatggtacc   1020
ctaaaatact ttgagaccag atacatcaga gtcgatattg ctgctccaat cctctcaaga   1080
atggtcggaa tgatcagtgg aactaccaca gaaagggaac tgtgggatga ctgggcacca   1140
tatgaagacg tggaaattgg acccaatgga gttctgagga ccagttcagg atataagttt   1200
cctttataca tgattggaca tggtatgttg gactccgatc ttcatcttag ctcaaaggct   1260
caggtgttcg aacatcctca cattcaagac gctgcttcgc aacttcctga tgatgagagt   1320
ttattttttg gtgatactgg gctatccaaa aatccaatcg agcttgtaga aggttggttc   1380
agtagttgga aaagctctat tgcctctttt ttctttatca tagggttaat cattggacta   1440
ttcttggttc tccgagttgg tatccatctt tgcattaaat taaagcacac caagaaaaga   1500
cagatttata cagacataga gatgagaatt c                                   1531
```

SEQ ID NO: 47          moltype = DNA  length = 351
FEATURE                Location/Qualifiers
source                 1..351
                       mol_type = other DNA
                       organism = Rous Sarcoma Virus
SEQUENCE: 47

```
atggcaggaa gaagcggaga cagcgacgaa gaactcctca aggcagtcag actcatcaag   60
tttctctatc aaagcaaccc acctcccaat cccgaggggga cccgacaggc ccgaaggaat   120
agaagaagaa ggtggagaga gagacagaga cagatccatt cgattagtga acggatcctt   180
agcacttatc tgggacgatc tgcggagcct gtgcctcttc agctaccacc gcttgagaga   240
cttactcttg attgtaacga ggattgtgga acttctgagc gcaggggggt gggaagccct   300
caaatattgg tggaatctcc tacaatattg gagtcaggag ctaaagaata g            351
```

SEQ ID NO: 48          moltype = DNA  length = 884
FEATURE                Location/Qualifiers
misc_feature           1..884
                       note = Rous Sarcoma Virus (RSV) promoter and Human
                        Immunodeficiency Virus (HIV) Rev DNA fragment
source                 1..884
                       mol_type = other DNA
                       organism = synthetic construct
SEQUENCE: 48

```
caattgcgat gtacgggcca gatatacgcg tatctgaggg gactagggtg tgtttaggcg   60
aaaagcgggg cttcggttgt acgcggttag gagtcccctc aggatatagt agtttcgctt   120
ttgcataggg aggggggaaat gtagtcttat gcaatacact tgtagtcttg caacatggta   180
acgatgagtt agcaacatgc cttacaagga gagaaaaagc accgtgcatg ccgattggtg   240
gaagtaaggt ggtacgatcg tgccttatta ggaaggcaac agacaggtct gacatggatt   300
ggacgaacca ctgaattccg cattgcagag ataattgtat ttaagtgcct agctcgatac   360
aataaacgcc atttgaccat tcaccacatt ggtgtgcacc tccaagctcg agctcgttta   420
gtgaaccgtc agatcgcctg gagacgccat ccacgctgtt ttgacctcca tagaagacac   480
cgggaccgat ccagcctccc ctcgaagcta gcgattaggc atctcctatg gcaggaagaa   540
gcggagacag cgacgaagaa ctcctcaagg cagtcagact catcaagttt ctctatcaaa   600
gcaacccacc tcccaatccc gaggggaccc gacaggcccg aaggaataga agaagaaggt   660
ggagagagag acagagacag atccattcga ttagtgaacg gatccttagc acttatctgg   720
```

```
gacgatctgc ggagcctgtg cctcttcagc taccaccgct tgagagactt actcttgatt    780
gtaacgagga ttgtggaact tctgggacgc aggggtgggg aagccctcaa atattggtgg    840
aatctcctac aatattggag tcaggagcta aagaatagtc taga                     884

SEQ ID NO: 49          moltype = DNA   length = 511
FEATURE                Location/Qualifiers
source                 1..511
                       mol_type = other DNA
                       organism = Homo sapiens
SEQUENCE: 49
ggggttgggg ttgcgccttt tccaaggcag ccctgggttt gcgcagggac gcggctgctc     60
tgggcgtggt tccgggaaac gcagcggcgc cgaccctggg tctcgcacat tcttcacgtc    120
cgttcgcagc gtcacccgga tcttcgccgc taccccttgtg ggcccccccgg cgacgcttcc    180
tgctccgccc ctaagtcggg aaggttcctt gcggttcgcg cgtgccggga cgtgacaaac    240
ggaagccgca cgtctcacta gtaccctcgc agacggacag cgcgcagggag caatggcagc    300
gcgccgaccg cgatgggctg tggccaatag cggctgctca gcagggcgcg ccgagagcag    360
cggccggaa ggggcggtgc gggaggcggg gtgtggggcg gtagtgtggg ccctgttcct    420
gcccgcgcgg tgttccgcat tctgcaagcc tccggagcgc acgtcggcag tcggctccct    480
cgttgaccga atcaccgacc tctctcccca g                                   511

SEQ ID NO: 50          moltype = DNA   length = 1162
FEATURE                Location/Qualifiers
source                 1..1162
                       mol_type = other DNA
                       organism = Homo sapiens
SEQUENCE: 50
gcgccgggtt ttggcgcctc ccgcgggcgc cccctcctc acggcgagcg ctgccacgtc      60
agacgaaggg cgcaggagcg ttcctgatcc ttccgcccgg acgctcagga cagcggcccg    120
ctgctcataa gactcggcct tagaacccca gtatcagcag aaggacattt taggacggga    180
cttgggtgac tctagggcac tggttttctt tccagagagc ggaacaggcg aggaaaagta    240
gtcccttctc ggcgattctg cggagggatc tccgtggggc ggtgaacgcc gatgattata    300
taaggacgcg ccgggtgtgg cacagctagt tccgtcgcag ccgggatttg ggtcgcggtt    360
cttgtttgtg gatcgctgtg atcgtcactt ggtgagttgc gggctgctgg gctggccggg    420
gctttcgtgg ccgccgggcc gctcggtggg acggaagcgt gtggagagac cgccaagggc    480
tgtagtctgg gtccgcgagc aaggttgccc tgaactgggg gttggggggga gcgcacaaaa    540
tggcggctgt tcccgagtct tgaatggaag acgcttgtaa ggcgggctgt gaggtcgttg    600
aaacaaggtg gggggcatgg tgggcggcaa gaacccaagg tcttgaggcc ttcgctaatg    660
cgggaaagct cttattcggg tgagatgggc tggggcacca tctgggggacc ctgacgtgaa    720
gtttgtcact gactggagaa ctcgggtttg tcgtctggtt gcgggggcgg cagttatgcg    780
gtgccgttgg gcagtgcacc cgtacctttg ggagcgcgcg cctcgtcgtg tcgtgacgtc    840
acccgttctg ttggcttata atgcagggtg gggccacctg ccggtaggtg tgcggtaggc    900
ttttctccgt cgcaggacgc agggttcggg cctagggtag gctctcctga atcgacaggc    960
gccggacctc tggtgagggg agggataagt gaggcgtcag tttctttggt cggttttatg   1020
tacctatctt cttaagtagc tgaagctccg gttttgaact atgcgctcgg ggttggcgag   1080
tgtgtttgt gaagttttt aggcacctt tgaaatgtaa tcatttgggt caatatgtaa   1140
ttttcagtgt tagactagta aa                                            1162

SEQ ID NO: 51          moltype = DNA   length = 120
FEATURE                Location/Qualifiers
source                 1..120
                       mol_type = other DNA
                       organism = Simian virus 40
SEQUENCE: 51
gtttattgca gcttataatg gttacaaata aagcaatagc atcacaaatt tcacaaataa     60
agcattttt tcactgcatt ctagttgtgg tttgtccaaa ctcatcaatg tatcttatca    120

SEQ ID NO: 52          moltype = DNA   length = 227
FEATURE                Location/Qualifiers
source                 1..227
                       mol_type = other DNA
                       organism = Bos taurus
SEQUENCE: 52
gactgtgcct tctagttgcc agccatctgt tgtttgcccc tccccgtgtgc cttccttgac      60
cctggaaggt gccactccca ctgtcctttc ctaataaaat gaggaaattg catcgcattg    120
tctgagtagg tgtcattcta ttctgggggg tgggtgggg caggacagca aggggggagga    180
ttgggaagac aatagcaggc atgctgggga tgcggtgggc tctatgg                  227

SEQ ID NO: 53          moltype = DNA   length = 1695
FEATURE                Location/Qualifiers
source                 1..1695
                       mol_type = other DNA
                       organism = Feline Endogenous Virus
SEQUENCE: 53
atgaaactcc caacaggaat ggtcatttta tgtagcctaa taatagttcg ggcagggttt     60
gacgacccc gcaaggctat cgcattagta caaaaacaac atggtaaacc atgcgaatgc    120
agcgagggc aggtatccga ggccccaccg aactccatcc aacaggtaac ttgcccaggc    180
aagacggcct acttaatgac caaccaaaaa tggaaatgca gagtcactcc aaaaaatctc    240
acccctagcg ggggagaact ccagaactgc ccctgtaaca ctttccagga ctcgatgcac    300
agttcttgtt atactgaata ccggcaatgc agggcgaata ataagacata ctacacggcc    360
```

```
accttgctta aaatacggtc tgggagcctc aacgaggtac agatattaca aaaccccaat  420
cagctcctac agtcccccttg taggggctct ataaatcagc ccgtttgctg gagtgccaca  480
gcccccatcc atatctccga tggtggagga cccctcgata ctaagagagt gtggacagtc  540
caaaaaaggc tagaacaaat tcataaggct atgcatcctg aacttcaata ccacccctta  600
gccctgccca aagtcagaga tgaccttagc cttgatgcac ggacttttga tatcctgaat  660
accactttta ggttactcca gatgtccaat tttagccttg cccaagattg ttggctctgt  720
ttaaaactag gtacccctac ccctcttgcg atacccactc cctctttaac ctactccta   780
gcagactccc tagcgaatgc ctcctgtcag attatacctc ccctcttggt tcaaccgatg  840
cagttctcca actcgtcctg tttatcttcc cctttcatta acgatacgga acaaatagac  900
ttaggtgcag tcacctttac taactgcacc tctgtagcca atgtcagtag tcctttatgt  960
gccctaaacg ggtcagtctt cctctgtgga aataacatgg catacaccta tttaccccaa  1020
aactggacag gactttgcgt ccaagcctcc ctcctcccc g acattgacat catcccgggg  1080
gatgagccag tccccattcc tgccattgat cattatatac atagacctaa acgagctgta  1140
cagttcatcc ctttactagc tggactggga atcaccgcag cattcaccac cggagctaca  1200
ggcctaggtg tctccgtcac ccagtataca aaattatccc atcagttaat atctgatgtc  1260
caagtcttat ccggtaccat acaagattta caagaccagg tagactcgtt agctgaagta  1320
gttctccaaa ataggagggg actggaccta ctaacggcag aacaaggagg aatttgttta  1380
gccttacaag aaaaatgctg tttttatgct aacaagtcag gaattgtgag aaacaaaata  1440
agaaccctac aagaagaatt acaaaaacgc agggaaagcc tggcatccaa ccctctctgg  1500
accgggctgc agggctttct tccgtacctc ctacctctcc tgggacccct actcaccctc  1560
ctactcatac taaccattgg gccatgcgtt ttcaatcgat tggtccaatt tgttaaagac  1620
aggatctcag tggtccaggc tctggttttg actcagcaat atcaccagct aaaacccata  1680
gagtacgagc catga                                                 1695
```

SEQ ID NO: 54          moltype = DNA  length = 2013
FEATURE                Location/Qualifiers
source                 1..2013
                       mol_type = other DNA
                       organism = Gibbon Ape Leukemia Virus
SEQUENCE: 54

```
atgcttctca cctcaagccc gcaccacctt cggcaccaga tgagtcctgg gagctggaaa  60
agactgatca tcctcttaag ctgcgtattc ggagacggca aaacgagtct gcagaataag  120
aacccccacc agcctgtgac cctcacctgg caggtactgt cccaaactgg ggacgttgtc  180
tgggacaaaa aggcagtcca gcccctttgg acttggtggc cctctcttac acctgatgta  240
tgtgccctgg cggccggtct tgagtcctgg gatatcccag gatccgatgt atcgtcctct  300
aaaagagtta gacctcctga ttcagactat actgccgctt ataagcaaat cacctgggga  360
gccatagggt gcagctaccc tcgggctagg accaggatgg caaattcccc cttctacgtg  420
tgtccccgag ctggccgaac ccattcagaa gctaggaggt gtggggggct agaatcccta  480
tactgtaaag aatggagttg tgagaccacg ggtaccgttt attggcaacc caagtcctca  540
tgggacctca taactgtaaa atgggaccaa aatgtgaaat gggagcaaaa atttcaaaag  600
tgtgaacaaa ccggctggtg taacccctc aagatagact tcacagaaaa aggaaaactc  660
tccagagatt ggataacgga aaaaacctgg gaattaaggt tctatgtata tggacaccca  720
ggcatacagt tgactatccg cttagaggtc actaacatgc cggttgtggc agtggggcca  780
gaccctgtcc ttgcggaaca gggacctcct agcaagcccc tcactctccc tctctcccca  840
cggaaagcgc cgcccacccc tctaccccg gcggctagtg agcaaacccc tgcggtgcat  900
ggagaaactg ttaccctaaa ctctccgcct cccaccagtg gcgaccgact ctttggcctt  960
gtgcagggg ccttcctaac cttgaatgct accaacccag gggccactaa gtcttgctgg  1020
ctctgtttgg gcatgagccc cccttattat gaagggatag cctcttcagg agaggtcgct  1080
tatacctcca accatacccg atgccactgg ggggcccaag aaaagcttac cctcactgag  1140
gtctccgac tcgggtcatg catagggaag gtgcctctta cccatcaaca tctttgcaac  1200
cagaccttac ccatcaattc ctctaaaaac catcagtatc tgctcccctc aaaccatagc  1260
tggtgggcct gcagcactgg cctcaccccc tgcctctcca cctcagtttt taatcagtc   1320
aaaagacttct gtgtccaggt ccagctgatc ccccgcatct attaccattc tgaagaaacc  1380
ttgttacaag cctatgacaa atcacccccc aggtttaaaa gagagcctgc ctcacttacc  1440
ctagctgtct tcctggggtt agggattgcg gcaggtatag gtactggctc aaccgcccta  1500
attaaagggc ccatagacct ccagcaaggc ctaaccagcc tccaaatcgc cattgacgct  1560
gacctccggg cccttcagga ctcaatcagc aagctagagg actcactgac ttccctatct  1620
gaggtagtac tccaaaatag gagaggcctt gacttactat tccttaaaga aggaggcctc  1680
tgcgcggccc taaaagaaga gtgctgtttt tatgtagacc actcaggtgc agtacgagac  1740
tccatgaaaa aacttaaaga aagcatagat aaaaagacagt tagagcgcca gaaaaaccaa  1800
aactggtatg aagggtggtt caataactcc ccttggttta ctaccctact atcaaccatc  1860
gctgggcccc tattgctcct ccttttgtta ctcactcttg ggcctgcat catcaataaa  1920
ttaatccaat tcatcaatga taggataagt gcagtcaaaa tttttagtcct tagacagaaa  1980
tatcagaccc tagataacga ggaaaaacctt taa                             2013
```

SEQ ID NO: 55          moltype = DNA  length = 1530
FEATURE                Location/Qualifiers
source                 1..1530
                       mol_type = other DNA
                       organism = Rabies virus
SEQUENCE: 55

```
atggttccgc aggttctttt gtttgtactc cttctgggtt tttcgttgtg tttcgggaag  60
ttccccattt acacgatacc agacgaactt ggtcctgga gccctattga catacaccat  120
ctcagctgtc caaataacct ggttgtggag gatgaaggat gtaccaacct gtccgagttc  180
tcctacatgg aactcaaagt gggatacatc tcagccatca agtgaacgg gttcacttgg  240
acaggtgttg tgcagagagc agagacctac accaactttg ttggttatgt cacaaccaca  300
ttcaagagaa agcatttccg ccccacccca gacgcatgta gagccgcgta taactggaag  360
atggccggta ccccagata tgaagagtcc ctacacaatc catccccga ctaccactgg  420
cttcgaactg taagaaccac caaagagtcc ctcattatca tatcccccaag tgtgacagat  480
```

```
ttggacccat atgacaaatc ccttcactca agggtcttcc ctggcggaaa gtgctcagga   540
ataacggtgt cctctaccta ctgctcaact aaccatgatt acaccatttg gatgcccgag   600
aatccgagac caaggacacc ttgtgacatt tttaccaata gcagaggaa gagagcatcc   660
aacgggaaca agacttgcgg ctttgtggat gaaagaggcc tgtataagtc tctaaaagga   720
gcatgcaggc tcaagttatg tggagttctt ggacttagac ttatggatgg aacatgggtc   780
gcgatgcaaa catcagatga gaccaaatgg tgccctccag atcagttggt gaatttgcac   840
gactttcgct cagacgagat cgagcatctc gttgtggagg agttagttaa gaaaagagag   900
gaatgtctgg atgcattaga gtccatcatg accaccaagt cagtaagttt cagacgtctc   960
agtcacctga gaaaacttgt cccagggttt ggaaaagcat ataccatatt caacaaaacc  1020
ttgatggagg ctgatgctca ctacaagtca gtccggacct ggaatgagat catcccctca  1080
aaagggtgtt tgaaagttgg aggaaggtgc catcctcatg tgaacggggt gttttttcaat 1140
ggtataatat tagggcctga cgaccatgtc ctaatcccag agatgcaatc atccctcctc  1200
cagcaacata tggagttgtt ggaatcttca gttatccccc tgatgcaccc cctggcagac  1260
ccttctacag ttttcaaaga aggtgatgag gctgaggatt ttgttgaagt tcacctcccc  1320
gatgtgtaca aacagatctc aggggttgac ctgggtctcc cgaactgggg aaagtatgta  1380
ttgatgactg caggggccat gattggcctg gtgttgatat tttccctaat gacatggtgc  1440
agagttggta tccatctttg cattaaatta aagcacacca agaaaagaca gatttataca  1500
gacatagaga tgaaccgact tggaaagtaa                                  1530
```

```
SEQ ID NO: 56         moltype = DNA  length = 1497
FEATURE               Location/Qualifiers
source                1..1497
                      mol_type = other DNA
                      organism = Lymphocytic Choriomeningitis Virus
SEQUENCE: 56
atgggtcaga ttgtgacaat gtttgaggct ctgcctcaca tcatcgatga ggtgatcaac   60
attgtcatta ttgtgcttat cgtgatcacg ggtatcaagg ctgtctacaa ttttgccacc  120
tgtgggatat tcgcattgat cagtttccta cttctggctg gcaggtcctg tggcatgtac  180
ggtcttaagg gacccgacat ttacaaagga gtttaccaat ttaagtcagt ggagtttgat  240
atgtcacatc tgaacctgac catgcccaac gcatgttcag caacaactc ccaccattac   300
atcagtatgg ggacttctgg actagaattg accttcacca atgattccat catcagtcac  360
aactttgca atctgacctc tgccttcaac aaaaagacct ttgaccacac actcatgagt  420
atagtttcga gcctacacct cagtatcaga gggaactcca actataaggc agtatcctgc  480
gacttcaaca atggcataac catccaatac aacttgacct tctcagatcg acaaagtgct  540
cagagccagt gtagaacctt cagaggtaga gtcctagata tgtttagaac tgccttcggg  600
gggaaataca tgaggagtgg ctggggctgg acaggctcag atggcaagac cacctggtgt  660
agccagacga gttaccaata cctgattata caaaatagaa cctgggaaaa ccactgcaca  720
tatgcaggtc cttttgggat gtccaggatt ctcctttccc aagagaagac taagttcttc  780
actaggagac tagcgggcac attcacctgg actttgtgac actcttcagg ggtggagaat  840
ccaggtggtt attgcctgac caaatggatg attcttgctg cagagcttaa gtgtttcggg  900
aacacagcag ttgcgaaatg caatgtaaat catgatgccg aattctgtga catgctgcga  960
ctaattgact acaacaaggc tgctttgagt aagttcaaag aggacgtaga atctgccttg 1020
cacttattca aaacaacagt gaattctttg atttcagatc aactactgat gaggaaccac 1080
ttgagagatc tgatggggggt gccatattgc aattactcaa agttttggta cctagaacat 1140
gcaaagaccg gcgaaactag tgtccccaag tgctggcttg tcaccaatgg ttcttactta 1200
aatgagaccc acttcagtga tcaaatcgaa caggaagccg ataacatgat tacagagatg 1260
ttgaggaagg attacataaa gaggcagggg agtaccccc tagcattgat ggaccttctg 1320
atgtttttcca catctgcata tctagtcagc atcttcctgc accttgtcaa aataccaaca 1380
cacaggcaca taaaaggtgg ctcatgtcca aagccacacc gattaaccaa caaaggaatt 1440
tgtagttgtg gtgcatttaa ggtgcctggt gtaaaaaccg tctggaaaag acgctga      1497
```

```
SEQ ID NO: 57         moltype = DNA  length = 1692
FEATURE               Location/Qualifiers
source                1..1692
                      mol_type = other DNA
                      organism = Fowl Plague virus
SEQUENCE: 57
atgaacactc aaatcctggt tttcgccctt gtggcagtca tccccacaaa tgcagacaaa   60
atttgtcttg gacatcatgc tgtatcaaat ggcaccaaag taaacacact cactgagaga  120
ggagtagaag ttgtcaatgc aacggaaaca gtggagcgga caaacatccc caaaatttgc  180
tcaaaaggga aaagaaccac tgatcttggc caatgcggac tgttagggac cattaccgga  240
ccacctcaat gcgaccaatt tctagaattt cagctgatc taataatcga gacgagaa      300
ggaaatgatg tttgttaccc ggggaagttt gttaatgaag aggcattgcg acaaatcctc  360
agagatcag gtgggattga caaagaaaca atgggattca catatagtgg aataaggacc  420
aacggaacaa ctagtgcatg tagaagatca gggtcttcat tctatgcaga aatggagtgt  480
ctcctgtcaa atacagacaa tgctgctttc ccacaaatga caaaatcata caaaaacaca  540
aggagagaat cagctctgat agtctgggga tccaccatt caggatcaac caccgaacag  600
accaaactat atgggagtgg aaataaaactg ataacagtcg ggagttccaa atatcatcaa  660
tcttttgtgc cgagtccagg aacacgaccg cagataaatg gccagtccgg acggattgat  720
tttcattggt tgatcttgga tcccaatgat acagttactt ttagtttcaa tgggggctttc  780
atagctccaa atcgtgccag cttcttgagg ggaaagtcca tggggatcca gagcgatgtg  840
caggttgatg ccaattgcga aggggaatgc taccacagtg agggactat aacaagcaga  900
ttgccttttc aaaacatcaa tagcagagca gttggcaaat gcccaagata tgtaaaacag  960
gaaagtttat tattggcaac tgggatgaag aacgttcccg aaccttccaa aaaaaggaaa 1020
aaaagaggcc tgtttggcgc tatagcaggg tttattgaaa atggttggga aggtctggtc 1080
gacgggtggt acggttttcag gcatcagaat gcacaaggag aaggaactgc agcagactac 1140
aaaagcaccc aatcggcaat tgatcagata accggaaagt aaatagact cattgagaaa  1200
accaaccagc aatttgagct aatagataat gaattcactg aggtggaaaa gcagattggc 1260
aatttaatta actggaccaa agactccatc acagaagtat ggtcttacaa tgctgaactt 1320
```

-continued

```
cttgtggcaa tggaaaacca gcacactatt gatttggctg attcagagat gaacaagctg   1380
tatgagcgag tgaggaaaca attaaggaa aatgctgaag aggatggcac tggttgcttt   1440
gaaattttc ataaatgtga cgatgattgt atggctagta taaggaacaa tacttatgat   1500
cacagcaaat acagagaaga agcgatgcaa aatagaatac aaattgaccc agtcaaattg   1560
agtagtggct acaaagatgt gatactttgg tttagcttcg gggcatcatg cttttttgctt   1620
cttgccattg caatgggcct tgttttcata tgtgtgaaga acggaaacat gcggtgcact   1680
atttgtatat aa                                                         1692

SEQ ID NO: 58            moltype = DNA  length = 1266
FEATURE                  Location/Qualifiers
source                   1..1266
                         mol_type = other DNA
                         organism = Ross River Virus
SEQUENCE: 58
agtgtaacag agcactttaa tgtgtataag gctactagac catacctagc acattgcgcc    60
gattgcgggg acgggtactt ctgctatagc ccagttgcta tcgaggagat ccagatgag    120
gcgtctgatg gcatgcttaa gatccaagtc tccgcccaaa taggtctgga caaggcaggc   180
acccacgccc acacgaagct ccgatatatg gctggtcatg atgttcagga atctaagaga   240
gattccttga gggtgtacac gtccgcagcg tgctccatac atgggacgat gggacacttc   300
atcgtcgcac actgtccacc aggcgactac ctcaaggttt cgttcgagga cgcagattcg   360
cacgtgaagg catgtaaggt ccaatacaag cacaatccat gccggtgggg tagagagaag   420
ttcgtggtta gaccacactt tggcgtagag ctgccatgca cctcatacca gctgacaacg   480
gctcccaccg acgaggagat tgacatgcat acaccgccag atataccgga tcgcaccctg   540
ctatcacaga cggcgggcaa cgtcaaaata acagcaggcg gcaggactat caggtacaac   600
tgtacctgcg gccgtgacaa cgtaggcact accagtactg acaagaccat caacacatgc   660
aagattgacc aatgccatgc tgccgtcacc agccatgaca aatggcaatt tacctctcca   720
tttgttccca gggctgatca gacagctagg aaaggcaagg tacacgttcc gttccctctg   780
actaacgtca cctgccgagt gccgttggct cgagcgccgg atgccaccta tggtaagaag   840
gaggtgaccc tgagattaca cccagatcat ccgacgctct tctcctatag gagtttagga   900
gccgaaccgc acccgtacga ggaatgggtt gacaagttct ctgagcgcat catcccagtg   960
acggaagaag ggattgagta ccagtggggc aacaacccgc cggtctgcct gtgggcgcaa   1020
ctgacgaccg agggcaaacc ccatggctgg ccacatgaaa tcattcagta ctattatgga   1080
ctataccccg ccgccactat tgccgcagta tccggggcga gtctgatggc cctcctaact   1140
ctggcggcca catgctgcat gctggccacc gcgaggagaa agtgcctaac accgtacgcc   1200
ctgacgccag gagcggtggt accgttgaca ctggggctgc tttgctgcgc accgagggcg   1260
aatgca                                                               1266

SEQ ID NO: 59            moltype = DNA  length = 1266
FEATURE                  Location/Qualifiers
source                   1..1266
                         mol_type = other DNA
                         organism = Murine Leukemia virus
SEQUENCE: 59
agtgtaacag agcactttaa tgtgtataag gctactagac catacctagc acattgcgcc    60
gattgcgggg acgggtactt ctgctatagc ccagttgcta tcgaggagat ccagatgag    120
gcgtctgatg gcatgcttaa gatccaagtc tccgcccaaa taggtctgga caaggcaggc   180
acccacgccc acacgaagct ccgatatatg gctggtcatg atgttcagga atctaagaga   240
gattccttga gggtgtacac gtccgcagcg tgctccatac atgggacgat gggacacttc   300
atcgtcgcac actgtccacc aggcgactac ctcaaggttt cgttcgagga cgcagattcg   360
cacgtgaagg catgtaaggt ccaatacaag cacaatccat gccggtgggg tagagagaag   420
ttcgtggtta gaccacactt tggcgtagag ctgccatgca cctcatacca gctgacaacg   480
gctcccaccg acgaggagat tgacatgcat acaccgccag atataccgga tcgcaccctg   540
ctatcacaga cggcgggcaa cgtcaaaata acagcaggcg gcaggactat caggtacaac   600
tgtacctgcg gccgtgacaa cgtaggcact accagtactg acaagaccat caacacatgc   660
aagattgacc aatgccatgc tgccgtcacc agccatgaca aatggcaatt tacctctcca   720
tttgttccca gggctgatca gacagctagg aaaggcaagg tacacgttcc gttccctctg   780
actaacgtca cctgccgagt gccgttggct cgagcgccgg atgccaccta tggtaagaag   840
gaggtgaccc tgagattaca cccagatcat ccgacgctct tctcctatag gagtttagga   900
gccgaaccgc acccgtacga ggaatgggtt gacaagttct ctgagcgcat catcccagtg   960
acggaagaag ggattgagta ccagtggggc aacaacccgc cggtctgcct gtgggcgcaa   1020
ctgacgaccg agggcaaacc ccatggctgg ccacatgaaa tcattcagta ctattatgga   1080
ctataccccg ccgccactat tgccgcagta tccggggcga gtctgatggc cctcctaact   1140
ctggcggcca catgctgcat gctggccacc gcgaggagaa agtgcctaac accgtacgcc   1200
ctgacgccag gagcggtggt accgttgaca ctggggctgc tttgctgcgc accgagggcg   1260
aatgca                                                               1266

SEQ ID NO: 60            moltype = DNA  length = 2030
FEATURE                  Location/Qualifiers
source                   1..2030
                         mol_type = other DNA
                         organism = Ebola virus
SEQUENCE: 60
atgggtgtta caggaatatt gcagttacct cgtgatcgat tcaagaggac atcattcttt    60
ctttgggtaa ttatcctttt ccaaagaaca ttttccatcc cacttggagt catcccacaat   120
agcacattac aggttagtga tgtcgacaaa ctggtttgcc gtgacaaact gtcatccaca   180
aatcaattga gatcagttgg actgaatctc aagggaatg gagtggcaac tgacgtgcca   240
tctgcaacta aaagatgggg cttcaggtcc ggtgtcccac caaggtggt caattatgaa   300
gctggtgaat gggctgaaaa actgctacaat cttgaaatca aaaaacctga cgggagtgag   360
tgtctaccag cagcgccaga cgggattcgg ggcttccccc ggtgccggta tgtgcacaaa   420
```

-continued

```
gtatcaggaa cgggaccgtg tgccggagac tttgccttcc acaaagaggg tgctttcttc  480
ctgtatgacc gacttgcttc cacagttatc taccgaggaa cgactttcgc tgaaggtgtc  540
gttgcatttc tgatactgcc ccaagctaag aaggacttct tcagctcaca ccccttgaga  600
gagccggtca atgcaacgga ggacccgtct agtggctact attctaccac aattagatat  660
caagctaccg gttttggaac caatgagaca gagtatttgt tcgaggttga caatttgacc  720
tacgtccaac ttgaatcaag attcacacca cagtttctgc tccagctgaa tgagacaata  780
tatacaagtg ggaaaaggag caataccacg ggaaaactaa tttggaaggt caaccccgaa  840
attgatacaa caatcgggga gtgggccttc tgggaaacta aaaaaacctc actagaaaaa  900
ttcgcagtga agagttgtct ttcacagctg tatcaaacag agccaaaaac atcagtggtc  960
agagtccggc gcgaacttct tccgacccag ggaccaacac aacaactgaa gaccacaaaa  1020
tcatggcttc agaaaattcc tctgcaatgg ttcaagtgca cagtcaagga agggaagctg  1080
cagtgtcgca tctgacaacc cttgccacaa tctccacgag tcctcaaccc cccacaacca  1140
aaccaggtcc ggacaacagc acccacaata cacccgtgta taaacttgac atctctgagg  1200
caactcaagt tgaacaacat caccgcagaa cagacaacga cagcacagcc tccgacactc  1260
cccccgccac gaccgcagcc ggacccctaa aagcagagaa caccaacacg agcaagggta  1320
ccgacctcct ggaccccgcc accacaacaa gtccccaaaa ccacagcgag accgctggca  1380
acaacaacac tcatcaccaa gataccggag aagagagtgc cagcagcggg aagctaggct  1440
taattaccaa tactattgct ggagtcgcag gactgatcac aggcgggagg agagctcgaa  1500
gagaagcaat tgtcaatgct caacccaaat gcaaccctaa tttacattac tggactactc  1560
aggatgaagg tgctgcaatc ggactggcct ggataccata tttcgggcca gcagccgagg  1620
gaatttacat agagggggctg atgcacaatc aagatggttt aatctgtggg ttgagacagc  1680
tggccaacga gacgactcaa gctcttcaac tgttcctgag agccacaacc gagctacgca  1740
ccttttcaat cctcaaccgt aaggcaattg atttcttgct gcagcgatgg ggcggcacat  1800
gccacatttt gggaccggac tgctgtatcg aaccacatga ttggaccaag aacataacag  1860
acaaaattga tcagattatt catgattttg ttgataaaac ccttccggac caggggggaca  1920
atgacaattg gtggacagga tggagacaat ggataccggc aggtattgga gttacaggcg  1980
ttataattgc agttatcgct ttattctgta tatgcaaatt tgtcttttag              2030
```

```
SEQ ID NO: 61          moltype = DNA  length = 49
FEATURE                Location/Qualifiers
misc_feature           1..49
                       note = Control shRNA sequence
source                 1..49
                       mol_type = other DNA
                       organism = synthetic construct
SEQUENCE: 61
gccgctttgt aggatagagc tcgagctcta tcctacaaag cggcttttt               49
```

VIRAL VECTORS FOR TREATING PARKINSON'S DISEASE

CROSS-REFERENCE TO RELATED APPLICATIONS

This application is a Divisional application of U.S. patent application Ser. No. 16/318,345, filed on Jan. 16, 2019, which is a U.S. national phase filing under 35 U.S.C. § 371 of PCT/US2017/043157 filed on Jul. 20, 2017, entitled "VIRAL VECTORS FOR TREATING PARKINSON'S DISEASE," which claims priority to U.S. Provisional Patent Application No. 62/365,316 filed on Jul. 21, 2016 entitled "VIRAL VECTORS FOR TREATING PARKINSON'S DISEASE," the disclosures of which are incorporated herein by reference.

SEQUENCE LISTING

A Sequence Listing in compliance with 37 CFR 1.831-1.834 is submitted herewith and is incorporated by reference. The Sequence Listing in .xml format includes no new matter. The Sequence Listing is supported throughout the application as filed and all sequences are listed on pages 35-56. The name of the file is 436313000817 SL and the file size is 94 kb.

FIELD

Aspects of the invention relate to using vectors to treat Parkinson's disease. More specifically, aspects of the invention relate to using lentiviral vectors, including PARP-containing lentiviral vectors, to treat Parkinson's disease.

BACKGROUND

Parkinson's disease ("PD") is the second most common neurodegenerative disorder in the United States. Approximately 1 million Americans are afflicted with PD, with more than 60,000 new cases diagnosed each year. See, e.g., Fahn, S., 991 *Ann. N.Y. Acad. Sci.* 1-14 (2003). The incidence is expected to double by 2030. See, e.g., Dorsey, E. R., et al., 68(5) *Neurology*, 384-6 (2007). PD is a chronic progressive condition that generally appears late in life. PD is caused by the degeneration and death of dopamine producing neurons in the substantia nigra region of the basal ganglia. The deteriorated neurons and reduced dopamine result in abnormal neural activity and a chronic, progressive deterioration of motor function control. Patients with PD suffer from significant quality-of-life issues due to symptoms that include bradykinesia, rigidity, tremor, and postural instability. Additional complications due to PD include non-motor symptoms, such as dysphagia, and neuropsychiatric effects. See, e.g., Weintraub, D. et al., 14(2 Suppl) *Am. J. Manag. Care*, S40-8 (2008).

PD can be treated with L-DOPA or dopamine agonists, but there are significant side effects and the continuous neuronal death results in an increasing requirement for L-DOPA or dopamine agonists. Gene therapy has the potential to modify the behavior of neurons in the substantia nigra. Consequently, gene therapy has been considered as a possibility for effectively treating PD.

Initial clinical studies on PD gene therapy attempted to increase dopamine production in the substantia nigra by elevating the level of dopamine-synthesizing enzymes, particularly aromatic L-amino acid decarboxylase (AADC). Adeno-associated viral vectors (AAV) carrying the complementary DNA sequence for AADC were injected into the substantia nigra of patients afflicted with PD. In one study, delivery of AADC using adeno-associated virus (AAV) was well tolerated, but the clinical outcomes trended to only modest improvement. See, e.g., Eberling et al., 70(21) *Neurology*, 1989-93 (2008). After longer (e.g., 4-year) follow-up, the clinical impact was largely lost, and it was concluded that the dosing was insufficient for sustained clinical improvement.

An alternate approach sought to treat PD using gene therapy to increase expression of neurturin, a neurotrophic growth factor, in the substantia nigra. Results from AAV delivery of the neurturin gene to the brains of patients afflicted with PD showed no improvement over sham controls. See, e.g., Marks Jr. et al., 9(12) *Lancet Neurol.*, 1164-72 (2010).

Gene therapy trials designed to increase dopamine production or provide neurotrophic growth factors have not provided a significant, durable objective clinical response in patients with PD. See, e.g., Eberling et al., supra. Part of the reason why treatment for PD is complex and challenging is that disease progression is due to the accelerated death of dopaminergic neurons that eventually reduces dopamine below survivable levels.

Accordingly, current treatments for PD symptoms include drugs, ablative surgical intervention, and neural stimulation.

SUMMARY

In an aspect of the present disclosure, a lentiviral vector system is provided for expressing a lentiviral particle. The system includes a therapeutic vector which encodes a short hairpin RNA ("shRNA") for inhibiting Poly(ADP-ribose) polymerase ("PARP") expression. The system also includes an envelope plasmid comprising a neuron-specific sequence for targeting the shRNA to a neuron; and at least one helper plasmid comprising gag, pol, and rev genes. When the therapeutic vector, the envelope plasmid, and the at least one helper plasmid are transfected into a packaging cell line, a neuron-specific lentiviral particle optimized for inhibiting PARP expression is produced by the packaging cell line.

In embodiments, the shRNA comprises a PARP-specific shRNA. In embodiments, the shRNA comprises a PARP1-specific shRNA. In embodiments, the shRNA comprises at least 80% sequence identity with any one of SEQ ID NOs: 6-10. In embodiments, the shRNA comprises a shRNA having at least 85% sequence identity with any one of SEQ ID NOs: 6-10. In embodiments, the shRNA comprises a shRNA having at least 90% sequence identity with any one of SEQ ID NOs: 6-10. In embodiments, the shRNA comprises a shRNA having at least 95% sequence identity with any one of SEQ ID NOs: 6-10. In embodiments, the shRNA comprises any one of SEQ ID NOs: 6-10.

In embodiments, the shRNA comprises a shRNA having at least 80% sequence identity with any one of SEQ ID NOs: 16-20. In embodiments, the shRNA comprises a shRNA having at least 85% sequence identity with any one of SEQ ID NOs: 16-20. In embodiments, the shRNA comprises a shRNA having at least 90% sequence identity with any one of SEQ ID NOs: 16-20. In embodiments, the shRNA comprises a shRNA having at least 95% sequence identity with any one of SEQ ID NOs: 16-20. In embodiments, the shRNA comprises any one of SEQ ID NOs: 16-20. In embodiments, the neuron-specific sequence encodes VSV-G, FUG-C, or gp64, or a variant thereof. Optionally, the neuron-specific sequence encodes only VSV-G, or a variant thereof. The neuron-specific sequence may encode a protein that improves transduction into a neuron. The neuron-specific sequence may encode a protein that improves transduction into a neuron expressing tyrosine hydroxylase (TH+).

In another aspect, a method of treating a subject suffering from Parkinson's disease is disclosed. The method involves administering to the subject a therapeutic vector comprising a shRNA for inhibiting PARP expression; an envelope plasmid comprising a neuron-specific sequence for targeting the shRNA to a neuron; and at least one helper plasmid comprising gag, pol, and rev genes. When the therapeutic vector, the envelope plasmid, and the at least one helper plasmid are transfected into at least one packaging cell, a neuron-specific lentiviral particle optimized for inhibiting PARP expression is produced by the packaging cell, and lentiviral particle is administered to the subject in need thereof. In embodiments, the lentiviral particle transduces a host cell to deliver the PARP shRNA. In embodiments, the shRNA comprises a PARP-specific shRNA. In embodiments, the shRNA comprises a PARP1-specific shRNA. In embodiments, the shRNA comprises a shRNA having at least 80% sequence identity with any one of SEQ ID NOs: 6-10. In embodiments, the shRNA comprises a shRNA having at least 85% sequence identity with any one of SEQ ID NOs: 6-10. In embodiments, the shRNA comprises a shRNA having at least 90% sequence identity with any one of SEQ ID NOs: 6-10. In embodiments, the shRNA comprises a shRNA having at least 95% sequence identity with any one of SEQ ID NOs: 6-10. In embodiments, the shRNA comprises any one of SEQ ID NOs: 6-10. In embodiments, the shRNA comprises a shRNA having at least 80% sequence identity with any one of SEQ ID NOs: 16-20. In embodiments, the shRNA comprises a shRNA having at least 85% sequence identity with any one of SEQ ID NOs: 16-20. In embodiments, the shRNA comprises a shRNA having at least 90% sequence identity with any one of SEQ ID NOs: 16-20. In embodiments, the shRNA comprises a shRNA having at least 95% sequence identity with any one of SEQ ID NOs: 16-20. In embodiments, the shRNA comprises any one of SEQ ID NOs: 16-20. The neuron-specific sequence may encode VSV-G, FUG-C, or gp64, or variants thereof. The neuron-specific sequence may encode only VSV-G, or variants thereof. The neuron-specific sequence may encode a protein that improves transduction into a neuron of the subject. The neuron-specific sequence may encode a protein that improves transduction into a neuron expressing tyrosing hydroxylase (TH+) of the subject.

In another aspect, a method of treating a subject suffering from Parkinson's disease is disclosed. The method involves administering to the subject a therapeutically effective amount of a lentiviral particle expressed by the lentiviral vector system as described herein. The method may also include a second therapeutic regimen. The second therapeutic regimen may include ablative surgical intervention, neural stimulation, L-DOPA administration, or dopamine agonist administration.

In another aspect, use of a therapeutic vector, an envelope plasmid, and at least one helper plasmid is disclosed for treating a subject suffering from Parkinson's disease. The therapeutic vector includes a shRNA to inhibit PARP expression. The envelope plasmid includes a neuron-specific sequence to target the shRNA to a neuron. One or more helper plasmids include at least one or more of a gag, pol, or rev gene.

By suppressing PARP levels, the lentiviral vector system disclosed herein reduces rates for neuronal death, preserves the capacity for normal dopamine production and delay or prevent the onset of Parkinson's disease. The lentiviral vector system disclosed herein, unlike AAVs, has a higher capacity for transducing resting cells, can be optimized to efficiently transduce neurons, and can generate a permanent modification by inserting a transgene into cellular DNA. Additionally, the lentiviral vector system disclosed herein is less inflammatory than AAVs, which allows for greater dose escalation, and allows for greater flexibility in vector design when testing for alternate envelope glycoproteins, vector composition, doses, and associated delivery methods.

Other aspects and advantages of the inventions described herein will become apparent from the following detailed description, taken in conjunction with the accompanying drawings, which illustrate by way of example the aspects of the inventions.

DETAILED DESCRIPTION

Overview of the Disclosure

Figure 1A:
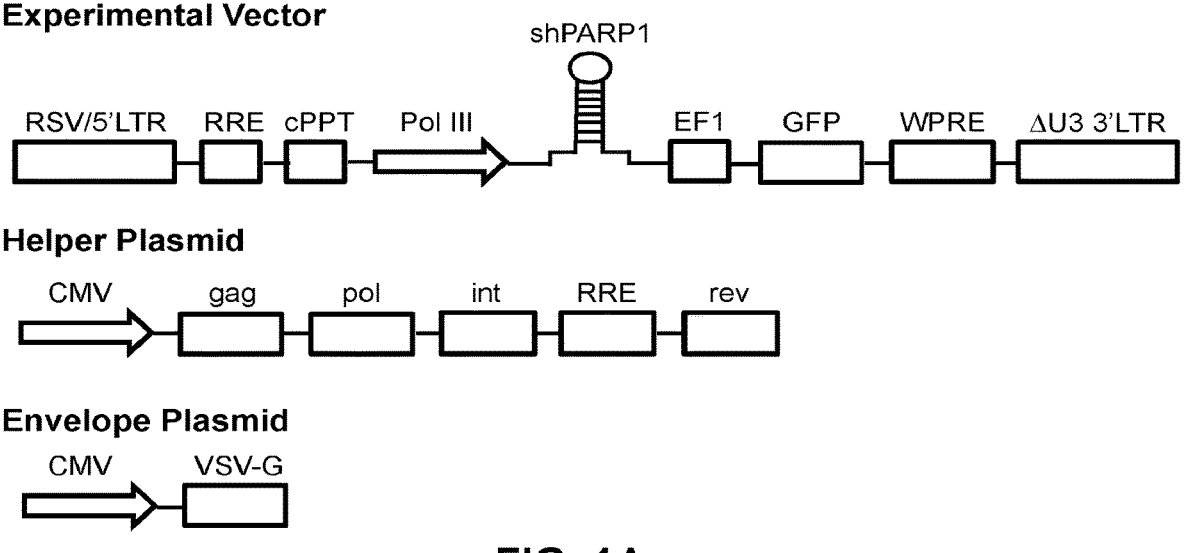
FIG. 1A depicts an exemplary lentiviral vector system comprised of an experimental therapeutic vector, an envelope plasmid, and a helper plasmid. The experimental therapeutic vector detailed in FIG. 1A contains GFP.
Figure 1B:
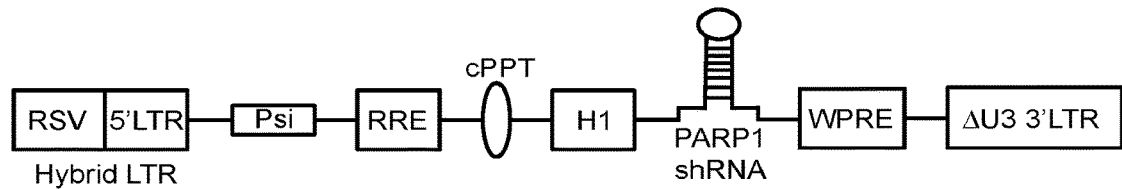
FIG. 1B depicts an exemplary therapeutic vector designed to reduce expression of PARP1 in substantia nigra neurons in patients afflicted with PD. The therapeutic vector detailed in FIG. 1B does not contain GFP.

Aspects of the present invention describe the development of a lentiviral vector system for treating PD. The lentiviral vector system includes a therapeutic vector that includes an inhibitory RNA construct for reducing the expression of PARP. The PARP1 protein has been implicated for its role in PD.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described Gherein are those well-known and commonly used in the art. The methods and techniques of the present disclosure are generally performed according to conventional methods well-known in the art and as described in various general and more specific references that are cited and discussed throughout the present specification unless otherwise indicated. See, e.g.: Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual; Cold Spring Harbor Laboratory Press, Cold Spring Harbor, N.Y. (1998); and Coligan et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

As used herein, the term "includes" means includes without limitation.

As used herein, the term "lentiviral vector" is synonymous with the term "therapeutic vector." The term "experimental therapeutic vector" means a therapeutic vector that includes an experimental feature such as GFP.

As used herein, the term "miRNA" means a microRNA.

As used herein, the term "packaging cell line" refers to any cell line that can be used to express a lentiviral particle.

As used herein, the term "Parkinson's disease," which is also referred to herein as "PD," refers to the known neurodegenerative disease, as well as all symptoms related thereto.

Treatment of "Parkinson's disease," therefore, may relate to treatment of all or some of the symptoms associated with Parkinson's disease.

As used herein, the term "PARP" stands for poly ADP ribose polymerase and includes all PARP-family members, and includes the specific PARP-family member, PARP1 (accession number NM_001618.3) and variants thereof.

The term "percent identity," which is also referred to herein as "sequence identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J Mol. Biol. 48:443 (1970), by the search for similarity method of Pearson & Lipman, Proc. Natl. Acad. Sci. U.S.A. 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J Mol. Biol. 215:403-410 (1990). Software for performing BLAST analyses is publicly available through the National Center for Biotechnology Information website.

The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (Version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package (available at www.gcg-.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and/or protein sequences of the present disclosure can further be used as a "query sequence" to perform a search against public databases to, for example, identify related sequences. Such searches can be performed using the NBLAST and XBLAST programs (version 2.0) of Altschul et al. (1990) J Mol. Biol. 215:403-10. BLAST nucleotide searches can be performed with the NBLAST program, score=100, word length=12 to obtain nucleotide sequences homologous to the nucleic acid molecules provided in the disclosure. BLAST protein searches can be performed with the XBLAST program, score=50, word-length=3 to obtain amino acid sequences homologous to the protein molecules of the disclosure. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See www.ncbi.nlm.nih.gov.

As used herein, the term "plasmid" is synonymous with the term "vector."

As used herein, the term "SEQ ID NO" is synonymous with the term "Sequence ID No."

As used herein, the term "shRNA" refers to a short hairpin RNA.

As used herein, the term "subject" includes a human patient but also includes other mammals.

As used herein, the term "TH" refers to tyrosine hydroxylase.

Description of Aspects of the Disclosure

In an aspect of the disclosure, the present disclosure provides a lentiviral vector system for expressing a lentiviral particle. The system includes a therapeutic vector which includes a shRNA for inhibiting PARP-family member expression. There are numerous PARP family members and this disclosure is not limited to any one particular PARP-family member. However, in embodiments, the lentiviral vector system specifically inhibits PARP1.

The system includes at least one helper plasmid comprising at least one of a gag, pol, or rev gene. Each of the gag, pol and rev genes may be provided on individual plasmids, or one or more genes may be provided together on the same plasmid. In embodiments, the gag, pol, and rev genes are provided on the same plasmid (e.g., FIG. 1C). In embodiments, the gag and pol genes are provided on a first plasmid and the rev gene is provided on a second plasmid (e.g., FIG. 1D). In further embodiments, 3-vector and 4-vector systems are provided herein.

As detailed herein, the therapeutic vector, the envelope plasmid and at least one helper plasmid are transfected into a packaging cell line. A non-limiting example of a packaging cell line is the 293T/17 HEK cell line. When the therapeutic vector, the envelope plasmid, and at least one helper plasmid are transfected into the packaging cell line, a lentiviral particle is produced. Under the experimental conditions described herein, the lentiviral particle produced by the lentiviral vector system can be a neuron-specific lentiviral particle which is optimized for inhibiting PARP expression.

In embodiments, the shRNA comprises a PARP-specific shRNA. In embodiments, the shRNA comprises a PARP1-specific shRNA. In embodiments, the shRNA comprises a shRNA having at least 80%, or at least 81%, or at least 82%, or at least 83%, or at least 84% sequence identity with any one of SEQ ID NOs: 6-10. In embodiments, the shRNA comprises a shRNA having at least 85%, or at least 86%, or at least 87%, or at least 88%, or at least 89% sequence identity with any one of SEQ ID NOs: 6-10. In embodiments, the shRNA comprises a shRNA having at least 90%, or at least 91%, or at least 92%, or at least 93%, or at least 94% sequence identity with any one of SEQ ID NOs: 6-10. In embodiments, the shRNA comprises a shRNA having at least 95%, or at least 96%, or at least 97%, or at least 98%, or at least 99% with any one of SEQ ID NOs: 6-10. In embodiments, the shRNA comprises any one of SEQ ID NOs: 6-10.

In embodiments, the shRNA comprises a shRNA having at least 80%, or at least 81%, or at least 82%, or at least 83%, or at least 84% sequence identity with any one of SEQ ID NOs: 16-20. In embodiments, the shRNA comprises a shRNA having at least 85%, or at least 86%, or at least 87%, or at least 88%, or at least 89% sequence identity with any one of SEQ ID NOs: 16-20. In embodiments, the shRNA comprises a shRNA having at least 90%, or at least 91%, or at least 92%, or at least 93%, or at least 94% sequence identity with any one of SEQ ID NOs: 16-20. In embodiments, the shRNA comprises a shRNA having at least 95%, or at least 96%, or at least 97%, or at least 98%, or at least 99% sequence identity with any one of SEQ ID NOs: 16-20. In embodiments, the shRNA comprises any one of SEQ ID NOs: 16-20. In embodiments, any of the foregoing shRNAs can be replaced with a suitable miRNA. In embodiments, the neuron-specific sequence encodes VSV-G, FUG-C, or gp64 or any other sequence that confers tropic specificity to neuron cells. Optionally, the neuron-specific sequence encodes only VSV-G. In embodiments, the neuron-specific sequence encodes a protein that improves transduction into a neuron. In embodiments, the neuron-specific sequence encodes a protein that improves transduction into a TH+ neuron.

In another aspect of the disclosure, a method of treating a subject suffering from PD is disclosed. In embodiments, the subject is a human being afflicted with mild, moderate, or severe PD. In embodiments, the subject is a human being afflicted with any symptom commonly or uncommonly associated with PD.

The method involves administering to the subject a lentiviral therapeutic vector comprising a shRNA for inhibiting PARP expression. In embodiments, the lentiviral vector is packaged as a lentiviral particle that transduces a host cell to deliver the PARP shRNA.

In embodiments, the shRNA comprises a PARP-specific shRNA. In embodiments, the shRNA comprises a PARP1-specific shRNA. In embodiments, the shRNA comprises a shRNA having at least 80%, or at least 81%, or at least 82%, or at least 83%, or at least 84% sequence identity with any one of SEQ ID NOs: 6-10. In embodiments, the shRNA comprises a shRNA having at least 85%, or at least 86%, or at least 87%, or at least 88%, or at least 89% sequence identity with any one of SEQ ID NOs: 6-10. In embodiments, the shRNA comprises a shRNA having at least 90%, or at least 91%, or at least 92%, or at least 93%, or at least 94% sequence identity with any one of SEQ ID NOs: 6-10. In embodiments, the shRNA comprises a shRNA having at least 95%, or at least 96%, or at least 97%, or at least 98%, or at least 99% sequence identity with any one of SEQ ID NOs: 6-10. In embodiments, the shRNA comprises any one of SEQ ID NOs: 6-10.

In embodiments, the shRNA comprises a shRNA having at least 80%, or at least 81%, or at least 82%, or at least 83%, or at least 84% sequence identity with any one of SEQ ID NOs: 16-20. In embodiments, the shRNA comprises a shRNA having at least 85%, or at least 86%, or at least 87%, or at least 88%, or at least 89% sequence identity with any one of SEQ ID NOs: 16-20. In embodiments, the shRNA comprises a shRNA having at least 90%, or at least 91%, or at least 92%, or at least 93%, or at least 94% sequence identity with any one of SEQ ID NOs: 16-20. In embodiments, the shRNA comprises a shRNA having at least 95%, or at least 96%, or at least 97%, or at least 98%, or at least 99% sequence identity with any one of SEQ ID NOs: 16-20. In embodiments, the shRNA comprises any one of SEQ ID NOs: 16-20. In embodiments, any of the foregoing shRNAs can be replaced with a suitable miRNA. In embodiments, the neuron-specific sequence encodes VSV-G, FUG-C, or gp64 or any other sequence that confers tropic specificity to neuron cells. Optionally, the neuron-specific sequence encodes only VSV-G. In embodiments, the neuron-specific sequence encodes a protein that improves transduction into a neuron of the subject. In embodiments, the neuron-specific sequence encodes a protein that improves transduction into a TH+ neuron of the subject.

In another aspect, a method of treating a subject suffering from PD is disclosed. The method involves administering to the subject a therapeutically effective amount of a lentiviral particle expressed by the lentiviral vector system as described herein. In embodiments, the method includes a second therapeutic regimen. In embodiments, the second therapeutic regimen includes, but is not limited to: ablative surgical intervention, neural stimulation, L-DOPA administration, dopamine agonist administration, or any other known Parkinson's disease treatment. In embodiments, the system disclosed herein can be used to treat PD while eliminating the need for increasing doses of L-DOPA.

Lentiviral Vector System

A lentiviral virion (particle) is expressed by a vector system encoding the necessary viral proteins to produce a virion (viral particle). There is at least one vector containing a nucleic acid sequence encoding the lentiviral pol proteins necessary for reverse transcription and integration, operably linked to a promoter. In another embodiment, the pol proteins are expressed by multiple vectors.

In another aspect, use of a therapeutic vector, an envelope plasmid, and at least one helper plasmid is disclosed for treating a subject suffering from PD. The therapeutic vector includes a shRNA to inhibit PARP expression. In embodiments, the envelope plasmid includes a neuron-specific sequence to target the shRNA to a neuron and at least one helper plasmid that includes gag, pol, and rev genes.

By suppressing PARP levels, the lentiviral vector system disclosed herein will reduce rates for neuronal death, preserve the capacity for normal dopamine production and delay and/or prevent the onset of PD. The lentiviral vector system disclosed herein, unlike AAV systems known in the art, has a higher capacity for transducing resting cells, can be optimized to efficiently transduce neurons, and can generate a permanent modification by inserting a transgene into cellular DNA. Additionally, the lentiviral vector system disclosed herein is less inflammatory than AAV systems, which allows for greater dose escalation, and allows for greater flexibility in vector design when testing for alternate envelope glycoproteins, vector composition, doses and associated delivery methods.

The disclosed lentiviral vector system can be optimized for short, medium, or long-term suppression of PARP expression in subjects afflicted with PD. Accordingly, dosing regimens may vary based upon the severity of the PD, or the associated PD symptoms. The lentiviral particles disclosed herein may be administered to a subject in need thereof in varying doses. A subject may be administered $\geq 10^6$ transducing units of lentiviral particle suspension (where 1 dose is needed on average to transduce 1 target cell). A subject may be administered $\geq 10^6$, $\geq 10^7$, $\geq 10^1$, $\geq 10^9$, or $\geq 10^{10}$ transducing units. Upper dosing limits will be determined by a variety of factors understood by those persons skilled in the art.

The vector(s) forming the lentiviral particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment, the env nucleic acid sequence encodes a lentiviral envelope protein.

In another embodiment, the envelope protein is not from the lentivirus, but from a different virus. The resultant particle is referred to as a pseudotyped particle. By appropriate selection of envelopes one can "infect" virtually any cell. For example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus, hepatitis C virus, GB virus), rhabdoviruses (vesicular stomatitis virus, rabies virus), paramyxoviruses (mumps or measles), picornaviruses (Mengo, Polio, and Coxsackie), and orthomyxoviruses (influenza virus). Other envelopes that can preferably be used include those from Moloney Leukemia Virus such as MLV-E, MLV-A and GALV. These latter envelopes are particularly preferred where the host cell is a primary cell. Other envelope proteins can be selected depending upon the desired host cell. For example, targeting specific receptors such as a dopamine receptor can be used for brain delivery. Another target can be vascular endothelium. These cells can be targeted using a filovirus envelope. For example, the GP of Ebola, which by post-transcriptional modification become the GP, and GP$_2$ glycoproteins. In another embodiment, one can use different lentiviral capsids with a pseudotyped envelope (for example, FIV or SHIV [U.S. Pat. No. 5,654,195]). A SHIV pseudotyped vector can readily be used in animal models such as monkeys.

As detailed herein, a lentiviral vector system typically includes at least one helper plasmid comprising at least one of a gag, pol, or rev gene. Each of the gag, pol and rev genes may be provided on individual plasmids, or one or more genes may be provided together on the same plasmid. In one embodiment, the gag, pol, and rev genes are provided on the same plasmid (e.g., FIG. 1C). In another embodiment, the gag and pol genes are provided on a first plasmid and the rev gene is provided on a second plasmid (e.g., FIG. 1D). Accordingly, both 3-vector and 4-vector systems can be used to produce a lentivirus as described in the Examples section and elsewhere herein. The therapeutic vector, the envelope plasmid and at least one helper plasmid are transfected into a packaging cell line. A non-limiting example of a packaging cell line is the 293T/17 HEK cell line. When the therapeutic vector, the envelope plasmid, and at least one helper plasmid are transfected into the packaging cell line, a lentiviral particle is produced.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting production of PARP1.

Figure 1C:
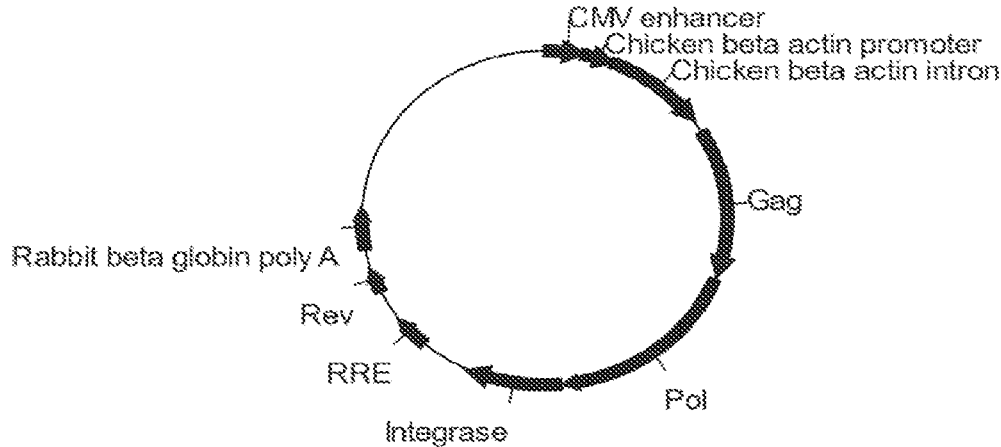
FIG. 1C depicts an exemplary 3-vector lentiviral vector system in a circularized form that includes the experimental therapeutic vector detailed in FIG. 1A.
Figure 1C:
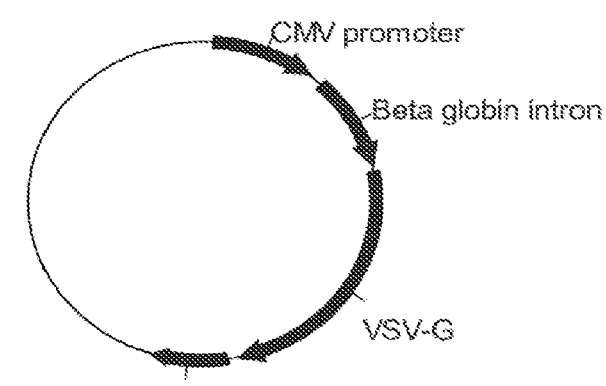
Figure 1C:
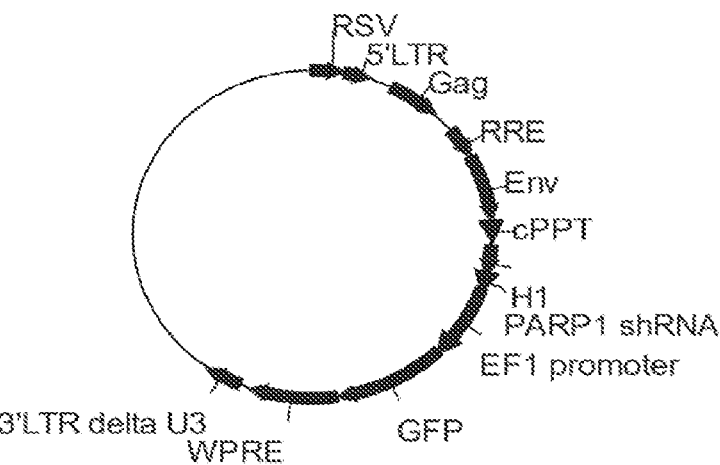

In another aspect, and as detailed in FIG. 1C, the lentiviral vector, which is also referred to herein as a therapeutic vector, includes the following elements: a hybrid 5' long terminal repeat (RSV/5' LTR) (SEQ ID NOS: 21-22), a HIV gag (SEQ ID NO: 23), a RRE (Rev-response element) (SEQ ID NO: 24), a Env element (SEQ ID NO: 25), a cPPT (SEQ ID NO: 26), a H1 promoter (SEQ ID NO: 27), a shRNA targeting PARP1 (shPARP1) (SEQ ID NOS: 6-10), a EF1 promoter (SEQ ID NO: 28), a GFP element (SEQ ID NO:29), a Woodchuck Post-Transcriptional Regulatory Element (WPRE) (SEQ ID NO: 30), and a 3' LTR delta U3 (SEQ ID NO: 31). In another aspect, sequence variation, by way of substitution, deletion, addition, or mutation can be used to modify the sequences references herein.

In another aspect, and as detailed herein for example in FIG. 1C, a helper plasmid has been designed to include the following elements: CMV enhancer (SEQ ID NO: 32); a chicken beta actin promoter (SEQ ID NO: 33); a chicken beta actin intron (SEQ ID NO: 34); a HIV gag (SEQ ID NO: 23); a HIV Pol (SEQ ID NO: 35); a HIV Int (SEQ ID NO: 36); a HIV RRE (SEQ ID NO: 24); a HIV Rev (SEQ ID NO: 37); and a rabbit beta globin poly A (SEQ ID NO: 38). In another aspect, the helper plasmid may be modified to include a first helper plasmid for expressing the gag and pol genes, and a second and separate plasmid for expressing the rev gene. In another aspect, sequence variation, by way of substitution, deletion, addition, or mutation can be used to modify the sequences references herein.

In another aspect, and as detailed herein for example in FIG. 1C, an envelope plasmid has been designed to include the following elements being from left to right: a CMV promoter (SEQ ID NO: 39); a beta globin intron (SEQ ID NO: 40); a VSV-G (SEQ ID NO: 25); and a rabbit beta globin poly A (SEQ ID NO: 38). In another aspect, sequence variation, by way of substitution, deletion, addition, or mutation can be used to modify the sequences references herein.

In another aspect, the plasmids used for lentiviral packaging can be modified with similar elements and the intron sequences can potentially be removed without loss of vector function. For example, the following elements can replace similar elements in the plasmids that comprise the packaging system: Elongation Factor-1 (EF-1), phosphoglycerate kinase (PGK), and ubiquitin C (UbC) promoters can replace the CMV or CAG promoter. SV40 poly A and bGH poly A can replace the rabbit beta globin poly A. The HIV sequences in the helper plasmid can be constructed from different HIV strains or clades. The VSV-G glycoprotein can be substituted with membrane glycoproteins from feline endogenous virus (RD 114), gibbon ape leukemia virus (GALV), Rabies (FUG), lymphocytic choriomeningitis virus (LCMV), influenza A fowl plague virus (FPV), Ross River alphavirus (RRV), murine leukemia virus 10A1 (MLV), or Ebola virus (EboV).

Of note, lentiviral packaging systems can be acquired commercially (e.g., Lenti-vpak packaging kit from OriGene Technologies, Inc., Rockville, MD), and can also be designed as described herein. Moreover, it is within the skill of a person skilled in the art to substitute or modify aspects of a lentiviral packaging system to improve any number of relevant factors, including the production efficiency of a lentiviral particle.

Doses and Dosage Forms

Dosing may occur once per day or several times per day. Dosing may occur with intervals in between dosing. For example, a subject may be treated on a first day, and then treated every other day, or every second day, or every third day, or every fourth day, or every fifth day, or every sixth day, or every seventh day, or every second week, or every month, etc.

However, dosing can also occur once, twice, or several times per year, and such a dosing schedule can be repeated on a yearly basis. A lentiviral particle can be delivered by any method suitable for treating symptoms associated with PD. For example, dosing can be made via direct injection into the brain stem using a guided needle. This will likely occur in conjunction with deep brain stimulation.

In another aspect, a pharmaceutical composition comprising a lentiviral particle as described herein can be formulated in a solid dosage form. The solid dosage form can include excipients known to those skilled in the art. The lentiviral particle as described herein can be formulated in a gel form, a foam form, a biodegradable capsule form, a nanoparticle form, or can be formulated with liposomes or other structures known to those skilled in the art. The solid dosage form can be formulated for immediate release or a modified release. Modified release dosage forms include controlled or extended release forms.

The following examples are given for the purpose of illustrating various embodiments of the invention and are not meant to limit the invention in any fashion. The present examples, along with the methods described herein are presently representative of preferred embodiments, are exemplary, and are not intended as limitations on the scope of the invention. Changes therein, and other uses which are encompassed within the spirit of the invention as defined by the scope of the claims, will occur to those persons skilled in the art.

EXAMPLES

Example 1. Development of a Lentiviral Vector System

A lentiviral vector system was developed as summarized generally in FIG. 1. Lentiviral particles were produced in 293T/17 HEK cells (purchased from American Type Culture Collection, Manassas, VA) following transfection with the therapeutic vector, the envelope plasmid, and the helper plasmid. The transfection of 293T/17 HEK cells, which produced functional viral particles, employed the reagent Poly(ethylenimine) (PEI) to increase the efficiency of plasmid DNA uptake. The plasmids and DNA were initially added separately in culture medium without serum in a ratio of 3:1 (mass ratio of PEI to DNA). After 2-3 days, cell medium was collected and lentiviral particles were purified by high-speed centrifugation and/or filtration followed by anion-exchange chromatography. The concentration of lentiviral particles can be expressed in terms of transducing units/ml (TU/ml). The determination of TU was accomplished by measuring HIV p24 levels in culture fluids (p24 protein is incorporated into lentiviral particles), measuring the number of viral DNA copies per cell by quantitative PCR, or by infecting cells and using light (if the vectors encode luciferase or fluorescent protein markers).

Figure 1D:
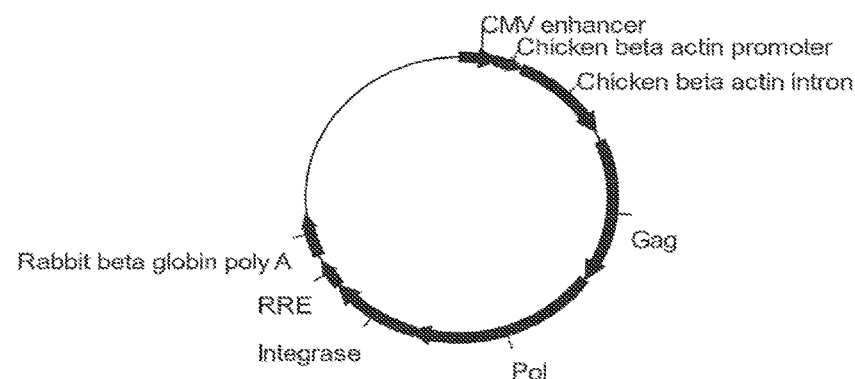
FIG. 1D depicts an exemplary 4-vector lentiviral vector system in a circularized form that includes the experimental therapeutic vector detailed in FIG. 1A.
Figure 1D:
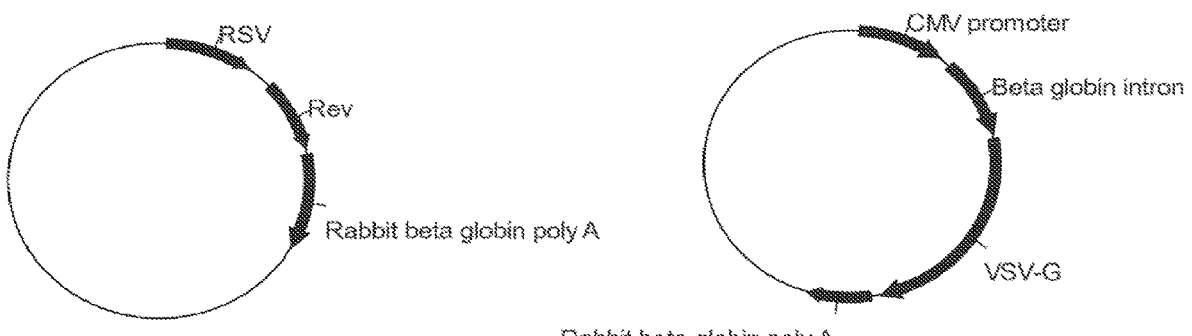
Figure 1D:
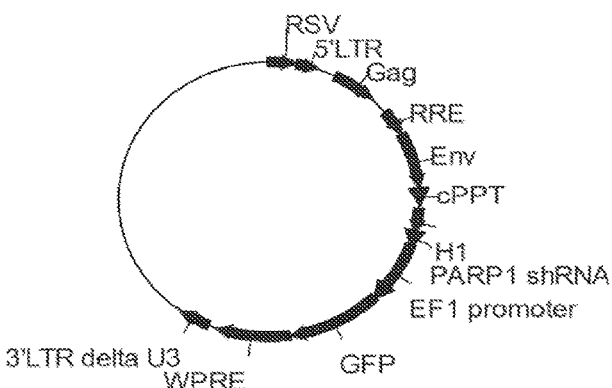
Figure 1E:
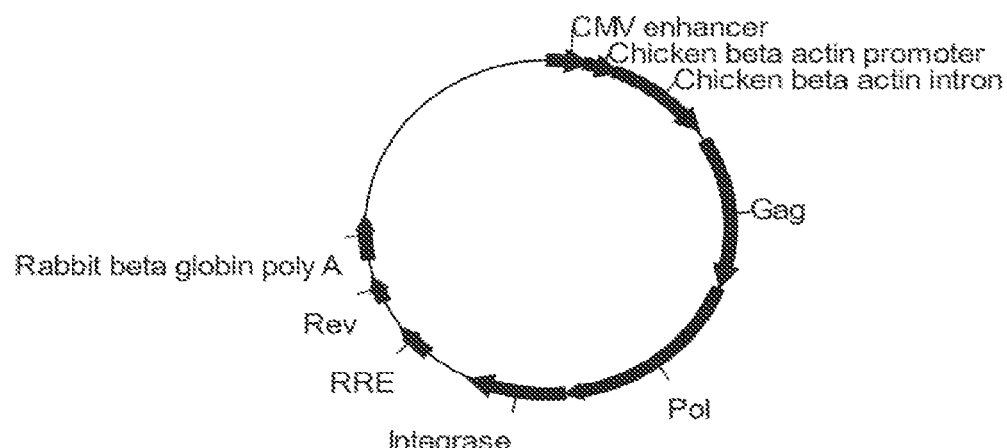
FIG. 1E depicts an exemplary 3-vector lentiviral vector system in a circularized form that includes the therapeutic vector detailed in FIG. 1B.
Figure 1E:
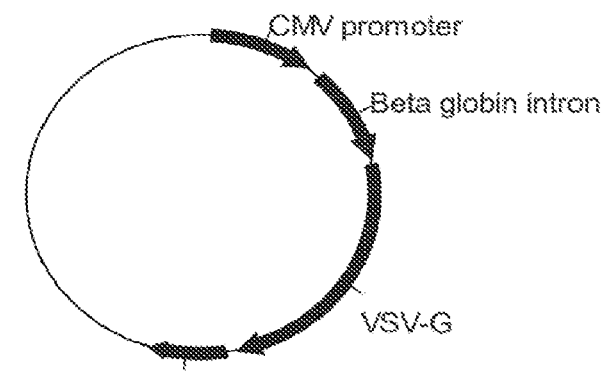
Figure 1E:
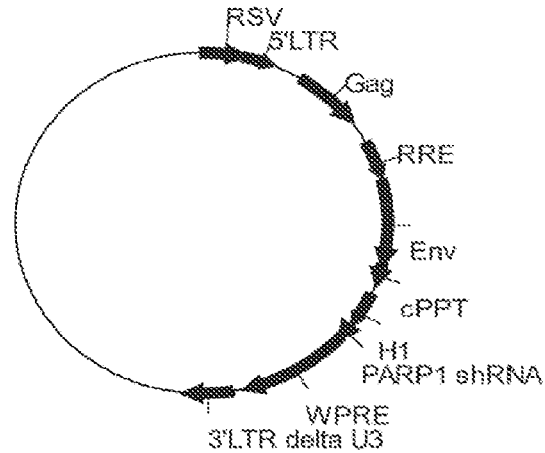

A 3-vector system (i.e., a 2-vector lentiviral packaging system) was designed for the production of lentiviral particles. A schematic of the 3-vector system is shown in FIGS. 1A, 1C, and 1E. Briefly, and with reference to FIGS. 1C and 1E, the top-most vector is a helper plasmid, which, in this case, includes Rev. The vector appearing in the middle of FIGS. 1C and 1E is the envelope plasmid. The bottom-most vector is the therapeutic vector, as described herein.

Referring to FIGS. 1C and 1E, the Helper plus Rev plasmid includes a CMV enhancer (SEQ ID NO: 32); a chicken beta actin promoter (SEQ ID NO: 33); a chicken beta actin intron (SEQ ID NO: 34); a HIV gag (SEQ ID NO: 23); a HIV Pol (SEQ ID NO: 35); a HIV Int (SEQ ID NO: 36); a HIV RRE (SEQ ID NO: 24); a HIV Rev (SEQ ID NO: 37); and a rabbit beta globin poly A (SEQ ID NO: 38). The Helper plus Rev plasmid is also shown in a linear form in FIG. 1A.

Referring to FIGS. 1C and 1E, the Envelope plasmid includes a CMV promoter (SEQ ID NO: 39); a beta globin intron (SEQ ID NO: 40); a VSV-G (SEQ ID NO: 25); and a rabbit beta globin poly A (SEQ ID NO: 38). The Envelope plasmid is also shown in a linear form in FIG. 1A.

Synthesis of a 2-Vector Lentiviral Packaging System Including Helper (Plus Rev) and Envelope Plasmids Materials and Methods:

Construction of the helper plasmid: The helper plasmid was constructed by initial PCR amplification of a DNA fragment from the pNL4-3 HIV plasmid (NIH Aids Reagent Program) containing Gag, Pol, and Integrase genes. Primers were designed to amplify the fragment with EcoRI and NotI restriction sites which could be used to insert at the same sites in the pCDNA3 plasmid (Invitrogen). The forward primer was (5'-TAAGCAGAATTC ATGAATTTGCCAG-GAAGAT-3') (SEQ ID NO: 41) and reverse primer was (5'-CCATACAATGAATGGACACTAGGCGGCCGCAC-GAAT-3') (SEQ ID NO: 42).

The sequence for the Gag, Pol Integrase fragment was as follows:

```
                                    (SEQ ID NO: 43)
GAATTCATGAATTTGCCAGGAAGATGGAAACCAAAAATGATAGGG

GGAATTGGAGGTTTTATCAAAGTAAGACAGTATGATCAGATACTC

ATAGAAATCTGCGGACATAAAGCTATAGGTACAGTATTAGTAGGA

CCTACACCTGTCAACATAATTGGAAGAAATCTGTTGACTCAGATT

GGCTGCACTTTAAATTTTCCCATTAGTCCTATTGAGACTGTACCA

GTAAAATTAAAGCCAGGAATGGATGGCCCAAAAGTTAAACAATGG

CCATTGACAGAAGAAAAAATAAAAGCATTAGTAGAAATTTGTACA

GAAATGGAAAAGGAAGGAAAAATTTCAAAAATTGGGCCTGAAAAT

CCATACAATACTCCAGTATTTGCCATAAAGAAAAAAGACAGTACT

AAATGGAGAAAATTAGTAGATTTCAGAGAACTTAATAAGAGAACT

CAAGATTTCTGGGAAGTTCAATTAGGAATACCACATCCTGCAGGG

TTAAAACAGAAAAAATCAGTAACAGTACTGGATGTGGGCGATGCA

TATTTTTCAGTTCCCTTAGATAAAGACTTCAGGAAGTATACTGCA

TTTACCATACCTAGTATAAACAATGAGACACCAGGGATTAGATAT

CAGTACAATGTGCTTCCACAGGGATGGAAAGGATCACCAGCAATA

TTCCAGTGTAGCATGACAAAAATCTTAGAGCCTTTTAGAAAACAA

AATCCAGACATAGTCATCTATCAATACATGGATGATTTGTATGTA

GGATCTGACTTAGAAATAGGGCAGCATAGAACAAAAATAGAGGAA

CTGAGACAACATCTGTTGAGGTGGGGATTTACCACACCAGACAAA

AAACATCAGAAAGAACCTCCATTCCTTTGGATGGGTTATGAACTC

CATCCTGATAAATGGACAGTACAGCCTATAGTGCTGCCAGAAAAG

GACAGCTGGACTGTCAATGACATACAGAAATTAGTGGGAAAATTG

AATTGGGCAAGTCAGATTTATGCAGGGATTAAAGTAAGGCAATTA

TGTAAACTTCTTAGGGGAACCAAAGCACTAACAGAAGTAGTACCA

CTAACAGAAGAAGCAGAGCTAGAACTGGCAGAAAACAGGGAGATT

CTAAAAGAACCGGTACATGGAGTGTATTATGACCCATCAAAAGAC

TTAATAGCAGAAATACAGAAGCAGGGGCAAGGCCAATGGACATAT

CAAATTTATCAAGAGCCATTTAAAAATCTGAAAACAGGAAAGTAT

GCAAGAATGAAGGGTGCCCACACTAATGATGTGAAACAATTAACA

GAGGCAGTACAAAAAATAGCCACAGAAAGCATAGTAATATGGGA

AAGACTCCTAAATTTAAATTACCCATACAAAAGGAAACATGGGAA

GCATGGTGGACAGAGTATTGGCAAGCCACCTGGATTCCTGAGTGG

GAGTTTGTCAATACCCCTCCCTTAGTGAAGTTATGGTACCAGTTA

GAGAAAGAACCCATAATAGGAGCAGAAACTTTCTATGTAGATGGG

GCAGCCAATAGGGAAACTAAATTAGGAAAAGCAGGATATGTAACT

GACAGAGGAAGACAAAAAGTTGTCCCCCTAACGGACACAACAAAT

CAGAAGACTGAGTTACAAGCAATTCATCTAGCTTTGCAGGATTCG

GGATTAGAAGTAAACATAGTGACAGACTCACAATATGCATTGGGA
```

-continued

```
ATCATTCAAGCACAACCAGATAAGAGTGAATCAGAGTTAGTCAGT

CAAATAATAGAGCAGTTAATAAAAAAGGAAAAAGTCTACCTGGCA

TGGGTACCAGCACACAAAGGAATTGGAGGAAATGAACAAGTAGAT

AAATTGGTCAGTGCTGGAATCAGGAAAGTACTATTTTTAGATGGA

ATAGATAAGGCCCAAGAAGAACATGAGAAATATCACAGTAATTGG

AGAGCAATGGCTAGTGATTTTAACCTACCACCTGTAGTAGCAAAA

GAAATAGTAGCCAGCTGTGATAAATGTCAGCTAAAAGGGGAAGCC

ATGCATGGACAAGTAGACTGTAGCCCAGGAATATGGCAGCTAGAT

TGTACACATTTAGAAGGAAAAGTTATCTTGGTAGCAGTTCATGTA

GCCAGTGGATATATAGAAGCAGAAGTAATTCCAGCAGAGACAGGG

CAAGAAACAGCATACTTCCTCTTAAAATTAGCAGGAAGATGGCCA

GTAAAAACAGTACATACAGACAATGGCAGCAATTTCACCAGTACT

ACAGTTAAGGCCGCCTGTTGGTGGGCGGGGATCAAGCAGGAATTT

GGCATTCCCTACAATCCCCAAAGTCAAGGAGTAATAGAATCTATG

AATAAAGAATTAAAGAAAATTATAGGACAGGTAAGAGATCAGGCT

GAACATCTTAAGACAGCAGTACAAATGGCAGTATTCATCCACAAT

TTTAAAGAAAAGGGGGGATTGGGGGGTACAGTGCAGGGGAAAGA

ATAGTAGACATAATAGCAACAGACATACAAACTAAAGAATTACAA

AAACAAATTACAAAAATTCAAAATTTTCGGGTTTATTACAGGGAC

AGCAGAGATCCAGTTTGGAAAGGACCAGCAAAGCTCCTCTGGAAA

GGTGAAGGGGCAGTAGTAATACAAGATAATAGTGACATAAAAGTA

GTGCCAAGAAGAAAAGCAAAGATCATCAGGGATTATGGAAAACAG

ATGGCAGGTGATGATTGTGTGGCAAGTAGACAGGATGAGGATTAA
```

Next, a DNA fragment containing the Rev, RRE, and rabbit beta globin poly A sequence with XbaI and XmaI flanking restriction sites was synthesized by MWG Operon. The DNA fragment was then inserted into the plasmid at the XbaI and XmaI restriction sites The DNA sequence was as follows:

```
                                    (SEQ ID NO: 44)
TCTAGAATGGCAGGAAGAAGCGGAGACAGCGACGAAGAGCTCATC

AGAACAGTCAGACTCATCAAGCTTCTCTATCAAAGCAACCCACCT

CCCAATCCCGAGGGGACCCGACAGGCCCGAAGGAATAGAAGAAGA

AGGTGGAGAGAGAGACAGAGACAGATCCATTCGATTAGTGAACGG

ATCCTTGGCACTTATCTGGGACGATCTGCGGAGCCTGTGCCTCTT

CAGCTACCACCGCTTGAGAGACTTACTCTTGATTGTAACGAGGAT

TGTGGAACTTCTGGGACGCAGGGGGTGGGAAGCCCTCAAATATTG

GTGGAATCTCCTACAATATTGGAGTCAGGAGCTAAAGAATAGAGG

AGCTTTGTTCCTTGGGTTCTTGGGAGCAGCAGGAAGCACTATGGG

CGCAGCGTCAATGACGCTGACGGTACAGGCCAGACAATTATTGTC

TGGTATAGTGCAGCAGCAGAACAATTTGCTGAGGGCTATTGAGGC

GCAACAGCATCTGTTGCAACTCACAGTCTGGGGCATCAAGCAGCT
```

-continued

```
CCAGGCAAGAATCCTGGCTGTGGAAAGATACCTAAAGGATCAACA

GCTCCTAGATCTTTTTCCCTCTGCCAAAAATTATGGGGACATCAT

GAAGCCCCTTGAGCATCTGACTTCTGGCTAATAAAGGAAATTTAT

TTTCATTGCAATAGTGTGTTGGAATTTTTTGTGTCTCTCACTCGG

AAGGACATATGGGAGGGCAAATCATTTAAAACATCAGAATGAGTA

TTTGGTTTAGAGTTTGGCAACATATGCCATATGCTGGCTGCCATG

AACAAAGGTGGCTATAAAGAGGTCATCAGTATATGAAACAGCCCC

CTGCTGTCCATTCCTTATTCCATAGAAAAGCCTTGACTTGAGGTT

AGATTTTTTTTATATTTTGTTTTGTGTTATTTTTTTCTTTAACAT

CCCTAAAATTTTCCTTACATGTTTTACTAGCCAGATTTTTCCTCC

TCTCCTGACTACTCCCAGTCATAGCTGTCCCTCTTCTCTTATGAA

GATCCCTCGACCTGCAGCCCAAGCTTGGCGTAATCATGGTCATAG

CTGTTTCCTGTGTGAAATTGTTATCCGCTCACAATTCCACACAAC

ATACGAGCCGGAAGCATAAAGTGTAAAGCCTGGGGTGCCTAATGA

GTGAGCTAACTCACATTAATTGCGTTGCGCTCACTGCCCGCTTTC

CAGTCGGGAAACCTGTCGTGCCAGCGGATCCGCATCTCAATTAGT

CAGCAACCATAGTCCCGCCCCTAACTCCGCCCATCCCGCCCCTAA

CTCCGCCCAGTTCCGCCCATTCTCCGCCCCATGGCTGACTAATTT

TTTTTATTTATGCAGAGGCCGAGGCCGCCTCGGCCTCTGAGCTAT

TCCAGAAGTAGTGAGGAGGCTTTTTTGGAGGCCTAGGCTTTTGCA

AAAAGCTAACTTGTTTATTGCAGCTTATAATGGTTACAAATAAAG

CAATAGCATCACAAATTTCACAAATAAAGCATTTTTTTCACTGCA

TTCTAGTTGTGGTTTGTCCAAACTCATCAATGTATCTTATCAGCG

GCCGCCCGGG
```

Finally, the CMV promoter of pCDNA3.1 was replaced with the CAG enhancer/promoter plus a chicken beta actin intron sequence. A DNA fragment containing the CAG enhancer/promoter/intron sequence with MluI and EcoRI flanking restriction sites was synthesized by MWG Operon. The DNA fragment was then inserted into the plasmid at the MluI and EcoRI restriction sites. The DNA sequence was as follows:

```
                                    (SEQ ID NO: 45)
ACGCGTTAGTTATTAATAGTAATCAATTACGGGGTCATTAGTTCA

TAGCCCATATATGGAGTTCCGCGTTACATAACTTACGGTAAATGG

CCCGCCTGGCTGACCGCCCAACGACCCCCGCCCATTGACGTCAAT

AATGACGTATGTTCCCATAGTAACGCCAATAGGGACTTTCCATTG

ACGTCAATGGGTGGACTATTTACGGTAAACTGCCCACTTGGCAGT

ACATCAAGTGTATCATATGCCAAGTACGCCCCCTATTGACGTCAA

TGACGGTAAATGGCCCGCCTGGCATTATGCCCAGTACATGACCTT

ATGGGACTTTCCTACTTGGCAGTACATCTACGTATTAGTCATCGC

TATTACCATGGGTCGAGGTGAGCCCCACGTTCTGCTTCACTCTCC

CCATCTCCCCCCCCTCCCCACCCCCAATTTTGTATTTATTTATTT
```

-continued

```
TTTAATTATTTTGTGCAGCGATGGGGGCGGGGGGGGGGGGGCGC

GCGCCAGGCGGGGCGGGGCGGGGCGAGGGGCGGGGCGGGGCGAGG

CGGAGAGGTGCGGCGGCAGCCAATCAGAGCGGCGCGCTCCGAAAG

TTTCCTTTTATGGCGAGGCGGCGGCGGCGGCGGCCCTATAAAAAG

CGAAGCGCGCGGCGGGCGGGAGTCGCTGCGTTGCCTTCGCCCCGT

GCCCCGCTCCGCGCCGCCTCGCGCCGCCCGCCCCGGCTCTGACTG

ACCGCGTTACTCCCACAGGTGAGCGGGCGGGACGGCCCTTCTCCT

CCGGGCTGTAATTAGCGCTTGGTTTAATGACGGCTCGTTTCTTTT

CTGTGGCTGCGTGAAAGCCTTAAAGGGCTCCGGGAGGGCCCTTTG

TGCGGGGGGGAGCGGCTCGGGGGGTGCGTGCGTGTGTGTGTGCGT

GGGGAGCGCCGCGTGCGGCCCGCGCTGCCCGGCGGCTGTGAGCGC

TGCGGGCGCGGCGCGGGGCTTTGTGCGCTCCGCGTGTGCGCGAGG

GGAGCGCGGCCGGGGGCGGTGCCCCGCGGTGCGGGGGGGCTGCGA

GGGGAACAAAGGCTGCGTGCGGGGTGTGTGCGTGGGGGGGTGAGC

AGGGGGTGTGGGCGCGGCGGTCGGGCGTGTAACCCCCCCCTGCACC

CCCCTCCCCGAGTTGCTGAGCACGGCCCGGCTTCGGGTGCGGGGC

TCCGTGCGGGGCGTGGCGCGGGGCTCGCCGTGCCGGGCGGGGGGT

GGCGGCAGGTGGGGGTGCCGGGCGGGGCGGGGCCGCCTCGGGCCG

GGGAGGGCTCGGGGGAGGGGCGCGGCGGCCCCGGAGCGCCGGCGG

CTGTCGAGGCGCGGCGAGCCGCAGCCATTGCCTTTTATGGTAATC

GTGCGAGAGGGCGCAGGGACTTCCTTTGTCCCAAATCTGGCGGAG

CCGAAATCTGGGAGGCGCCGCCGCACCCCCTCTAGCGGGCGCGGG

CGAAGCGGTGCGGCGCCGGCAGGAAGGAAATGGGCGGGGAGGGCC

TTCGTGCGTCGCCGCGCCGCCGTCCCCTTCTCCATCTCCAGCCTC

GGGGCTGCCGCAGGGGGACGGCTGCCTTCGGGGGGGACGGGGCAG

GGCGGGGTTCGGCTTCTGGCGTGTGACCGGCGGGAATTC
```

Construction of the VSV-G Envelope Plasmid:

The vesicular stomatitis Indiana virus glycoprotein (VSV-G) sequence was synthesized by MWG Operon with flanking EcoRI restriction sites. The DNA fragment was then inserted into the pCDNA3.1 plasmid (Invitrogen) at the EcoRI restriction site and the correct orientation was determined by sequencing using a CMV specific primer. The DNA sequence was as follows:

```
                                    (SEQ ID NO: 46)
GAATTCATGAAGTGCCTTTTGTACTTAGCCTTTTTATTCATTGGG

GTGAATTGCAAGTTCACCATAGTTTTTCCACACAACCAAAAAGGA

AACTGGAAAAATGTTCCTTCTAATTACCATTATTGCCCGTCAAGC

TCAGATTTAAATTGGCATAATGACTTAATAGGCACAGCCTTACAA

GTCAAAATGCCCAAGAGTCACAAGGCTATTCAAGCAGACGGTTGG

ATGTGTCATGCTTCCAAATGGGTCACTACTTGTGATTTCCGCTGG

TATGGACCGAAGTATATAACACATTCCATCCGATCCTTCACTCCA

TCTGTAGAACAATGCAAGGAAAGCATTGAACAAACGAAACAAGGA
```

-continued

```
ACTTGGCTGAATCCAGGCTTCCCTCCTCAAAGTTGTGGATATGCA

ACTGTGACGGATGCCGAAGCAGTGATTGTCCAGGTGACTCCTCAC

CATGTGCTGGTTGATGAATACACAGGAGAATGGGTTGATTCACAG

TTCATCAACGGAAAATGCAGCAATTACATATGCCCCACTGTCCAT

AACTCTACAACCTGGCATTCTGACTATAAGGTCAAAGGGCTATGT

GATTCTAACCTCATTTCCATGGACATCACCTTCTTCTCAGAGGAC

GGAGAGCTATCATCCCTGGGAAAGGAGGGCACAGGGTTCAGAAGT

AACTACTTTGCTTATGAAACTGGAGGCAAGGCCTGCAAAATGCAA

TACTGCAAGCATTGGGGAGTCAGACTCCCATCAGGTGTCTGGTTC

GAGATGGCTGATAAGGATCTCTTTGCTGCAGCCAGATTCCCTGAA

TGCCCAGAAGGGTCAAGTATCTCTGCTCCATCTCAGACCTCAGTG

GATGTAAGTCTAATTCAGGACGTTGAGAGGATCTTGGATTATTCC

CTCTGCCAAGAAACCTGGAGCAAAATCAGAGCGGGTCTTCCAATC

TCTCCAGTGGATCTCAGCTATCTTGCTCCTAAAAACCCAGGAACC

GGTCCTGCTTTCACCATAATCAATGGTACCCTAAAATACTTTGAG

ACCAGATACATCAGAGTCGATATTGCTGCTCCAATCCTCTCAAGA

ATGGTCGGAATGATCAGTGGAACTACCACAGAAAGGGAACTGTGG

GATGACTGGGCACCATATGAAGACGTGGAAATTGGACCCAATGGA

GTTCTGAGGACCAGTTCAGGATATAAGTTTCCTTTATACATGATT

GGACATGGTATGTTGGACTCCGATCTTCATCTTAGCTCAAAGGCT

CAGGTGTTCGAACATCCTCACATTCAAGACGCTGCTTCGCAACTT

CCTGATGATGAGAGTTTATTTTTTGGTGATACTGGGCTATCCAAA

AATCCAATCGAGCTTGTAGAAGGTTGGTTCAGTAGTTGGAAAAGC

TCTATTGCCTCTTTTTTCTTTATCATAGGGTTAATCATTGGACTA

TTCTTGGTTCTCCGAGTTGGTATCCATCTTTGCATTAAATTAAAG

CACACCAAGAAAGACAGATTTATACAGACATAGAGATGAGAATTC
```

Figure 1F:
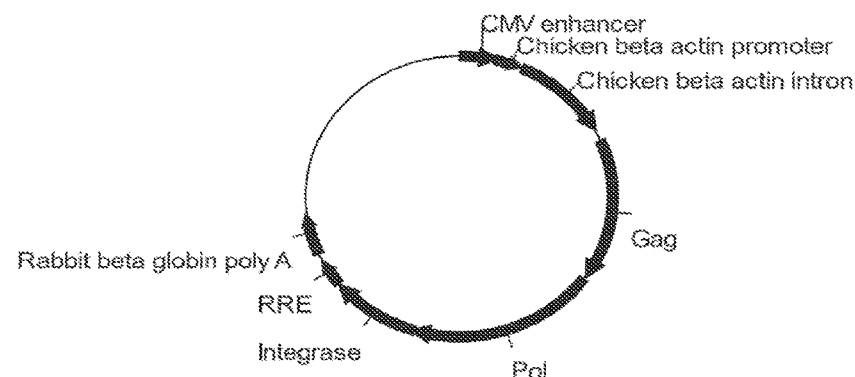
FIG. 1F depicts an exemplary 4-vector lentiviral vector system in a circularized form that includes the therapeutic vector detailed in FIG. 1B.
Figure 1F:
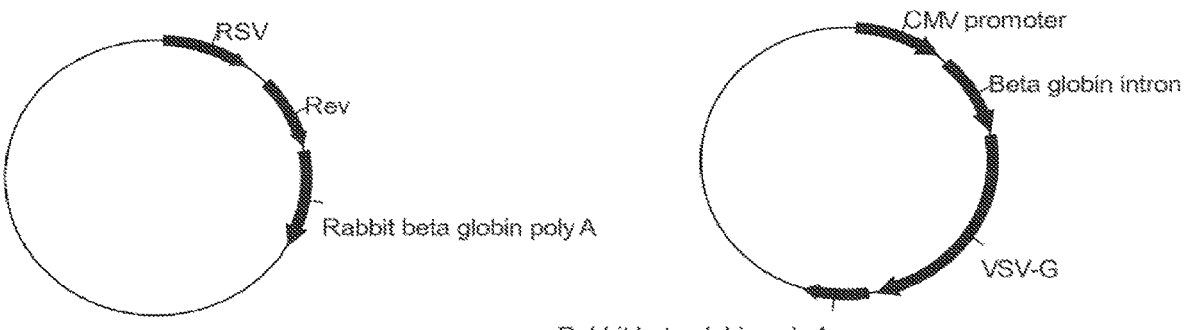
Figure 1F:
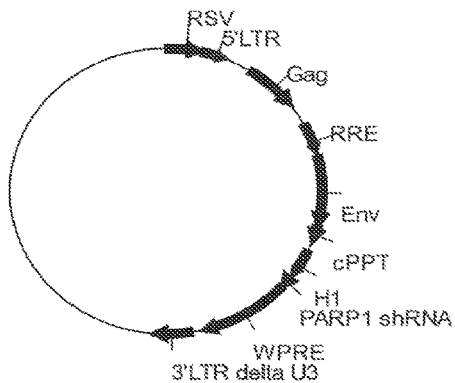

A 4-vector system (i.e., a 3-vector lentiviral packaging system) has also been designed and produced using the methods and materials described herein. A schematic of the 4-vector system is shown in FIGS. 1D and 1F. Briefly, and with reference to FIGS. 1D and 1F, the top-most vector is a helper plasmid, which, in this case, does not include Rev. The vector second from the top, oriented at the left aspect of the page, is a separate Rev plasmid. The vector second from the bottom, oriented at the right aspect of the page, is the envelope plasmid. The bottom-most vector is an experimental therapeutic vector.

Referring to FIGS. 1D and 1F, the Helper plasmid includes a CMV enhancer (SEQ ID NO: 32); a chicken beta actin promoter (SEQ ID NO: 33); a chicken beta actin intron (SEQ ID NO: 34); a HIV gag (SEQ ID NO: 23); a HIV Pol (SEQ ID NO: 35); a HIV Int (SEQ ID NO: 36); a HIV RRE (SEQ ID NO: 24); and a rabbit beta globin poly A (SEQ ID NO: 38).

Referring to FIGS. 1D and 1F, the Rev plasmid includes a RSV promoter (SEQ ID NO: 47); a HIV Rev (SEQ ID NO: 37); and a rabbit beta globin poly A (SEQ ID NO: 38).

Referring to FIGS. 1D and 1F, the Envelope plasmid includes a CMV promoter (SEQ ID NO: 39); a beta globin intron (SEQ ID NO: 40); a VSV-G (SEQ ID NO: 25); and a rabbit beta globin poly A (SEQ ID NO: 38). The Envelope plasmid is also shown in a linear form in FIG. 1A.

Synthesis of a 3-Vector Lentiviral Packaging System Including Helper, Rev, and Envelope Plasmids Materials and Methods:

Construction of the Helper Plasmid without Rev:

The Helper plasmid without Rev was constructed by inserting a DNA fragment containing the RRE and rabbit beta globin poly A sequence. This sequence was synthesized by MWG Operon with flanking XbaI and XmaI restriction sites. The RRE/rabbit poly A beta globin sequence was then inserted into the Helper plasmid at the XbaI and XmaI restriction sites. The DNA sequence is as follows:

```
                                          (SEQ ID NO: 44)
TCTAGAAGGAGCTTTGTTCCTTGGGTTCTTGGGAGCAGCAGGAAG

CACTATGGGCGCAGCGTCAATGACGCTGACGGTACAGGCCAGACA

ATTATTGTCTGGTATAGTGCAGCAGCAGAACAATTTGCTGAGGGC

TATTGAGGCGCAACAGCATCTGTTGCAACTCACAGTCTGGGGCAT

CAAGCAGCTCCAGGCAAGAATCCTGGCTGTGGAAAGATACCTAAA

GGATCAACAGCTCCTAGATCTTTTTCCCTCTGCCAAAAATTATGG

GGACATCATGAAGCCCCTTGAGCATCTGACTTCTGGCTAATAAAG

GAAATTTATTTTCATTGCAATAGTGTGTTGGAATTTTTTGTGTCT

CTCACTCGGAAGGACATATGGGAGGGCAAATCATTTAAAACATCA

GAATGAGTATTTGGTTTAGAGTTTGGCAACATATGCCATATGCTG

GCTGCCATGAACAAAGGTGGCTATAAAGAGGTCATCAGTATATGA

AACAGCCCCCTGCTGTCCATTCCTTATTCCATAGAAAAGCCTTGA

CTTGAGGTTAGATTTTTTTTATATTTTGTTTTGTGTTATTTTTTT

CTTTAACATCCCTAAAATTTTCCTTACATGTTTTACTAGCCAGAT

TTTTCCTCCTCTCCTGACTACTCCCAGTCATAGCTGTCCCTCTTC

TCTTATGAAGATCCCTCGACCTGCAGCCCAAGCTTGGCGTAATCA

TGGTCATAGCTGTTTCCTGTGTGAAATTGTTATCCGCTCACAATT

CCACACAACATACGAGCCGGAAGCATAAAGTGTAAAGCCTGGGGT

GCCTAATGAGTGAGCTAACTCACATTAATTGCGTTGCGCTCACTG

CCCGCTTTCCAGTCGGGAAACCTGTCGTGCCAGCGGATCCGCATC

TCAATTAGTCAGCAACCATAGTCCCGCCCCTAACTCCGCCCATCC

CGCCCCTAACTCCGCCCAGTTCCGCCCATTCTCCGCCCCATGGCT

GACTAATTTTTTTTATTTATGCAGAGGCCGAGGCCGCCTCGGCCT

CTGAGCTATTCCAGAAGTAGTGAGGAGGCTTTTTTGGAGGCCTAG

GCTTTTGCAAAAAGCTAACTTGTTTATTGCAGCTTATAATGGTTA

CAAATAAAGCAATAGCATCACAAATTTCACAAATAAAGCATTTTT

TTCACTGCATTCTAGTTGTGGTTTGTCCAAACTCATCAATGTATC

TTATCACCCGGG
```

Construction of the Rev Plasmid:

The RSV promoter and HIV Rev sequence was synthesized as a single DNA fragment by MWG Operon with flanking MfeI and XbaI restriction sites. The DNA fragment was then inserted into the pCDNA3.1 plasmid (Invitrogen) at the MfeI and XbaI restriction sites in which the CMV promoter is replaced with the RSV promoter. The DNA sequence was as follows:

```
                                        (SEQ ID NO: 48)
CAATTGCGATGTACGGGCCAGATATACGCGTATCTGAGGGGACTA

GGGTGTGTTTAGGCGAAAAGCGGGGCTTCGGTTGTACGCGGTTAG

GAGTCCCCTCAGGATATAGTAGTTTCGCTTTTGCATAGGGAGGGG

GAAATGTAGTCTTATGCAATACACTTGTAGTCTTGCAACATGGTA

ACGATGAGTTAGCAACATGCCTTACAAGGAGAGAAAAAGCACCGT

GCATGCCGATTGGTGGAAGTAAGGTGGTACGATCGTGCCTTATTA

GGAAGGCAACAGACAGGTCTGACATGGATTGGACGAACCACTGAA

TTCCGCATTGCAGAGATAATTGTATTTAAGTGCCTAGCTCGATAC

AATAAACGCCATTTGACCATTCACCACATTGGTGTGCACCTCCAA

GCTCGAGCTCGTTTAGTGAACCGTCAGATCGCCTGGAGACGCCAT

CCACGCTGTTTTGACCTCCATAGAAGACACCGGGACCGATCCAGC

CTCCCCTCGAAGCTAGCGATTAGGCATCTCCTATGGCAGGAAGAA

GCGGAGACAGCGACGAAGAACTCCTCAAGGCAGTCAGACTCATCA

AGTTTCTCTATCAAAGCAACCCACCTCCCAATCCCGAGGGGACCC

GACAGGCCCGAAGGAATAGAAGAAGAAGGTGGAGAGAGAGACAGA

GACAGATCCATTCGATTAGTGAACGGATCCTTAGCACTTATCTGG

GACGATCTGCGGAGCCTGTGCCTCTTCAGCTACCACCGCTTGAGA

GACTTACTCTTGATTGTAACGAGGATTGTGGAACTTCTGGGACGC

AGGGGGTGGGAAGCCCTCAAATATTGGTGGAATCTCCTACAATAT

TGGAGTCAGGAGCTAAAGAATAGTCTAGA
```

The plasmids for the 3-vector and 4-vector packaging systems can be modified with similar elements and the intron sequences could potentially be removed without loss of vector function. For example, the following elements could replace similar elements in the 3-vector and 4-vector packaging system:

Promoters: Elongation Factor-1 (EF-1) (SEQ ID NO: 28), phosphoglycerate kinase (PGK) (SEQ ID NO: 49), and ubiquitin C (UbC) (SEQ ID NO: 50) can replace the CMV or CAG promoter (SEQ ID NO: 39). These sequences can also be further varied by addition, substitution, deletion or mutation.

Poly A sequences: SV40 poly A (SEQ ID NO: 51) and bGH poly A (SEQ ID NO: 52) can replace the rabbit beta globin poly A (SEQ ID NO: 38). These sequences can also be further varied by addition, substitution, deletion or mutation.

HIV Gag, Pol, and Integrase sequences: the HIV sequences in the Helper plasmid can be constructed from different HIV strains or clades. For example, HIV Gag (SEQ ID NO: 23); HIV Pol (SEQ ID NO: 35); and HIV Int (SEQ ID NO: 36) from the Bal strain can be interchanged with the gag, pol, and int sequences contained in the helper/helper plus Rev plasmids as outlined herein. These sequences can also be further varied by addition, substitution, deletion or mutation.

Envelope: The VSV-G glycoprotein can be substituted with membrane glycoproteins from feline endogenous virus (RD 114) (SEQ ID NO: 53), gibbon ape leukemia virus (GALV) (SEQ ID NO: 54), Rabies (FUG) (SEQ ID NO: 55), lymphocytic choriomeningitis virus (LCMV) (SEQ ID NO: 56), influenza A fowl plague virus (FPV) (SEQ ID NO: 57), Ross River alphavirus (RRV) (SEQ ID NO: 58), murine leukemia virus 10A1 (MLV) (SEQ ID NO: 59), or Ebola virus (EboV) (SEQ ID NO: 60). Sequences for these envelopes are identified in the sequence portion herein. Further, these sequences can also be further varied by addition, substitution, deletion or mutation.

In summary, the 3-vector versus 4-vector systems can be compared and contrasted, in part, as follows. The 3-vector lentiviral vector system contains: 1. Helper plasmid: HIV Gag, Pol, Integrase, and Rev/Tat; 2. Envelope plasmid: VSV-G envelope; and 3. Therapeutic vector: RSV/5' LTR, HIV Gag, RRE, Env, cPPT, H1, shPARP1, EF1, GFP, WPRE, and a 3'LTR A U3. The 4-vector lentiviral vector system contains: 1. Helper plasmid: HIV Gag, Pol, and Integrase; 2. Rev plasmid: Rev; 3. Envelope plasmid: VSV-G envelope; and 4. Therapeutic vector: RSV/5' LTR, HIV Gag, RRE, Env, a cPPT, a H1 element, shPARP1, EF1, GFP, WPRE, and a 3'A LTR. Sequences corresponding with the above elements are identified in the sequence listings portion herein.

Example 2. Development of PARP1 Inhibitory RNA for Use in a Lentiviral Vector in the Lentiviral Vector System The purpose of this Example was to develop a PARP1 inhibitor RNA lentivirus vector.

Inhibitory RNA Design. The sequence of *Homo sapiens* poly ADP-ribose polymerase (PARP1) mRNA (NM 001618) or *Mus musculus* Parp1 mRNA (NM 007415) was used to search for potential siRNA or shRNA candidates to knockdown PARP1 levels in human or mouse cells. Potential RNA interference sequences were chosen from candidates selected by siRNA or shRNA design programs such as those from the Broad Institute (MIT) Genetic Perturbation Platform (GPP) Web Portal or the BLOCK-iT™ RNAi Designer from ThermoFisher Scientific. Potential RNA interference sequences were chosen from candidates selected by siRNA or shRNA design programs such as from GPP Web Portal hosted by the Broad Institute (portals.broadinstitute.org/gpp/public/) or the BLOCK-iT RNAi Designer from Thermo Scientific (maidesigner.thermofisher.com/maiexpress/).

Vector Construction. For PARP1 shRNAs, oligonucleotide sequences containing BamHI and EcoRI restriction sites were synthesized by MWG operon. Oligonucleotide sequences were annealed by incubation at 70 degrees Celsius and cooling to room temperature. Annealed oligonucleotides were digested with the restriction enzymes BamHI and EcoRI for one hour at 37 degrees Celsius and then the enzymes were heat-inactivated at 70 degrees Celsius for 20 minutes. In parallel, a lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Invitrogen. The DNA concentration was determined by spectrophotometry at the absorbance wavelength of 260 nm. The vector and oligonucleotide sequences were ligated in the ratio 3:1 (insert to vector). The ligation reaction was carried out with T4 DNA ligase for 30 minutes at room temperature. 2.5 microliters of the ligation mixture was added to 25 microliters of STBL3 competent bacterial cells. Transformation was carried out by heat-shock at 42 degrees Celsius. Bacterial cells were streaked onto agar plates containing ampicillin and then colonies were expanded in LB broth. To check for insertion of the oligo sequences, plasmid DNA was extracted from harvested bacteria cultures with the Invitrogen DNA mini prep kit. Insertion of the shRNA sequence in the lentiviral vector was verified by DNA sequencing using a specific primer for which ever promoter is used to regulate shRNA expression. The lentiviral vectors containing a correct PARP1 sequence were then used to package lentiviral particles to test for their ability to knockdown PARP1. Mammalian cells were transduced with lentiviral particles either in the presence or absence of polybrene. Cells were collected after 2-4 days and protein was analyzed by western blot for PARP1 expression.

The *Homo sapiens* PARP1 target sequences summarized in Table 1 were identified in respect of these experiments and in relation to the shRNA oligonucleotide sequences outlined in Table 2 herein.

TABLE 1

| Homo sapiens PARP1 Target Sequences | |
| --- | --- |
| SEQ ID NO .: | Sequence |
| 1 | CTTCGTTAGAATGTCTGCCTT |
| 2 | GCAGCTTCATAACCGAAGATT |
| 3 | CCGAGAAATCTCTTACCTCAA |
| 4 | CGACCTGATCTGGAACATCAA |
| 5 | GTTGCTGATGGGTAGTACC |

The following *Homo sapiens* PARP1 shRNA oligonucleotide sequences summarized in Table 2 were used in these experiments:

TABLE 2

| Homo sapiens PARP1 shRNA Oligonucleotide Sequences | |
| --- | --- |
| SEQ ID NO.: | Sequence |
| 6 | CTTCGTTAGAATGTCTGCCTTCTCGAG AAGGCAGACATTCTAACGAAGTTTTT |
| 7 | GCAGCTTCATAACCGAAGATTCTCGAG AATCTTCGGTTATGAAGCTGCTTTTT |
| 8 | CCGAGAAATCTCTTACCTCAACTCGAG TTGAGGTAAGAGATTTCTCGGTTTTT |
| 9 | CGACCTGATCTGGAACATCAACTCGAG TTGATGTTCCAGATCAGGTCGTTTTT |
| 10 | GTTGCTGATGGGTAGTACCTTCAAGAG AGGTACTACCCATCAGCAACTTTTT |

The *Mus musculus* PARP1 target sequences summarized in Table 3 were identified in respect of these experiments and in relation to the shRNA oligonucleotide sequences outlined in Table 4 herein:

TABLE 3

| Mus musculus PARP1 Target Sequences | |
| --- | --- |
| SEQ ID NO .: | Sequence |
| 11 | GCACTTCATGAAGCTGTATGA |
| 12 | GCACAGTTATCGGCAGTAACA |
| 13 | GGAGGCAAGTTGACAGGATCT |
| 14 | TCGACGTCAACTACGAGAAAC |
| 15 | GCCCTTGGAAACATGTATGAA |

The following *Mus musculus* PARP1 shRNA oligonucleotide sequences summarized in Table 4 were used in these experiments:

TABLE 4

| Mus musculus PARP1 shRNA Oligonucleotide Sequences | |
| --- | --- |
| SEQ ID NO .: | Sequence |
| 16 | GCACTTCATGAAGCTGTATGACTCGA GTCATACAGCTTCATGAAGTGCTTTTT |
| 17 | GCACAGTTATCGGCAGTAACACTCGAG TGTTACTGCCGATAACTGTGCTTTTT |
| 18 | GGAGGCAAGTTGACAGGATCTCTCGAG AGATCCTGTCAACTTGCCTCCTTTTT |
| 19 | TCGACGTCAACTACGAGAAACCTCGAG GTTTCTCGTAGTTGACGTCGATTTTT |
| 20 | GCCCTTGGAAACATGTATGAACTCGAG TTCATACATGTTTCCAAGGGCTTTTT |

The *Homo sapiens* and *Mus musculus* PARP1 shRNA oligonucleotide sequences outlined in this Example were used in conjunction with the lentiviral vector system discussed herein.

An experimental therapeutic vector was designed as shown in FIG. 1A (linear form), and FIGS. 1C and 1D (circularized forms). Referring to the circularized vector map shown in FIGS. 1C and 1D, the experimental therapeutic vector includes: a hybrid 5' long terminal repeat (RSV/5' LTR) (SEQ ID NOS: 21-22), a HIV gag (SEQ ID NO: 23), a RRE (Rev-response element) (SEQ ID NO: 24), a Env element (SEQ ID NO: 25), a cPPT (SEQ ID NO: 26), a H1 promoter (SEQ ID NO: 27), a shRNA targeting PARP1 (shPARP1) (SEQ ID NOS: 6-10), a EF1 promoter (SEQ ID NO: 28), a GFP element (SEQ ID NO: 29), a Woodchuck Post-Transcriptional Regulatory Element (WPRE) (SEQ ID NO: 30), and a 3' LTR delta U3 (SEQ ID NO: 31). The presence of GFP is for experimental purposes due to its usefulness in demonstrating transduction in in vitro and in vivo model systems.

Further, referring to circularized vector maps shown in FIGS. 1E and 1F, a therapeutic or lentiviral vector has been designed which includes: a hybrid 5' long terminal repeat (RSV/5' LTR) (SEQ ID NOS: 21-22), a HIV gag (SEQ ID NO: 23), a RRE (Rev-response element) (SEQ ID NO: 24), a Env element (SEQ ID NO: 25), a cPPT (SEQ ID NO: 26), a H1 promoter (SEQ ID NO: 27), a shRNA targeting PARP1 (shPARP1) (SEQ ID NOS: 6-10), a Woodchuck Post-Transcriptional Regulatory Element (WPRE) (SEQ ID NO: 30), and a 3' LTR delta U3 (SEQ ID NO: 31). The therapeutic or lentiviral vector detailed in FIGS. 1E and 1F does not contain GFP.

Example 3. shRNA-Mediated Decrease of PARP1 Protein Expression shRNAs designed against *Homo sapiens* PARP1 were tested for their ability to downregulate PARP1 gene expression. The lentiviral vector containing human PARP1 shRNA was packaged as lentiviral particles. Lentiviral particles at a MOI of 1-10 were added to human U251 glioblastoma cells. After 48 hours, cells were lysed and PARP1 expression was measured by immunoblot analysis with a PARP1 specific antibody.

As shown in Table 5 below, five of the shRNAs designed against PARP1 showed an ability to downregulate PARP1 protein expression. Compared to a 100% control shRNA sequence: Sequence 6 (SEQ ID NO: 6) resulted in 57.1% of PARP1 protein expression; Sequence 7 (SEQ ID NO: 7) resulted in 45.8% of PARP1 protein expression; Sequence 8 (SEQ ID NO: 8) resulted in 47.2% of PARP1 protein expression; Sequence 9 (SEQ ID NO: 9) resulted in 48.8% of PARP1 protein expression; and Sequence 10 (SEQ ID NO: 10) resulted in 27.1% of PARP1 protein expression.

TABLE 5 shRNA-mediated downregulation of *Homo sapiens* PARP1

| shRNA against *Homo sapiens* PARP1 | Percentage protein expression (Control shRNA = 100%) after transduction with lentivirus expressing shRNA |
|---|---|
| Control shRNA Sequence (SEQ ID NO: 61) | 100 |
| Human PARP1 Sequence 6 (SEQ ID NO: 6) | 57.1 |
| Human PARP1 Sequence 7 (SEQ ID NO: 7) | 45.8 |
| Human PARP1 Sequence 8 (SEQ ID NO: 8) | 47.2 |
| Human PARP1 Sequence 9 (SEQ ID NO: 9) | 48.8 |
| Human PARP1 Sequence 10 (SEQ ID NO: 10) | 27.1 | shRNAs designed against *Mus musculus* PARP1 were tested for their ability to downregulate PARP1 gene expression. The lentiviral vector containing mouse PARP1 shRNA was packaged as lentiviral particles. Lentiviral particles at a MOI of 1-10 was added to mouse Hepa1-6 hepatoma cells. After 48 hours, cells were lysed and PARP1 expression was measured by immunoblot analysis with a PARP1 specific antibody. As shown in Table 6 below, five of the shRNAs designed against PARP1 showed an ability to downregulate PARP1 protein expression. Compared to a 100% control shRNA sequence: Sequence 16 (SEQ ID NO: 16) resulted in 22.8% of PARP1 protein expression; Sequence 17 (SEQ ID NO: 17) resulted in 47.7% of PARP1 protein expression; Sequence 18 (SEQ ID NO: 18) resulted in 2% of PARP1 protein expression; Sequence 19 (SEQ ID NO:19) resulted in 0.2% of PARP1 protein expression; and Sequence 20 (SEQ ID NO: 20) resulted in 2% of PARP1 protein expression.

TABLE 6 shRNA-mediated downregulation of *Mus musculus* PARP1

| shRNA against *Mus musculus* PARP1 | Percentage protein expression (Control shRNA = 100%) after transduction with lentivirus expressing shRNA |
|---|---|
| Control shRNA Sequence (SEQ ID NO: 61) | 100 |
| Mouse PARP1 Sequence 16 (SEQ ID NO: 16) | 22.8 |
| Mouse PARP1 Sequence 17 (SEQ ID NO: 17) | 47.7 |
| Mouse PARP1 Sequence 18 (SEQ ID NO: 18) | 2 |
| Mouse PARP1 Sequence 19 (SEQ ID NO: 19) | 0.2 |
| Mouse PARP1 Sequence 20 (SEQ ID NO: 20) | 2 |

Figure 2:
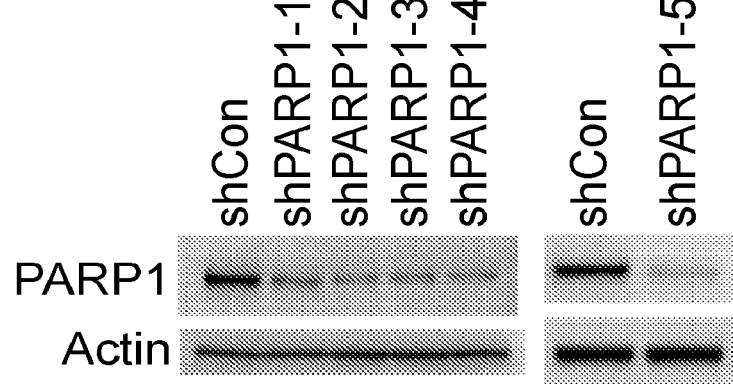
FIG. 2 depicts results from a knockdown experiment involving PARP1 in human cells.

PARP1 protein expression was found to be reduced in human and mouse cells following shRNA administration. Referring first to FIG. 2, a reduction in PARP1 protein in U251 human glioblastoma cell lines is demonstrated following treatment with lentivirus vectors expressing shRNA. The cell line U251 contains measurable PARP1 protein in cell lysates as indicated in the lanes identified as shCon (i.e., a lentivirus vector containing an irrelevant shRNA sequence that does not affect PARP1 protein expression). Individual shRNA sequences 6-10 (as referred to in Table 2 herein) were cloned into lentivirus vectors, expressed as infectious virus particles and used to transduce U251 cells. 48 hours after transduction, cells were lysed, proteins were separated by polyacrylamide gel electrophoresis and detected by immunoblot assay using anti-PARP1 antibody (Cell Signaling Technology).

Still referring to FIG. 2, Sequence 6 corresponds with lane shPARP1-1; Sequence 7 corresponds with lane shPARP1-2; Sequence 8 corresponds with lane shPARP1-3; Sequence 9 corresponds with lane shPARP1-4; and Sequence 10 corresponds with lane shPARP1-5. The housekeeping protein Actin was detected with Anti-Actin antibody (Sigma-Aldrich) to confirm that similar amounts of protein were analyzed in each lane of the gel. Sequence 10 was identified as being the most effective for reducing PARP1 protein in human U251 cells.

Figure 3:
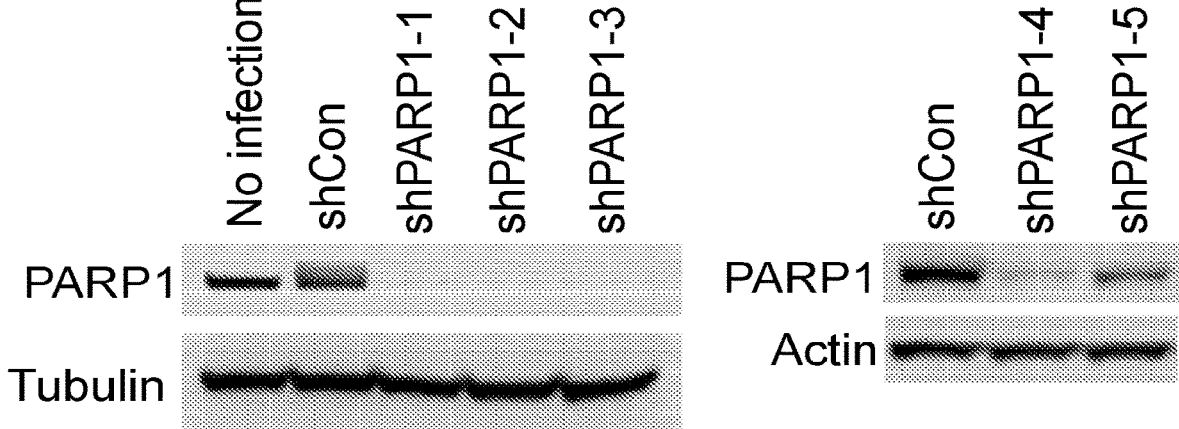
FIG. 3 depicts results from a knockdown experiment involving PARP1 in mouse cells.

Turning to mouse cell experiments, and with reference to FIG. 3, a reduction in PARP1 protein levels in Hepa1-6 mouse hepatoma cells was observed following administration of lentivirus vectors expressing shRNAs. The cell line Hepa1-6 contains measurable PARP1 protein in cell lysates as indicated in lanes identified as No infection (no lentivirus used) or shCon (lentivirus vector containing an irrelevant shRNA sequence that does not affect PARP1 protein expression). Individual shRNA constructs 16-20 (as referred to in Table 4 herein) were cloned into lentivirus vectors, expressed as infectious virus particles and used to transduce Hepa1-6 cells. 48 hours after transduction, cells were lysed, proteins were separated by polyacrylamide gel electrophoresis and detected by immunoblot assay using anti-PARP1 antibody (Cell Signaling Technology). Still referring to FIG. 3, Sequence 16 corresponds with lane shPARP1-1; Sequence 17 corresponds with lane shPARP1-2; Sequence 18 corresponds with lane shPARP1-3; Sequence 19 corresponds with lane shPARP1-4; and Sequence 20 corresponds with lane shPARP1-5. The housekeeping proteins Actin or Tubulin were detected with antibody reagents (Sigma-Aldrich) as controls for the amount of protein loaded in each lane of the gel. shRNA 16, 17 and 18 were potent for inhibiting PARP1 protein expression. Sequence 19 was identified as being most effective for reducing PARP1 protein in murine Hepa1-6.

Example 4. Lentiviral Vector Transduction in Mouse Neurons

Figure 4:
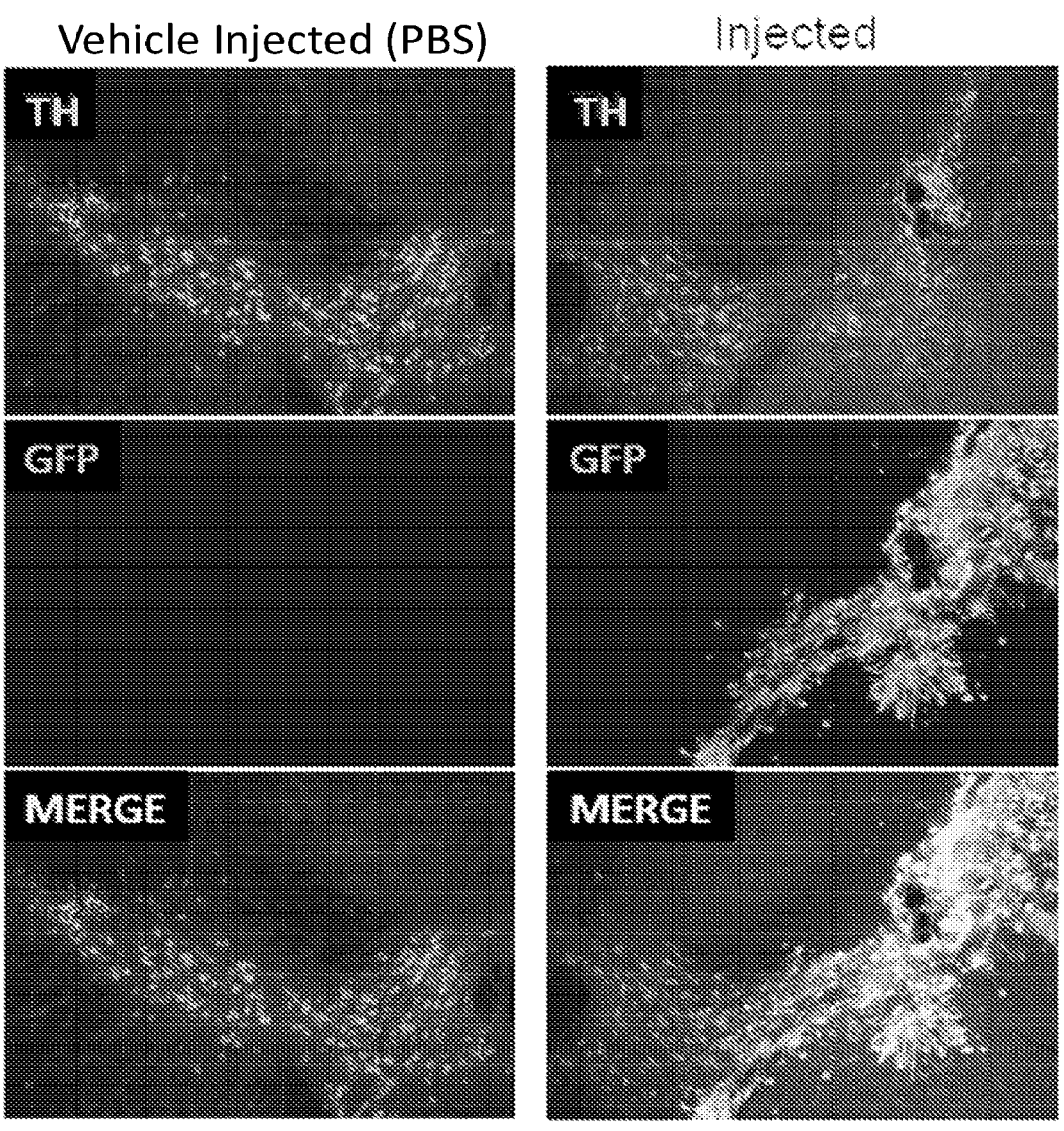
FIG. 4 depicts neurons transduced with an exemplary lentiviral vector.

The lentiviral vector system outlined herein has been found to be capable of transduction in mouse neurons. With reference to FIG. 4, wild-type mice were injected with mock (no lentivirus) in the left column of micrographs or LV-shPARP1 also expressing green fluorescence protein in the right column of micrographs, via a steel needle inserted into the substantia nigra region of the mouse brain. The LV-shPARP1-GFP was dosed at 0.1 ml containing approximately $1 \times 10^8$ transducing units. 14 days later, mice were sacrificed and the substantia nigra region was excised from the brain, fixed in formaldehyde, and embedded in paraffin. Thin sections were mounted on glass slides and visualized with a fluorescence microscope. TH+ neurons (expressing high levels of tyrosine hydroxylase) generally identify the substantia nigra region and appear red (or white in gray-scale photographs) in FIG. 4. The middle panels depict cells that were transduced with mock (left column) or LV-shPARP1-GFP (see: green [or white in gray-scale photographs] staining in right column). Due to the high intensity of light emitted by GFP, indicating efficient transduction and transgene expression, positively transduced neurons appeared black in this figure and were not present, as expected, in the sham control (left column). The lower panels merge the TH+ neuron staining and GFP+ neuron staining from lentivirus transductions to demonstrate the presence of transduced cells within the substantia nigra including within TH+ neurons.

Example 5. Therapeutic Treatment of Neuronal Death Using Lentiviral Vector System The chemical neurotoxin 1-Methyl-4-phenyl-1,2,3,6-tetrahydropyridine (MPTP) causes severe and irreversible motor abnormalities in mice, and is widely used to model human PD. See, e.g., Kopin & Markey, 11 *Annu. Rev. Neurosci,* 81-96 (1988). Treating mice with MPTP lowers the levels of striatal dopamine and its metabolites, because drug neurotoxicity reduces the number of dopamine producing cells in the substantia nigra. The model has been used to test the protective effects of compounds including nitric oxide, which prevent neuronal death after MPTP exposure. See, e.g., Przedborski et al., 93 *Proc. Natl. Acad. Sci. U.S.A.,* 44565-4571 (1996). This model can be employed to measure the potential for preventing death of dopaminergic neurons by pretreating mice with lentivirus vector designed to express a short hairpin RNA sequence (sh) that will reduce neuronal cell expression of PARP (LV-shPARP). The vector can be further modified to express the green fluorescence protein marker that will identify transduced cells (LV-shPARP-GFP) and is compared to a vector that does not express shPARP (LV-GFP).

Suspensions of LV-shPARP-GFP or LV-GFP are injected into the substantia nigra of healthy adult mice. Doses are escalated until a toxic level is reached, which results in severe motor impairment or death of the mouse. Using the maximum tolerated dose, mice are treated with LV-shPARP-GFP or control vector. Two weeks later, sentinel animals from each group are sacrificed to confirm transduction of neurons in the substantia nigra. The remaining animals (in groups of 10) are treated with MPTP-HCl, 20 mg/kg dose in saline given four times via intraperitoneal injection with 2 hour intervals. Between 2 and 7 days later, groups of mice are sacrificed, the brain is removed, fixed and embedded in paraffin for sectioning. The substantia nigra region is identified by staining for tyrosine hydroxylase-expressing neurons (TH+) and transduced neurons are identified by expression of GFP. Therapeutic impact of LV-shPARP-GFP is determined by counting the numbers of TH+ or GFP+ neurons in substantia nigra from mice treated with LV-shPARP-GFP or control vector. MPTP is expected to destroy much of the substantia nigra TH+ cells and LV-shPARP-GFP is expected to protect these cells and preserve normal appearance of the substantia nigra. In additional groups of mice treated in the same way with both LV vectors and MPTP, the brains are removed at 7 days after MPTP dosing, the substantia nigra region is isolated by dissection and tissue is frozen at −80 degrees Celsius. Subsequently, the tissue specimens are thawed and dopamine is extracted according to published methods (see: Przedborski et al., infra). LV-shPARP-GFP is expected to preserve normal levels of dopamine production after MPTP treatment, and dopamine levels will be significantly higher in mice treated with LV-shPARP-GFP than mice treated with control vector.

Example 6. Lentiviral Targeting to Neurons Using Variants of Envelope Glycoproteins Properties of individual envelope glycoproteins impact tissue tropism and the efficiency of delivery of therapeutic genes to the sites of disease. To treat PD, a target for gene therapy is a TH+ cell of the substantia nigra. To optimize targeting to a TH+ cell, various envelope glycoproteins will be compared for their role in improving transduction efficiencies in the TH+ cells of the mouse substantia nigra. As described above in Example 1, an envelope plasmid has been designed and produced which contains the vesicular stomatitis virus G glycoprotein (VSV-G). This envelope plasmid can be compared to other designed envelope plasmids which, in place of VSV-G, includes FUG-C(N-terminal region of rabies virus glycoprotein), gp64 envelope glycoprotein from baculovirus, envelope glycoprotein from baboon endogenous virus or other suitable alternatives for packaging lentivirus particles. In each case, using the envelope plasmid variants, lentivirus vector stocks are produced, injected into mouse brains, and the efficiency of transduction into TH+ cells of the mouse substantia nigra is examined.

Example 7. Testing PARP Genes for Therapeutic Effect of PD

The studies described herein include a focus on PARP1 and how its modulation can be used to therapeutically treat PD. However, PARP1 is only 1 of approximately 16 closely related PARP genes with similar functions. Using the techniques for target identification, shRNA production and conversion into lentivirus-delivered miRNA as described herein, the other PARP genes can be tested for their ability to be effective therapeutic vectors in treating PD. Briefly, lentiviral vectors containing the other PARP genes can be injected into a mouse to test for PD correction using the methods, techniques and materials described herein.

Example 8. Method of Designing Synthetic miRNAs for Insertion into a Lentiviral Vector System Target short-hairpin sequences that are 19-22 nucleotides long are chosen from a shRNA design program such as, for example, the Invitrogen Block-iT RNAi designer or the RNAi design program from the Broad Institute (MIT). Several sequences are tested for efficient knockdown of a particular gene, such as, for example, PARP. A shRNA sequence that decreases the target gene expression at least 80% is then inserted within a defined microRNA hairpin backbone. MicroRNA (miRNA) hairpin structures can be obtained from the miRBase.org website.

The chosen shRNA sequence is then inserted within the hairpin structure while leaving the loop sequence unchanged. The antisense shRNA sequence is inserted within the 5-prime sequence of the miRNA hairpin to become the seed sequence for gene targeting. The sense shRNA sequence is modified according to the particular miRNA hairpin structure chosen. As an example, nucleotides 9 and 10 of the sense strand are removed for the miR30 hairpin structure. A miR sequence containing a target sequence such as PARP and a backbone sequence are synthesized with BsrGI and NotI restriction sites by either MWG Operon or IDT. This sequence is inserted into the BsrG1 and NotI sites of the miR-acceptor lentiviral vector.

Example 9. Treatment of Human Patients with PD

Twelve patients aged 35-75 years at least 5 years after initial diagnosis of PD receive bilateral, stereotactic, intra-putaminal injections of LV-shPARP compositions (based, for example, on the lentiviral construct shown in FIG. 1B) as described herein (cGMP grade) in a dose escalation study. The likely dose range is $10^8$ transducing units of LV-shPARP in 5 ml of sterile saline [1 transducing unit is the amount of LV-shPARP required to achieve on average, 1 copy of the transgene integrated into the chromosome of a single target cell]. The upper range is expected to be approximately $10^{10}$ transducing units of LV-shPARP. Treated patients are followed for at least 1 year and up to 5 years for changes in locomotor status.

Changes in clinical status are determined using the Unified Parkinson's Disease Rating Scale, comparing LV-treated to off medication status for a matched group of patients with PD. Patients are also asked to record clinical status in terms of time without troubling dyskinesia, and may also undergo testing with the Purdue pegboard test of hand dexterity, and activities of daily living score. See, e.g., Marks Jr., et al., 9(12) *Lancet Neurol.*, 1164-72 (2010). Patient outcomes after LV-shPARP therapy are compared to previous gene therapy trials testing Adeno-associated virus delivery of glutamic acid decarboxylase gene or aromatic L-amino acid decarboxylase to increase L-DOPA production or studies using Adeno-associated virus delivery of neurotrophic growth factor neurturin. See, e.g., Kaplitt et al. 369 (9579) *Lancet Neurol.* 2097-105 (2007); see also Christine et al., 73(20) *Neurology*, 1662-9, (2009). It is rationally predicted that subjects receiving LV-shPARP compositions show improvements in PD and PD-related symptoms.

The disclosure of the above example embodiments is intended to be illustrative, but not limiting, of the scope of the inventions, which are set forth in the following claims and their equivalents. Although exemplary embodiments of the inventions have been described in some detail for purposes of clarity of understanding, it will be apparent that certain changes and modifications can be practiced within the scope of the following claims. In the following claims, elements and/or steps do not imply any particular order of operation, unless explicitly stated in the claims or implicitly required by the disclosure.

| | | Sequences |
|---|---|---|
| SEQ ID NO: | Description | Sequence |
| 1 | *Homo sapiens* PARP1 Target Sequence 1 | CTTCGTTAGAATGTCTGCCTT |
| 2 | *Homo sapiens* PARP1 Target Sequence 2 | GCAGCTTCATAACCGAAGATT |
| 3 | *Homo sapiens* PARP1 Target Sequence 3 | CCGAGAAATCTCTTACCTCAA |
| 4 | *Homo sapiens* PARP1 Target Sequence 4 | CGACCTGATCTGGAACATCAA |
| 5 | *Homo sapiens* PARP1 Target Sequence 5 | GTTGCTGATGGGTAGTACC |
| 6 | *Homo sapiens* PARP1 shRNA Oligonucleotide Sequence 1 | CTTCGTTAGAATGTCTGCCTTCTCGAGAAGGCAGACAT TCTAACGAAGTTTTT |
| 7 | *Homo sapiens* PARP1 shRNA Oligonucleotide Sequence 2 | GCAGCTTCATAACCGAAGATTCTCGAGAATCTTCGGTT ATGAAGCTGCTTTTT |
| 8 | *Homo sapiens* PARP1 shRNA Oligonucleotide Sequence 3 | CCGAGAAATCTCTTACCTCAACTCGAGTTGAGGTAAGA GATTTCTCGGTTTTT |

-continued

| | Sequences | |
|---|---|---|

| SEQ ID NO: | Description | Sequence |
|---|---|---|
| 9 | *Homo sapiens* PARP1 shRNA Oligonucleotide Sequence 4 | CGACCTGATCTGGAACATCAACTCGAGTTGATGTTCCA GATCAGGTCGTTTTT |
| 10 | *Homo sapiens* PARP1 shRNA Oligonucleotide Sequence 5 | GTTGCTGATGGGTAGTACCTTCAAGAGAGGTACTACCC ATCAGCAACTTTTT |
| 11 | *Mus musculus* PARP1 Target Sequence 1 | GCACTTCATGAAGCTGTATGA |
| 12 | *Mus musculus* PARP1 Target Sequence 2 | GCACAGTTATCGGCAGTAACA |
| 13 | *Mus musculus* PARP1 Target Sequence 3 | GGAGGCAAGTTGACAGGATCT |
| 14 | *Mus musculus* PARP1 Target Sequence 4 | TCGACGTCAACTACGAGAAAC |
| 15 | *Mus musculus* PARP1 Target Sequence 5 | GCCCTTGGAAACATGTATGAA |
| 16 | *Mus musculus* PARP1 shRNA Oligonucleotide Sequence 1 | GCACTTCATGAAGCTGTATGACTCGAGTCATACAGCTT CATGAAGTGCTTTTT |
| 17 | *Mus musculus* PARP1 shRNA Oligonucleotide Sequence 2 | GCACAGTTATCGGCAGTAACACTCGAGTGTTACTGCCG ATAACTGTGCTTTTT |
| 18 | *Mus musculus* PARP1 shRNA Oligonucleotide Sequence 3 | GGAGGCAAGTTGACAGGATCTCTCGAGAGATCCTGTC AACTTGCCTCCTTTTT |
| 19 | *Mus musculus* PARP1 shRNA Oligonucleotide Sequence 4 | TCGACGTCAACTACGAGAAACCTCGAGGTTTCTCGTAG TTGACGTCGATTTTT |
| 20 | *Mus musculus* PARP1 shRNA Oligonucleotide Sequence 5 | GCCCTTGGAAACATGTATGAACTCGAGTTCATACATGT TTCCAAGGGCTTTTT |
| 21 | Rous Sarcoma virus (RSV) promoter | GTAGTCTTATGCAATACTCTTGTAGTCTTGCAACATGGT AACGATGAGTTAGCAACATGCCTTACAAGGAGAGAAA AAGCACCGTGCATGCCGATTGGTGGAAGTAAGGTGGTA CGATCGTGCCTTATTAGGAAGGCAACAGACGGGTCTGA CATGGATTGGACGAACCACTGAATTGCCGCATTGCAGA GATATTGTATTTAAGTGCCTAGCTCGATACAATAAACG |
| 22 | 5' Long terminal repeat (LTR) | GGTCTCTCTGGTTAGACCAGATCTGAGCCTGGGAGCTC TCTGGCTAACTAGGGAACCCACTGCTTAAGCCTCAATA AAGCTTGCCTTGAGTGCTTCAAGTAGTGTGTGCCCGTCT GTTGTGTGACTCTGGTAACTAGAGATCCCTCAGACCCTT TTAGTCAGTGTGGAAAATCTCTAGCA |
| 23 | Helper/Rev; HIV Gag; Viral capsid | ATGGGTGCGAGAGCGTCAGTATTAAGCGGGGGAGAAT TAGATCGATGGGAAAAAATTCGGTTAAGGCCAGGGGG AAAGAAAAAATATAAATTAAAACATATAGTATGGGCA AGCAGGGAGCTAGAACGATTCGCAGTTAATCCTGGCCT |

-continued

| Sequences | |
|---|---|
| SEQ ID NO: Description | Sequence |

GTTAGAAACATCAGAAGGCTGTAGACAAATACTGGGA
CAGCTACAACCATCCCTTCAGACAGGATCAGAAGAACT
TAGATCATTATATAATACAGTAGCAACCCTCTATTGTGT
GCATCAAAGGATAGAGATAAAAGACACCAAGGAAGCT
TTAGACAAGATAGAGGAAGAGCAAAACAAAAGTAAGA
AAAAAGCACAGCAAGCAGCAGCTGACACAGGACACAG
CAATCAGGTCAGCCAAAATTACCCTATAGTGCAGAACA
TCCAGGGGCAAATGGTACATCAGGCCATATCACCTAGA
ACTTTAAATGCATGGGTAAAAGTAGTAGAAGAGAAGG
CTTTCAGCCCAGAAGTGATACCCATGTTTTCAGCATTAT
CAGAAGGAGCCACCCCACAAGATTTAAACACCATGCTA
AACACAGTGGGGGGACATCAAGCAGCCATGCAAATGT
TAAAAGAGACCATCAATGAGGAAGCTGCAGAATGGGA
TAGAGTGCATCCAGTGCATGCAGGGCCTATTGCACCAG
GCCAGATGAGAGAACCAAGGGGAAGTGACATAGCAGG
AACTACTAGTACCCTTCAGGAACAAATAGGATGGATGA
CACATAATCCACCTATCCCAGTAGGAGAAATCTATAAA
AGATGGATAATCCTGGGATTAAATAAAATAGTAAGAAT
GTATAGCCCTACCAGCATTCTGGACATAAGACAAGGAC
CAAAGGAACCCTTTAGAGACTATGTAGACCGATTCTAT
AAAACTCTAAGAGCCGAGCAAGCTTCACAAGAGGTAA
AAAATTGGATGACAGAAACCTTGTTGGTCCAAAATGCG
AACCCAGATTGTAAGACTATTTTAAAAGCATTGGGACC
AGGAGCGACACTAGAAGAAATGATGACAGCATGTCAG
GGAGTGGGGGGACCCGGCCATAAAGCAAGAGTTTTGG
CTGAAGCAATGAGCCAAGTAACAAATCCAGCTACCATA
ATGATACAGAAAGGCAATTTTAGGAACCAAAGAAAGA
CTGTTAAGTGTTTCAATTGTGGCAAAGAAGGGCACATA
GCCAAAAATTGCAGGGCCCCTAGGAAAAAGGGCTGTT
GGAAATGTGGAAAGGAAGGACACCAAATGAAAGATTG
TACTGAGAGACAGGCTAATTTTTTAGGGAAGATCTGGC
CTTCCCACAAGGGAAGGCCAGGGAATTTTCTTCAGAGC
AGACCAGAGCCAACAGCCCCACCAGAAGAGAGCTTCA
GGTTTGGGGAAGAGACAACAACTCCCTCTCAGAAGCAG
GAGCCGATAGACAAGGAACTGTATCCTTTAGCTTCCCT
CAGATCACTCTTTGGCAGCGACCCCTCGTCACAATAA

24 Rev response element (RRE)
AGGAGCTTTGTTCCTTGGGTTCTTGGGAGCAGCAGGAA
GCACTATGGGCGCAGCCTCAATGACGCTGACGGTACAG
GCCAGACAATTATTGTCTGGTATAGTGCAGCAGCAGAA
CAATTTGCTGAGGGCTATTGAGGCGCAACAGCATCTGT
TGCAACTCACAGTCTGGGGCATCAAGCAGCTCCAGGCA
AGAATCCTGGCTGTGGAAAGATACCTAAAGGATCAACA
GCTCC 25 Envelope; VSV-G; Glycoprotein envelope-cell entry
ATGAAGTGCCTTTTGTACTTAGCCTTTTTATTCATTGGG
GTGAATTGCAAGTTCACCATAGTTTTTCCACACAACCA
AAAAGGAAACTGGAAAAATGTTCCTTCTAATTACCATT
ATTGCCCGTCAAGCTCAGATTTAAATTGGCATAATGAC
TTAATAGGCACAGCCTTACAAGTCAAAATGCCCAAGAG
TCACAAGGCTATTCAAGCAGACGGTTGGATGTGTCATG
CTTCCAAATGGGTCACTACTTGTGATTTCCGCTGGTATG
GACCGAAGTATATAACACATTCCATCCGATCCTTCACT
CCATCTGTAGAACAATGCAAGGAAAGCATTGAACAAA
CGAAACAAGGAACTTGGCTGAATCCAGGCTTCCCTCCT
CAAAGTTGTGGATATGCAACTGTGACGGATGCCGAAGC
AGTGATTGTCCAGGTGACTCCTCACCCATGTGCTGGTTG
ATGAATACACAGGAGAATGGGTTGATTCACAGTTCATC
AACGGAAAATGCAGCAATTACATATGCCCCACTGTCCA
TAACTCTACAACCTGGCATTCTGACTATAAGGTCAAAG
GGCTATGTGATTCTAACCTCATTTCCATGGACATCACCT
TCTTCTCAGAGGACGGAGAGCTATCATCCCTGGGAAAG
GAGGGCACAGGGTTCAGAAGTAACTACTTTGCTTATGA
AACTGGAGGCAAGGCCTGCAAAATGCAATACTGCAAG
CATTGGGGGAGTCAGACTCCCATCAGGTGTCTGGTTCGA
GATGGCTGATAAGGATCTCTTTGCTGCAGCCAGATTCC
CTGAATGCCCAGAAGGGTCAAGTATCTCTGCTCCATCT
CAGACCTCAGTGGATGTAAGTCTAATTCAGGACGTTGA
GAGGATCTTGGATTATTCCCTCTGCCAAGAAACCTGGA
GCAAATCAGAGCGGGTCTTCCAATCTCTCCAGTGGAT
CTCAGCTATCTTGCTCCTAAAAACCCAGGAACCGGTCC
TGCTTTCACCATAATCAATGGTACCCTAAAATACTTTGA
GACCAGATACATCAGAGTCGATATTGCTGCTCCAATCC -continued

| | | Sequences |
|---|---|---|

| SEQ ID NO: | Description | Sequence |
|---|---|---|
| | | TCTCAAGAATGGTCGGAATGATCAGTGGAACTACCACA GAAAGGGAACTGTGGGATGACTGGGCACCATATGAAG ACGTGGAAATTGGACCCAATGGAGTTCTGAGGACCAGT TCAGGATATAAGTTTCCTTTATACATGATTGGACATGGT ATGTTGGACTCCGATCTTCATCTTAGCTCAAAGGCTCAG GTGTTCGAACATCCTCACATTCAAGACGCTGCTTCGCA ACTTCCTGATGATGAGAGTTTATTTTTTGGTGATACTGG GCTATCCAAAAATCCAATCGAGCTTGTAGAAGGTTGGT TCAGTAGTTGGAAAAGCTCTATTGCCTCTTTTTTCTTTA TCATAGGGTTAATCATTGGACTATTCTTGGTTCTCCGAG TTGGTATCCATCTTTGCATTAAATTAAAGCACACCAAG AAAAGACAGATTTATACAGACATAGAGATGA |
| 26 | Central polypurine tract (cPPT) | TTTTAAAAGAAAAGGGGGGATTGGGGGGTACAGTGCA GGGGAAAGAATAGTAGACATAATAGCAACAGACATAC AAACTAAAGAATTACAAAAACAAATTACAAAATTCAA AATTTTA |
| 27 | Polymerase III shRNA promoters; H1 promoter | GAACGCTGACGTCATCAACCCGCTCCAAGGAATCGCGG GCCCAGTGTCACTAGGCGGGAACACCCAGCGCGCGTGC GCCCTGGCAGGAAGATGGCTGTGAGGGACAGGGGAGT GGCGCCCTGCAATATTTGCATGTCGCTATGTGTTCTGGG AAATCACCATAAACGTGAAATGTCTTTGGATTTGGGAA TCTTATAAGTTCTGTATGAGACCACTT |
| 28 | EF1 | GCTCCGGTGCCCGTCAGTGGGCAGAGCGCACATCGCCC ACAGTCCCCGAGAAGTTGGGGGGGAGGGGTCGGCAATT GAACGGGTGCCTAGAGAAGGTGGCGCGGGGTAAACTG GGAAAGTGATGTCGTGTACTGGCTCCGCCTTTTTCCCGA GGGTGGGGGAGAACCGTATATAAGTGCAGTAGTCGCC GTGAACGTTCTTTTTCGCAACGGGTTTGCCGCCAGAAC ACAGCTGAAGCTTCGAGGGGCTCGCATCTCTCCTTCAC GCGCCCGCCGCCCTACCTGAGGCCGCCATCCACGCCGG TTGAGTCGCGTTCTGCCGCCTCCCGCCTGTGGTGCCTCC TGAACTGCGTCCGCCGTCTAGGTAAGTTTAAAGCTCAG GTCGAGACCGGGCCTTTGTCCGGCGCTCCCTTGGAGCC TACCTAGACTCAGCCGGCTCTCCACGCTTTGCCTGACCC TGCTTGCTCAACTCTACGTCTTTGTTTCGTTTTCTGTTCT GCGCCGTTACAGATCCAAGCTGTGACCGGCGCCTAC |
| 29 | GFP | ATGGAGAGCGACGAGAGCGGCCTGCCCGCCATGGAGA TCGAGTGCCGCATCACCGGCACCCTGAACGGCGTGGAG TTCGAGCTGGTGGGCGGCGGAGAGGGCACCCCCAAGC AGGGCCGCATGACCAACAAGATGAAGAGCACCAAAGG CGCCCTGACCTTCAGCCCCTACCTGCTGAGCCACGTGA TGGGCTACGGCTTCTACCACTTCGGCACCTACCCCAGC GGCTACGAGAACCCCTTCCTGCACGCCATCAACAACGG CGGCTACACCAACACCCGCATCGAGAAGTACGAGGAC GGCGGCGTGCTGCACGTGAGCTTCAGCTACCGCTACGA GGCCGGCCGCGTGATCGGCGACTTCAAGGTGGTGGGCA CCGGCTTCCCCGAGGACAGCGTGATCTTCACCGACAAG ATCATCCGCAGCAACGCCACCGTGGAGCACCTGCACCC CATGGGCGATAACGTGCTGGTGGGCAGCTTCGCCCGCA CCTTCAGCCTGCGCGACGGCGGCTACTACAGCTTCGTG GTGGACAGCCACATGCACTTCAAGAGCGCCATCCACCC CAGCATCCTGCAGAACGGGGGCCCCATGTTCGCCTTCC GCCGCGTGGAGGAGCTGCACAGCAACACCGAGCTGGG CATCGTGGAGTACCAGCACGCCTTCAAGACCCCCATCG CCTTCGCCAGATCCCGCGCTCAGTCGTCCAATTCTGCCG TGGACGGCACCGCCGGACCCGGCTCCACCGGATCTCGC TAA |
| 30 | Long WPRE sequence | AATCAACCTCTGATTACAAAATTTGTGAAAGATTGACT GGTATTCTTAACTATGTTGCTCCTTTTACGCTATGTGGA TACGCTGCTTTAATGCCTTTGTATCATGCTATTGCTTCC CGTATGGCTTTCATTTTCTCCTCCTTGTATAAATCCTGG TTGCTGTCTCTTTATGAGGAGTTGTGGCCCGTTGTCAGG CAACGTGGCGTGGTGTGCACTGTGTTTGCTGACGCAAC CCCCACTGGTTGGGGCATTGCCACCACCTGTCAGCTCCT TTCCGGGACTTTCGCTTTCCCCCTCCCTATTGCCACGGC GGAACTCATCGCCGCCTGCCTTGCCCGCTGCTGGACAG GGGCTCGGCTGTTGGGCACTGACAATTCCGTGGTGTTG TCGGGGAAATCATCGTCCTTTCCTTGGCTGCTCGCCTGT |

-continued

| | | Sequences |
|---|---|---|

| SEQ ID NO: | Description | Sequence |
|---|---|---|
| | | GTTGCCACCTGGATTCTGCGCGGGACGTCCTTCTGCTAC GTCCCTTCGGCCCTCAATCCAGCGGACCTTCCTTCCCGC GGCCTGCTGCCGGCTCTGCGGCCTCTTCCGCGTCTTCGC CTTCGCCCTCAGACGAGTCGGATCTCCCTTTGGGCCGCC TCCCCGCCT |
| 31 | 3' delta LTR | TGGAAGGGCTAATTCACTCCCAACGAAGATAAGATCTG CTTTTTGCTTGTACTGGGTCTCTCTGGTTAGACCAGATC TGAGCCTGGGAGCTCTCTGGCTAACTAGGGAACCCACT GCTTAAGCCTCAATAAAGCTTGCCTTGAGTGCTTCAAG TAGTGTGTGCCCGTCTGTTGTGTGACTCTGGTAACTAGA GATCCCTCAGACCCTTTTAGTCAGTGTGGAAAATCTCTA GCAGTAGTAGTTCATGTCA |
| 32 | Helper/Rev; CMV early (CAG) enhancer; Enhance Transcription | TAGTTATTAATAGTAATCAATTACGGGGTCATTAGTTCA TAGCCCATATATGGAGTTCCGCGTTACATAACTTACGG TAAATGGCCCGCCTGGCTGACCGCCCAACGACCCCCGC CCATTGACGTCAATAATGACGTATGTTCCCATAGTAAC GCCAATAGGGACTTTCCATTGACGTCAATGGGTGGACT ATTTACGGTAAACTGCCCACTTGGCAGTACATCAAGTG TATCATATGCCAAGTACGCCCCCTATTGACGTCAATGA CGGTAAATGGCCCGCCTGGCATTATGCCCAGTACATGA CCTTATGGGACTTTCCTACTTGGCAGTACATCTACGTAT TAGTCATC |
| 33 | Helper/Rev; Chicken beta actin (CAG) promoter; Transcription | GCTATTACCATGGGTCGAGGTGAGCCCCACGTTCTGCT TCACTCTCCCCATCTCCCCCCCCTCCCCACCCCCAATTT TGTATTTATTTATTTTTTAATTATTTTGTGCAGCGATGG GGGCGGGGGGGGGGGGGGCGCGCGCCAGGCGGGGCGG GGCGGGGCGAGGGGCGGGGCGGGGCGAGGCGGAGAG GTGCGGCGGCAGCCAATCAGAGCGGCGCGCTCCGAAA GTTTCCTTTTATGGCGAGGCGGCGGCGGCGGCGGCCCT ATAAAAAGCGAAGCGCGCGGCGGGCG |
| 34 | Helper/Rev; Chicken beta actin intron; Enhance gene expression | GGAGTCGCTGCGTTGCCTTCGCCCCGTGCCCCGCTCCGC GCCGCCTCGCGCCGCCCGCCCCGGCTCTGACTGACCGC GTTACTCCCACAGGTGAGCGGGCGGGACGGCCCCTTCTC CTCCGGGCTGTAATTAGCGCTTGGTTTAATGACGGCTC GTTTCTTTTCTGTGGCTGCGTGAAAGCCTTAAAGGGCTC CGGGAGGGCCCTTTGTGCGGGGGGGAGCGGCTCGGGG GGTGCGTGCGTGTGTGTGTGCGTGGGGAGCGCCGCGTG CGGCCCGCGCTGCCCGGCGGCTGTGAGCGCTGCGGGCG CGGCGCGGGGCTTTGTGCGCTCCGCGTGTGCGCGAGGG GAGCGCGGCCGGGGGCGGTGCCCCGCGGTGCGGGGGG GCTGCGAGGGGAACAAAGGCTGCGTGCGGGGTGTGTG CGTGGGGGGGTGAGCAGGGGGTGTGGGCGCGGCGGTC GGGCTGTAACCCCCCCCTGCACCCCCCTCCCCGAGTTG CTGAGCACGGCCCGGCTTCGGGTGCGGGGCTCCGTGCG GGGCGTGGCGCGGGGCTCGCCGTGCCGGGCGGGGGGT GGCGGCAGGTGGGGGTGCCGGGCGGGGCGGGGCCGCC TCGGGCCGGGGAGGGCTCGGGGGAGGGGCGCGGCGGC CCCGGAGCGCCGGCGGCTGTCGAGGCGCGGCGAGCCG CAGCCATTGCCTTTTATGGTAATCGTGCGAGAGGGCGC AGGGACTTCCTTTGTCCCAAATCTGGCGGAGCCGAAAT CTGGGAGGCGCCGCCGCACCCCCTCTAGCGGGCGCGGG CGAAGCGGTGCGGCGCCGGCAGGAAGGAAATGGGCGG GGAGGGCCTTCGTGCGTCGCCGCGCCGCCGTCCCCTTC TCCATCTCCAGCCTCGGGGCTGCCGCAGGGGGACGGCT GCCTTCGGGGGGGACGGGGCAGGCGGGGTTCGGCTTC TGGCGTGTGACCGGCGG |
| 35 | Helper/Rev; HIV Pol; Protease and reverse transcriptase | ATGAATTTGCCAGGAAGATGGAAACCAAAAATGATAG GGGGAATTGGAGGTTTTATCAAAGTAGGACAGTATGAT CAGATACTCATAGAAATCTGCGGACATAAAGCTATAGG TACAGTATTAGTAGGACCTACACCTGTCAACATAATTG GAAGAAATCTGTTGACTCAGATTGGCTGCACTTTAAAT TTTCCCATTAGTCCTATTGAGACTGTACCAGTAAAATTA AAGCCAGGAATGGATGGCCCAAAAGTTAAACAATGGC CATTGACAGAAGAAAAAATAAAAGCATTAGTAGAAAT TTGTACAGAAATGGAAAAGGAAGGAAAAATTTCAAAA ATTGGGCCTGAAAATCCATACAATACTCCAGTATTTGC CATAAAGAAAAAGACAGTACTAAATGGAGAAAATTA GTAGATTTCAGAGAACTTAATAAGAGAACTCAAGATTT |

-continued

| | Sequences | |
| --- | --- | --- |

SEQ
ID
NO: Description          Sequence

CTGGGAAGTTCAATTAGGAATACCACATCCTGCAGGGT
TAAAACAGAAAAAATCAGTAACAGTACTGGATGTGGG
CGATGCATATTTTTCAGTTCCCTTAGATAAAGACTTCAG
GAAGTATACTGCATTTACCATACCTAGTATAAACAATG
AGACACCAGGGATTAGATATCAGTACAATGTGCTTCCA
CAGGGATGGAAAGGATCACCAGCAATATTCCAGTGTAG
CATGACAAAAATCTTAGAGCCTTTTAGAAAACAAAATC
CAGACATAGTCATCTATCAATACATGGATGATTTGTAT
GTAGGATCTGACTTAGAAATAGGGCAGCATAGAACAA
AAATAGAGGAACTGAGACAACATCTGTTGAGGTGGGG
ATTTACCACACCAGACAAAAAACATCAGAAAGAACCTC
CATTCCTTTGGATGGGTTATGAACTCCATCCTGATAAAT
GGACAGTACAGCCTATAGTGCTGCCAGAAAAGGACAG
CTGGACTGTCAATGACATACAGAAATTAGTGGGAAAAT
TGAATTGGGCAAGTCAGATTTATGCAGGGATTAAAGTA
AGGCAATTATGTAAACTTCTTAGGGGAACCAAAGCACT
AACAGAAGTAGTACCACTAACAGAAGAAGCAGAGCTA
GAACTGGCAGAAAACAGGGAGATTCTAAAAGAACCGG
TACATGGAGTGTATTATGACCCATCAAAAGACTTAATA
GCAGAAATACAGAAGCAGGGGCAAGGCCAATGGACAT
ATCAAATTTATCAAGAGCCATTTAAAAATCTGAAAACA
GGAAAATATGCAAGAATGAAGGGTGCCCACACTAATG
ATGTGAAACAATTAACAGAGGCAGTACAAAAAATAGC
CACAGAAAGCATAGTAATATGGGGAAAGACTCCTAAA
TTTAAATTACCCATACAAAAGGAAACATGGGAAGCATG
GTGGACAGAGTATTGGCAAGCCACCTGGATTCCTGAGT
GGGAGTTTGTCAATACCCCTCCCTTAGTGAAGTTATGGT
ACCAGTTAGAGAAAGAACCCATAATAGGAGCAGAAAC
TTTCTATGTAGATGGGGCAGCCAATAGGGAAACTAAAT
TAGGAAAAGCAGGATATGTAACTGACAGAGGAAGACA
AAAAGTTGTCCCCCTAACGGACACAACAAATCAGAAG
ACTGAGTTACAAGCAATTCATCTAGCTTTGCAGGATTC
GGGATTAGAAGTAAACATAGTGACAGACTCACAATATG
CATTGGGAATCATTCAAGCACAACCAGATAAGAGTGAA
TCAGAGTTAGTCAGTCAAATAATAGAGCAGTTAATAAA
AAAGGAAAAGTCTACCTGGCATGGGTACCAGCACAC
AAAGGAATTGGAGGAAATGAACAAGTAGATGGGTTGG
TCAGTGCTGGAATCAGGAAAGTACTA

36 Helper Rev; HIV          TTTTTAGATGGAATAGATAAGGCCCAAGAAGAACATGA
   Integrase; Integration   GAAATATCACAGTAATTGGAGAGCAATGGCTAGTGATT
   of viral RNA             TTAACCTACCACCTGTAGTAGCAAAAGAAATAGTAGCC
                            AGCTGTGATAAATGTCAGCTAAAAGGGGAAGCCATGC
                            ATGGACAAGTAGACTGTAGCCCAGGAATATGGCAGCTA
                            GATTGTACACATTTAGAAGGAAAAGTTATCTTGGTAGC
                            AGTTCATGTAGCCAGTGGATATATAGAAGCAGAAGTAA
                            TTCCAGCAGAGACAGGGCAAGAAACAGCATACTTCCTC
                            TTAAAATTAGCAGGAAGATGGCCAGTAAAAACAGTAC
                            ATACAGACAATGGCAGCAATTTCACCAGTACTACAGTT
                            AAGGCCGCCTGTTGGTGGGCGGGGATCAAGCAGGAATT
                            TGGCATTCCCTACAATCCCCAAAGTCAAGGAGTAATAG
                            AATCTATGAATAAAGAATTAAAGAAAATTATAGGACA
                            GGTAAGAGATCAGGCTGAACATCTTAAGACAGCAGTAC
                            AAATGGCAGTATTCATCCACAATTTTAAAAGAAAAGGG
                            GGGATTGGGGGGTACAGTGCAGGGGAAAGAATAGTAG
                            ACATAATAGCAACAGACATACAAACTAAAGAATTACA
                            AAAACAAATTACAAAAATTCAAAATTTTCGGGTTTATT
                            ACAGGGACAGCAGAGATCCAGTTTGGAAAGGACCAGC
                            AAAGCTCCTCTGGAAAGGTGAAGGGGCAGTAGTAATA
                            CAAGATAATAGTGACATAAAAGTAGTGCCAAGAAGAA
                            AAGCAAAGATCATCAGGGATTATGGAAAACAGATGGC
                            AGGTGATGATTGTGTGGCAAGTAGACAGGATGAGGATT
                            AA 37 Helper/Rev; HIV Rev;     ATGGCAGGAAGAAGCGGAGACAGCGACGAAGAACTCC
   Nuclear export and       TCAAGGCAGTCAGACTCATCAAGTTTCTCTATCAAAGC
   stabilize viral mRNA     AACCCACCTCCCAATCCCGAGGGGACCCGACAGGCCCG
                            AAGGAATAGAAGAAGAAGGTGGAGAGAGAGACAGAG
                            ACAGATCCATTCGATTAGTGAACGGATCCTTAGCACTT
                            ATCTGGGACGATCTGCGGAGCCTGTGCCTCTTCAGCTA
                            CCACCGCTTGAGAGACTTACTCTTGATTGTAACGAGGA -continued

| | | Sequences |
|---|---|---|

| SEQ ID NO: | Description | Sequence |
|---|---|---|
| | | TTGTGGAACTTCTGGGACGCAGGGGGTGGGAAGCCCTC AAATATTGGTGGAATCTCCTACAATATTGGAGTCAGGA GCTAAAGAATAG |
| 38 | Helper/Rev; Rabbit beta globin poly A; RNA stability | AGATCTTTTTCCCTCTGCCAAAAATTATGGGGACATCAT GAAGCCCCTTGAGCATCTGACTTCTGGCTAATAAAGGA AATTTATTTTCATTGCAATAGTGTGTTGGAATTTTTTGT GTCTCTCACTCGGAAGGACATATGGGAGGGCAAATCAT TTAAAACATCAGAATGAGTATTTGGTTTAGAGTTTGGC AACATATGCCATATGCTGGCTGCCATGAACAAAGGTGG CTATAAAGAGGTCATCAGTATATGAAACAGCCCCCTGC TGTCCATTCCTTATTCCATAGAAAAGCCTTGACTTGAGG TTAGATTTTTTTTATATTTTGTTTTGTGTTATTTTTTTCTT TAACATCCCTAAAATTTTCCTTACATGTTTTACTAGCCA GATTTTTCCTCCTCTCCTGACTACTCCCAGTCATAGCTG TCCCTCTTCTCTTATGAAGATC |
| 39 | Envelope; CMV promoter; Transcription | ACATTGATTATTGACTAGTTATTAATAGTAATCAATTAC GGGGTCATTAGTTCATAGCCCATATATGGAGTTCCGCG TTACATAACTTACGGTAAATGGCCCGCCTGGCTGACCG CCCAACGACCCCCGCCCATTGACGTCAATAATGACGTA TGTTCCCATAGTAACGCCAATAGGGACTTTCCATTGAC GTCAATGGGTGGAGTATTTACGGTAAACTGCCCACTTG GCAGTACATCAAGTGTATCATATGCCAAGTACGCCCCC TATTGACGTCAATGACGGTAAATGGCCCGCCTGGCATT ATGCCCAGTACATGACCTTATGGGACTTTCCTACTTGGC AGTACATCTACGTATTAGTCATCGCTATTACCATGGTGA TGCGGTTTTGGCAGTACATCAATGGGCGTGGATAGCGG TTTGACTCACGGGGATTTCCAAGTCTCCACCCCATTGAC GTCAATGGGAGTTTGTTTTGGCACCAAAATCAACGGGA CTTTCCAAAATGTCGTAACAACTCCGCCCCATTGACGC AAATGGGCGGTAGGCGTGTACGGTGGGAGGTCTATATA AGC |
| 40 | Envelope; Beta globin intron; Enhance gene expression | GTGAGTTTGGGGACCCTTGATTGTTCTTTCTTTTTCGCT ATTGTAAAATTCATGTTATATGGAGGGGGCAAAGTTTT CAGGGTGTTGTTTAGAATGGGAAGATGTCCCTTGTATC ACCATGGACCCTCATGATAATTTTGTTTCTTTCACTTTC TACTCTGTTGACAACCATTGTCTCCTCTTATTTTCTTTTC ATTTTCTGTAACTTTTTCGTTAAACTTTAGCTTGCATTTG TAACGAATTTTTAAATTCACTTTTGTTTATTTGTCAGAT TGTAAGTACTTTCTCTAATCACTTTTTTTTCAAGGCAAT CAGGGTATATTATATTGTACTTCAGCACAGTTTTAGAG AACAATTGTTATAATTAAATGATAAGGTAGAATATTTC TGCATATAAATTCTGGCTGGCGTGGAAATATTCTTATTG GTAGAAACAACTACACCCTGGTCATCATCCTGCCTTTCT CTTTATGGTTACAATGATATACACTGTTTGAGATGAGG ATAAAATACTCTGAGTCCAAACCGGGCCCCTCTGCTAA CCATGTTCATGCCTTCTTCTCTTTCCTACAG |
| 41 | Primer | TAAGCAGAATTCATGAATTTGCCAGGAAGAT |
| 42 | Primer | CCATACAATGAATGGACACTAGGCGGCCGCACGAAT |
| 43 | Gag, Pol, Integrase fragment | GAATTCATGAATTTGCCAGGAAGATGGAAACCAAAAAT GATAGGGGGAATTGGAGGTTTTATCAAAGTAAGACAGT ATGATCAGATACTCATAGAAATCTGCGGACATAAAGCT ATAGGTACAGTATTAGTAGGACCTACACCTGTCAACAT AATTGGAAGAAATCTGTTGACTCAGATTGGCTGCACTT TAAATTTTCCCATTAGTCCTATTGAGACTGTACCAGTAA AATTAAAGCCAGGAATGGATGGCCCAAAAGTTAAACA ATGGCCATTGACAGAAGAAAAAATAAAAGCATTAGTA GAAATTTGTACAGAAATGGAAAAGGAAGGAAAAATTT CAAAAATTGGGCCTGAAAATCCATACAATACTCCAGTA TTTGCCATAAAGAAAAAAGACAGTACTAAATGGAGAA AATTAGTAGATTTCAGAGAACTTAATAAGAGAACTCAA GATTTCTGGGAAGTTCAATTAGGAATACCACATCCTGC AGGGTTAAAACAGAAAAAATCAGTAACAGTACTGGAT GTGGGCGATGCATATTTTTCAGTTCCCTTAGATAAAGA CTTCAGGAAGTATACTGCATTTACCATACCTAGTATAA ACAATGAGACACCAGGGATTAGATATCAGTACAATGTG CTTCCACAGGGATGGAAAGGATCACCAGCAATATTCCA GTGTAGCATGACAAAAATCTTAGAGCCTTTTAGAAAAC |

| | | Sequences |
|---|---|---|

| SEQ ID NO: | Description | Sequence |
|---|---|---|
| | | AAAATCCAGACATAGTCATCTATCAATACATGGATGAT |
| | | TTGTATGTAGGATCTGACTTAGAAATAGGGCAGCATAG |
| | | AACAAAAATAGAGGAACTGAGACAACATCTGTTGAGG |
| | | TGGGGATTTACCACACCAGACAAAAAACATCAGAAAG |
| | | AACCTCCATTCCTTTGGATGGGTTATGAACTCCATCCTG |
| | | ATAAATGGACAGTACAGCCTATAGTGCTGCCAGAAAAG |
| | | GACAGCTGGACTGTCAATGACATACAGAAATTAGTGGG |
| | | AAAATTGAATTGGGCAAGTCAGATTTATGCAGGGATTA |
| | | AAGTAAGGCAATTATGTAAACTTCTTAGGGGAACCAAA |
| | | GCACTAACAGAAGTAGTACCACTAACAGAAGAAGCAG |
| | | AGCTAGAACTGGCAGAAAACAGGGAGATTCTAAAAGA |
| | | ACCGGTACATGGAGTGTATTATGACCCATCAAAAGACT |
| | | TAATAGCAGAAATACAGAAGCAGGGGCAAGGCCAATG |
| | | GACATATCAAATTTATCAAGAGCCATTTAAAAATCTGA |
| | | AAACAGGAAAGTATGCAAGAATGAAGGGTGCCCACAC |
| | | TAATGATGTGAAACAATTAACAGAGGCAGTACAAAAA |
| | | ATAGCCACAGAAAGCATAGTAATATGGGGAAAGACTC |
| | | CTAAATTTAAATTACCCATACAAAAGGAAACATGGGAA |
| | | GCATGGTGGACAGAGTATTGGCAAGCCACCTGGATTCC |
| | | TGAGTGGGAGTTTGTCAATACCCCTCCCTTAGTGAAGTT |
| | | ATGGTACCAGTTAGAGAAAGAACCCATAATAGGAGCA |
| | | GAAACTTTCTATGTAGATGGGGCAGCCAATAGGGAAAC |
| | | TAAATTAGGAAAAGCAGGATATGTAACTGACAGAGGA |
| | | AGACAAAAAGTTGTCCCCCTAACGGACACAACAAATCA |
| | | GAAGACTGAGTTACAAGCAATTCATCTAGCTTTGCAGG |
| | | ATTCGGGATTAGAAGTAAACATAGTGACAGACTCACAA |
| | | TATGCATTGGGAATCATTCAAGCACAACCAGATAAGAG |
| | | TGAATCAGAGTTAGTCAGTCAAATAATAGAGCAGTTAA |
| | | TAAAAAAGGAAAAAGTCTACCTGGCATGGGTACCAGC |
| | | ACACAAAGGAATTGGAGGAAATGAACAAGTAGATAAA |
| | | TTGGTCAGTGCTGGAATCAGGAAAGTACTATTTTTAGA |
| | | TGGAATAGATAAGGCCCAAGAAGAACATGAGAAATAT |
| | | CACAGTAATTGGAGAGCAATGGCTAGTGATTTTAACCT |
| | | ACCACCTGTAGTAGCAAAAGAAATAGTAGCCAGCTGTG |
| | | ATAAATGTCAGCTAAAAGGGGAAGCCATGCATGGACA |
| | | AGTAGACTGTAGCCCAGGAATATGGCAGCTAGATTGTA |
| | | CACATTTAGAAGGAAAAGTTATCTTGGTAGCAGTTCAT |
| | | GTAGCCAGTGGATATATAGAAGCAGAAGTAATTCCAGC |
| | | AGAGACAGGGCAAGAAACAGCATACTTCCTCTTAAAAT |
| | | TAGCAGGAAGATGGCCAGTAAAAACAGTACATACAGA |
| | | CAATGGCAGCAATTTCACCAGTACTACAGTTAAGGCCG |
| | | CCTGTTGGTGGGCGGGGATCAAGCAGGAATTTGGCATT |
| | | CCCTACAATCCCCAAAGTCAAGGAGTAATAGAATCTAT |
| | | GAATAAAGAATTAAAGAAAATTATAGGACAGGTAAGA |
| | | GATCAGGCTGAACATCTTAAGACAGCAGTACAAATGGC |
| | | AGTATTCATCCACAATTTTAAAAGAAAAGGGGGGATTG |
| | | GGGGGTACAGTGCAGGGGAAAGAATAGTAGACATAAT |
| | | AGCAACAGACATACAAACTAAAGAATTACAAAAACAA |
| | | ATTACAAAAATTCAAAATTTTCGGGTTTATTACAGGGA |
| | | CAGCAGAGATCCAGTTTGGAAAGGACCAGCAAAGCTC |
| | | CTCTGGAAAGGTGAAGGGGCAGTAGTAATACAAGATA |
| | | ATAGTGACATAAAAGTAGTGCCAAGAAGAAAAGCAAA |
| | | GATCATCAGGGATTATGGAAAACAGATGGCAGGTGAT |
| | | GATTGTGTGGCAAGTAGACAGGATGAGGATTAA |
| 44 | DNA Fragment containing Rev, RRE and rabbit beta globin poly A | TCTAGAATGGCAGGAAGAAGCGGAGACAGCGACGAAG |
| | | AGCTCATCAGAACAGTCAGACTCATCAAGCTTCTCTAT |
| | | CAAAGCAACCCACCTCCCAATCCCGAGGGGACCCGACA |
| | | GGCCCGAAGGAATAGAAGAAGAAGGTGGAGAGAGAG |
| | | ACAGAGACAGATCCATTCGATTAGTGAACGGATCCTTG |
| | | GCACTTATCTGGGACGATCTGCGGAGCCTGTGCCTCTTC |
| | | AGCTACCACCGCTTGAGAGACTTACTCTTGATTGTAAC |
| | | GAGGATTGTGGAACTTCTGGGACGCAGGGGGTGGGAA |
| | | GCCCTCAAATATTGGTGGAATCTCCTACAATATTGGAG |
| | | TCAGGAGCTAAAGAATAGAGGAGCTTTGTTCCTTGGGT |
| | | TCTTGGGAGCAGCAGGAAGCACTATGGGCGCAGCGTCA |
| | | ATGACGCTGACGGTACAGGCCAGACAATTATTGTCTGG |
| | | TATAGTGCAGCAGCAGAACAATTTGCTGAGGGCTATTG |
| | | AGGCGCAACAGCATCTGTTGCAACTCACAGTCTGGGGC |
| | | ATCAAGCAGCTCCAGGCAAGAATCCTGGCTGTGGAAAG |
| | | ATACCTAAAGGATCAACAGCTCCTAGATCTTTTTCCCTC |
| | | TGCCAAAAATTATGGGGACATCATGAAGCCCCTTGAGC |
| | | ATCTGACTTCTGGCTAATAAAGGAAATTTATTTTCATTG |

-continued

| Sequences |
| --- |

SEQ
ID
NO: Description Sequence

CAATAGTGTGTTGGAATTTTTTGTGTCTCTCACTCGGAA
GGACATATGGGAGGGCAAATCATTTAAAACATCAGAAT
GAGTATTTGGTTTAGAGTTTGGCAACATATGCCATATG
CTGGCTGCCATGAACAAAGGTGGCTATAAAGAGGTCAT
CAGTATATGAAACAGCCCCCTGCTGTCCATTCCTTATTC
CATAGAAAAGCCTTGACTTGAGGTTAGATTTTTTTTATA
TTTTGTTTTGTGTTATTTTTTTCTTTAACATCCCTAAAAT
TTTCCTTACATGTTTTACTAGCCAGATTTTTCCTCCTCTC
CTGACTACTCCCAGTCATAGCTGTCCCTCTTCTCTTATG
AAGATCCCTCGACCTGCAGCCCAAGCTTGGCGTAATCA
TGGTCATAGCTGTTTCCTGTGTGAAATTGTTATCCGCTC
ACAATTCCACACAACATACGAGCCGGAAGCATAAAGT
GTAAAGCCTGGGGTGCCTAATGAGTGAGCTAACTCACA
TTAATTGCGTTGCGCTCACTGCCCGCTTTCCAGTCGGGA
AACCTGTCGTGCCAGCGGATCCGCATCTCAATTAGTCA
GCAACCATAGTCCCGCCCCTAACTCCGCCCATCCCGCC
CCTAACTCCGCCCAGTTCCGCCCATTCTCCGCCCCATGG
CTGACTAATTTTTTTTATTTATGCAGAGGCCGAGGCCGC
CTCGGCCTCTGAGCTATTCCAGAAGTAGTGAGGAGGCT
TTTTTGGAGGCCTAGGCTTTTGCAAAAAGCTAACTTGTT
TATTGCAGCTTATAATGGTTACAAATAAAGCAATAGCA
TCACAAATTTCACAAATAAAGCATTTTTTTCACTGCATT
CTAGTTGTGGTTTGTCCAAACTCATCAATGTATCTTATC
AGCGGCCGCCCCGGG

45  DNA fragment            ACGCGTTAGTTATTAATAGTAATCAATTACGGGGTCAT
    containing the CAG       TAGTTCATAGCCCATATATGGAGTTCCGCGTTACATAA
    enhancer/promoter/int    CTTACGGTAAATGGCCCGCCTGGCTGACCGCCCAACGA
    ron sequence             CCCCCGCCCATTGACGTCAATAATGACGTATGTTCCCAT
                             AGTAACGCCAATAGGGACTTTCCATTGACGTCAATGGG
                             TGGACTATTTACGGTAAACTGCCCACTTGGCAGTACAT
                             CAAGTGTATCATATGCCAAGTACGCCCCCTATTGACGT
                             CAATGACGGTAAATGGCCCGCCTGGCATTATGCCCAGT
                             ACATGACCTTATGGGACTTTCCTACTTGGCAGTACATCT
                             ACGTATTAGTCATCGCTATTACCATGGGTCGAGGTGAG
                             CCCCACGTTCTGCTTCACTCTCCCCATCTCCCCCCCCTC
                             CCCACCCCCAATTTTGTATTTATTTATTTTTTAATTATTT
                             TGTGCAGCGATGGGGGCGGGGGGGGGGGGGGCGCGCG
                             CCAGGCGGGGCGGGGCGGGGCGAGGGGCGGGGCGGGG
                             CGAGGCGGAGAGGTGCGGCGGCAGCCAATCAGAGCGG
                             CGCGCTCCGAAAGTTTCCTTTTATGGCGAGGCGGCGGC
                             GGCGGCGGCCCTATAAAAAGCGAAGCGCGCGGCGGGC
                             GGGGAGTCGCTGCGTTGCCTTCGCCCCGTGCCCCGCTCC
                             GCGCCGCCTCGCGCCGCCCGCCCCGGCTCTGACTGACC
                             GCGTTACTCCCACAGGTGAGCGGGCGGGACGGCCCTTC
                             TCCTCCGGGCTGTAATTAGCGCTTGGTTTAATGACGGCT
                             CGTTTCTTTTCTGTGGCTGCGTGAAAGCCTTAAAGGGCT
                             CCGGGAGGGCCCTTTGTGCGGGGGGGAGCGGCTCGGG
                             GGGTGCGTGCGTGTGTGTGTGCGTGGGGAGCGCCGCGT
                             GCGGCCCGCGCTGCCCGGCGGCTGTGAGCGCTGCGGGC
                             GCGGCGCGGGGCTTTGTGCGCTCCGCGTGTGCGCGAGG
                             GGAGCGCGGCCGGGGGCGGTGCCCCGCGGTGCGGGGG
                             GGCTGCGAGGGGAACAAAGGCTGCGTGCGGGGTGTGT
                             GCGTGGGGGGGTGAGCAGGGGGTGTGGGCGCGGCGGT
                             CGGGCTGTAACCCCCCCCTGCACCCCCCTCCCCGAGTT
                             GCTGAGCACGGCCCGGCTTCGGGTGCGGGGCTCCGTGC
                             GGGGCGTGGCGCGGGGCTCGCCGTGCCGGGCGGGGGG
                             TGGCGGCAGGTGGGGGTGCCGGGCGGGGCGGGGCCGC
                             CTCGGGCCGGGGAGGGCTCGGGGGAGGGGCGCGGCGG
                             CCCCGGAGCGCCGGCGGCTGTCGAGGCGCGGCGAGCC
                             GCAGCCATTGCCTTTTATGGTAATCGTGCGAGAGGGCG
                             CAGGGACTTCCTTTGTCCCAAATCTGGCGGAGCCGAAA
                             TCTGGGAGGCGCCGCCGCACCCCCTCTAGCGGGCGCGG
                             GCGAAGCGGTGCGGCGCCGGCAGGAAGGAAATGGGCG
                             GGGAGGGCCTTCGTGCGTCGCCGCGCCGCCGTCCCCTT
                             CTCCATCTCCAGCCTCGGGGCTGCCGCAGGGGGACGGC
                             TGCCTTCGGGGGGGACGGGGCAGGGCGGGGTTCGGCTT
                             CTGGCGTGTGACCGGCGGGAATTC 46  DNA fragment            GAATTCATGAAGTGCCTTTTGTACTTAGCCTTTTTATTC
    containing VSV-G         ATTGGGGTGAATTGCAAGTTCACCATAGTTTTTCCACAC
                             AACCAAAAAGGAAACTGGAAAAATGTTCCTTCTAATTA
                             CCATTATTGCCCGTCAAGCTCAGATTTAAATTGGCATA

| | | Sequences |
|---|---|---|

| SEQ ID NO: | Description | Sequence |
|---|---|---|
| | | ATGACTTAATAGGCACAGCCTTACAAGTCAAAATGCCC AAGAGTCACAAGGCTATTCAAGCAGACGGTTGGATGTG TCATGCTTCCAAATGGGTCACTACTTGTGATTTCCGCTG GTATGGACCGAAGTATATAACACATTCCATCCGATCCT TCACTCCATCTGTAGAACAATGCAAGGAAAGCATTGAA CAAACGAAACAAGGAACTTGGCTGAATCCAGGCTTCCC TCCTCAAAGTTGTGGATATGCAACTGTGACGGATGCCG AAGCAGTGATTGTCCAGGTGACTCCTCACCATGTGCTG GTTGATGAATACACAGGAGAATGGGTTGATTCACAGTT CATCAACGGAAATGCAGCAATTACATATGCCCCACTG TCCATAACTCTACAACCTGGCATTCTGACTATAAGGTC AAAGGGCTATGTGATTCTAACCTCATTTCCATGGACAT CACCTTCTTCTCAGAGGACGGAGAGCTATCATCCCTGG GAAAGGAGGGCACAGGGTTCAGAAGTAACTACTTTGCT TATGAAACTGGAGGCAAGGCCTGCAAAATGCAATACTG CAAGCATTGGGGAGTCAGACTCCCATCAGGTGTCTGGT TCGAGATGGCTGATAAGGATCTCTTTGCTGCAGCCAGA TTCCCTGAATGCCCAGAAGGGTCAAGTATCTCTGCTCC ATCTCAGACCTCAGTGGATGTAAGTCTAATTCAGGACG TTGAGAGGATCTTGGATTATTCCCTCTGCCAAGAAACC TGGAGCAAAATCAGAGCGGGTCTTCCAATCTCTCCAGT GGATCTCAGCTATCTTGCTCCTAAAAACCCAGGAACCG GTCCTGCTTTCACCATAATCAATGGTACCCTAAAATACT TTGAGACCAGATACATCAGAGTCGATATTGCTGCTCCA ATCCTCTCAAGAATGGTCGGAATGATCAGTGGAACTAC CACAGAAAGGGAACTGTGGGATGACTGGGCACCATAT GAAGACGTGGAAATTGGACCCAATGGAGTTCTGAGGA CCAGTTCAGGATATAAGTTTCCTTTATACATGATTGGAC ATGGTATGTTGGACTCCGATCTTCATCTTAGCTCAAAGG CTCAGGTGTTCGAACATCCTCACATTCAAGACGCTGCTT CGCAACTTCCTGATGATGAGAGTTTATTTTTTGGTGATA CTGGGCTATCCAAAAATCCAATCGAGCTTGTAGAAGGT TGGTTCAGTAGTTGGAAAAGCTCTATTGCCTCTTTTTTC TTTATCATAGGGTTAATCATTGGACTATTCTTGGTTCTC CGAGTTGGTATCCATCTTTGCATTAAATTAAAGCACAC CAAGAAAAGACAGATTTATACAGACATAGAGATGAGA ATTC |
| 47 | Rev; RSV promoter; Transcription | ATGGCAGGAAGAAGCGGAGACAGCGACGAAGAACTCC TCAAGGCAGTCAGACTCATCAAGTTTCTCTATCAAAGC AACCCACCTCCCAATCCCGAGGGGACCCGACAGGCCCG AAGGAATAGAAGAAGAAGGTGGAGAGAGAGACAGAG ACAGATCCATTCGATTAGTGAACGGATCCTTAGCACTT ATCTGGGACGATCTGCGGAGCCTGTGCCTCTTCAGCTA CCACCGCTTGAGAGACTTACTCTTGATTGTAACGAGGA TTGTGGAACTTCTGGGACGCAGGGGGTGGGAAGCCCTC AAATATTGGTGGAATCTCCTACAATATTGGAGTCAGGA GCTAAAGAATAG |
| 48 | RSV promoter and HIV Rev | CAATTGCGATGTACGGGCCAGATATACGCGTATCTGAG GGGACTAGGGTGTGTTTAGGCGAAAAGCGGGGCTTCGG TTGTACGCGGTTAGGAGTCCCCTCAGGATATAGTAGTT TCGCTTTTGCATAGGGAGGGGGAAATGTAGTCTTATGC AATACACTTGTAGTCTTGCAACATGGTAACGATGAGTT AGCAACATGCCTTACAAGGAGAGAAAAAGCACCGTGC ATGCCGATTGGTGGAAGTAAGGTGGTACGATCGTGCCT TATTAGGAAGGCAACAGACAGGTCTGACATGGATTGGA CGAACCACTGAATTCCGCATTGCAGAGATAATTGTATT TAAGTGCCTAGCTCGATACAATAAACGCCATTTGACCA TTCACCACATTGGTGTGCACCTCCAAGCTCGAGCTCGTT TAGTGAACCGTCAGATCGCCTGGAGACGCCATCCACGC TGTTTTGACCTCCATAGAAGACACCGGGACCGATCCAG CCTCCCCTCGAAGCTAGCGATTAGGCATCTCCTATGGC AGGAAGAAGCGGAGACAGCGACGAAGAACTCCTCAAG GCAGTCAGACTCATCAAGTTTCTCTATCAAAGCAACCC ACCTCCCAATCCCGAGGGGACCCGACAGGCCCGAAGG AATAGAAGAAGAAGGTGGAGAGAGAGACAGAGACAG ATCCATTCGATTAGTGAACGGATCCTTAGCACTTATCTG GGACGATCTGCGGAGCCTGTGCCTCTTCAGCTACCACC GCTTGAGAGACTTACTCTTGATTGTAACGAGGATTGTG GAACTTCTGGGACGCAGGGGGTGGGAAGCCCTCAAAT ATTGGTGGAATCTCCTACAATATTGGAGTCAGGAGCTA AAGAATAGTCTAGA |

-continued

| Sequences | | |
| --- | --- | --- |

SEQ
ID
NO: Description          Sequence

49 Promoter; PGK    GGGGTTGGGGTTGCGCCTTTTCCAAGGCAGCCCTGGGT
TTGCGCAGGGACGCGGCTGCTCTGGGCGTGGTTCCGGG
AAACGCAGCGGCGCCGACCCTGGGTCTCGCACATTCTT
CACGTCCGTTCGCAGCGTCACCCGGATCTTCGCCGCTA
CCCTTGTGGGCCCCCCGGCGACGCTTCCTGCTCCGCCCC
TAAGTCGGGAAGGTTCCTTGCGGTTCGCGGCGTGCCGG
ACGTGACAAACGGAAGCCGCACGTCTCACTAGTACCCT
CGCAGACGGACAGCGCCAGGGAGCAATGGCAGCGCGC
CGACCGCGATGGGCTGTGGCCAATAGCGGCTGCTCAGC
AGGGCGCGCCGAGAGCAGCGGCCGGGAAGGGGCGGTG
CGGGAGGCGGGGTGTGGGGCGGTAGTGTGGGCCCTGTT
CCTGCCCGCGCGGTGTTCCGCATTCTGCAAGCCTCCGG
AGCGCACGTCGGCAGTCGGCTCCCTCGTTGACCGAATC
ACCGACCTCTCTCCCCAG 50 Promoter; UbC    GCGCCGGGTTTTGGCGCCTCCCGCGGGCGCCCCCCTCC
TCACGGCGAGCGCTGCCACGTCAGACGAAGGGCGCAG
GAGCGTTCCTGATCCTTCCGCCCGGACGCTCAGGACAG
CGGCCCGCTGCTCATAAGACTCGGCCTTAGAACCCCAG
TATCAGCAGAAGGACATTTTAGGACGGGACTTGGGTGA
CTCTAGGGCACTGGTTTTCTTTCCAGAGAGCGGAACAG
GCGAGGAAAAGTAGTCCCTTCTCGGCGATTCTGCGGAG
GGATCTCCGTGGGGCGGTGAACGCCGATGATTATATAA
GGACGCGCCGGGTGTGGCACAGCTAGTTCCGTCGCAGC
CGGGATTTGGGTCGCGGTTCTTGTTTGTGGATCGCTGTG
ATCGTCACTTGGTGAGTTGCGGGCTGCTGGGCTGGCCG
GGGCTTTCGTGGCCGCCGGGCCGCTCGGTGGGACGGAA
GCGTGTGGAGAGACCGCCAAGGGCTGTAGTCTGGGTCC
GCGAGCAAGGTTGCCCTGAACTGGGGGGTTGGGGGGAG
CGCACAAAATGGCGGCTGTTCCCGAGTCTTGAATGGAA
GACGCTTGTAAGGCGGGCTGTGAGGTCGTTGAAACAAG
GTGGGGGGCATGGTGGGCGGCAAGAACCCAAGGTCTT
GAGGCCTTCGCTAATGCGGGAAAGCTCTTATTCGGGTG
AGATGGGCTGGGGCACCATCTGGGGACCCTGACGTGAA
GTTTGTCACTGACTGGAGAACTCGGGTTTGTCGTCTGGT
TGCGGGGGCGGCAGTTATGCGGTGCCGTTGGGCAGTGC
ACCCGTACCTTTGGGAGCGCGCGCCTCGTCGTGTCGTG
ACGTCACCCGTTCTGTTGGCTTATAATGCAGGGTGGGG
CCACCTGCCGGTAGGTGTGCGGTAGGCTTTTCTCCGTCG
CAGGACGCAGGGTTCGGGCCTAGGGTAGGCTCTCCTGA
ATCGACAGGCGCCGGACCTCTGGTGAGGGGAGGGATA
AGTGAGGCGTCAGTTTCTTTGGTCGGTTTTATGTACCTA
TCTTCTTAAGTAGCTGAAGCTCCGGTTTTGAACTATGCG
CTCGGGGTTGGCGAGTGTGTTTTGTGAAGTTTTTTAGGC
ACCTTTTGAAATGTAATCATTTGGGTCAATATGTAATTT
TCAGTGTTAGACTAGTAAA 51 Poly A; SV40    GTTTATTGCAGCTTATAATGGTTACAAATAAAGCAATA
GCATCACAAATTTCACAAATAAAGCATTTTTTTCACTGC
ATTCTAGTTGTGGTTTGTCCAAACTCATCAATGTATCTT
ATCA 52 Poly A; bGH     GACTGTGCCTTCTAGTTGCCAGCCATCTGTTGTTTGCCC
CTCCCCCGTGCCTTCCTTGACCCTGGAAGGTGCCACTCC
CACTGTCCTTTCCTAATAAAATGAGGAAATTGCATCGC
ATTGTCTGAGTAGGTGTCATTCTATTCTGGGGGGTGGG
GTGGGGCAGGACAGCAAGGGGGAGGATTGGGAAGACA
ATAGCAGGCATGCTGGGGATGCGGTGGGCTCTATGG 53 Envelope; RD114    ATGAAACTCCCAACAGGAATGGTCATTTTATGTAGCCT
AATAATAGTTCGGGCAGGGTTTGACGACCCCCGCAAGG
CTATCGCATTAGTACAAAAACAACATGGTAAACCATGC
GAATGCAGCGGAGGGCAGGTATCCGAGGCCCCACCGA
ACTCCATCCAACAGGTAACTTGCCCAGGCAAGACGGCC
TACTTAATGACCAACCAAAAATGGAAATGCAGAGTCAC
TCCAAAAAATCTCACCCCTAGCGGGGGAGAACTCCAGA
ACTGCCCCTGTAACACTTTCCAGGACTCGATGCACAGT
TCTTGTTATACTGAATACCGGCAATGCAGGGCGAATAA
TAAGACATACTACACGGCCACCTTGCTTAAAATACGGT
CTGGGAGCCTCAACAGAGGTACAGATATTACAAAACCCC
AATCAGCTCCTACAGTCCCCTTGTAGGGGCTCTATAAA
TCAGCCCGTTTGCTGGAGTGCCACAGCCCCCCATCCATA -continued

| Sequences | |
|---|---|

| SEQ ID NO: Description | Sequence |
|---|---|
| | TCTCCGATGGTGGAGGACCCCTCGATACTAAGAGAGTG<br>TGGACAGTCCAAAAAAGGCTAGAACAAATTCATAAGG<br>CTATGCATCCTGAACTTCAATACCACCCCTTAGCCCTGC<br>CCAAAGTCAGAGATGACCTTAGCCTTGATGCACGGACT<br>TTTGATATCCTGAATACCACTTTTAGGTTACTCCAGATG<br>TCCAATTTTAGCCTTGCCCAAGATTGTTGGCTCTGTTTA<br>AAACTAGGTACCCCTACCCCTCTTGCGATACCCACTCCC<br>TCTTTAACCTACTCCCTAGCAGACTCCCTAGCGAATGCC<br>TCCTGTCAGATTATACCTCCCCTCTTGGTTCAACCGATG<br>CAGTTCTCCAACTCGTCCTGTTTATCTTCCCCTTTCATTA<br>ACGATACGGAACAAATAGACTTAGGTGCAGTCACCTTT<br>ACTAACTGCACCTCTGTAGCCAATGTCAGTAGTCCTTTA<br>TGTGCCCTAAACGGGTCAGTCTTCCTCTGTGGAAATAA<br>CATGGCATACACCTATTTACCCCAAAACTGGACAGGAC<br>TTTGCGTCCAAGCCTCCCTCCTCCCCGACATTGACATCA<br>TCCCGGGGGATGAGCCAGTCCCCATTCCTGCCATTGAT<br>CATTATATACATAGACCTAAACGAGCTGTACAGTTCAT<br>CCCTTTACTAGCTGGACTGGGAATCACCGCAGCATTCA<br>CCACCGGAGCTACAGGCCTAGGTGTCTCCGTCACCCAG<br>TATACAAAATTATCCCATCAGTTAATATCTGATGTCCAA<br>GTCTTATCCGGTACCATACAAGATTTACAAGACCAGGT<br>AGACTCGTTAGCTGAAGTAGTTCTCCAAAATAGGAGGG<br>GACTGGACCTACTAACGGCAGAACAAGGAGGAATTTGT<br>TTAGCCTTACAAGAAAAATGCTGTTTTTATGCTAACAA<br>GTCAGGAATTGTGAGAAACAAAATAAGAACCCTACAA<br>GAAGAATTACAAAAACGCAGGGAAAGCCTGGCATCCA<br>ACCCTCTCTGGACCGGGCTGCAGGGCTTTCTTCCGTACC<br>TCCTACCTCTCCTGGGACCCCTACTCACCCTCCTACTCA<br>TACTAACCATTGGGCCATGCGTTTTCAATCGATTGGTCC<br>AATTTGTTAAAGACAGGATCTCAGTGGTCCAGGCTCTG<br>GTTTTGACTCAGCAATATCACCAGCTAAAACCCATAGA<br>GTACGAGCCATGA |
| 54 Envelope; GALV | ATGCTTCTCACCTCAAGCCCGCACCACCTTCGGCACCA<br>GATGAGTCCTGGGAGCTGGAAAAGACTGATCATCCTCT<br>TAAGCTGCGTATTCGGAGACGGCAAAACGAGTCTGCA<br>GAATAAGAACCCCCACCAGCCTGTGACCCTCACCTGGC<br>AGGTACTGTCCCAAACTGGGGACGTTGTCTGGGACAAA<br>AAGGCAGTCCAGCCCCTTTGGACTTGGTGGCCCTCTCT<br>TACACCTGATGTATGTGCCCTGGCGGCCGGTCTTGAGT<br>CCTGGGATATCCCGGGATCCGATGTATCGTCCTCTAAA<br>AGAGTTAGACCTCCTGATTCAGACTATACTGCCGCTTA<br>TAAGCAAATCACCTGGGGAGCCATAGGGTGCAGCTAC<br>CCTCGGGCTAGGACCAGGATGGCAAATTCCCCCTTCTA<br>CGTGTGTCCCCGAGCTGGCCGAACCCATTCAGAAGCTA<br>GGAGGTGTGGGGGGCTAGAATCCCTATACTGTAAAGA<br>ATGGAGTTGTGAGACCACGGGTACCGTTTATTGGCAAC<br>CCAAGTCCTCATGGGACCTCATAACTGTAAAATGGGAC<br>CAAAATGTGAAATGGGAGCAAAAATTTCAAAAGTGTG<br>AACAAACCGGCTGGTGTAACCCCCTCAAGATAGACTTC<br>ACAGAAAAAGGAAAACTCTCCAGAGATTGGATAACGG<br>AAAAAACCTGGGAATTAAGGTTCTATGTATATGGACAC<br>CCAGGCATACAGTTGACTATCCGCTTAGAGGTCACTAA<br>CATGCCGGTTGTGGCAGTGGGCCCAGACCCTGTCCTTG<br>CGGAACAGGGACCTCCTAGCAAGCCCCTCACTCTCCCT<br>CTCTCCCCACGGAAAGCGCCGCCCACCCCTCTACCCCC<br>GGCGGCTAGTGAGCAAACCCCTGCGGTGCATGGAGAA<br>ACTGTTACCCTAAACTCTCCGCCTCCCACCAGTGGCGA<br>CCGACTCTTTGGCCTTGTGCAGGGGGCCTTCCTAACCTT<br>GAATGCTACCAACCCAGGGGCCACTAAGTCTTGCTGGC<br>TCTGTTTGGGCATGAGCCCCCCTTATTATGAAGGGATA<br>GCCTCTTCAGGAGAGGTCGCTTATACCTCCAACCATAC<br>CCGATGCCACTGGGGGGCCCAAGGAAAGCTTACCCTCA<br>CTGAGGTCTCCGGACTCGGGTCATGCATAGGGAAGGTG<br>CCTCTTACCCATCAACATCTTTGCAACCAGACCTTACCC<br>ATCAATTCCTCTAAAAACCATCAGTATCTGCTCCCCTCA<br>AACCATAGCTGGTGGGCCTGCAGCACTGGCCTCACCCC<br>CTGCCTCTCCACCTCAGTTTTTAATCAGTCTAAAGACTT<br>CTGTGTCCAGGTCCAGCTGATCCCCCGCATCTATTACC<br>ATTCTGAAGAAACCTTGTTACAAGCTATGACAAATCA<br>CCCCCCAGGTTTAAAAGAGAGCCTGCCTCACTTACCCT<br>AGCTGTCTTCCTGGGGTTAGGGATTGCGGCAGGTATAG<br>GTACTGGCTCAACCGCCCTAATTAAAGGGCCCATAGAC |

| Sequences |
| --- |

| SEQ ID NO: | Description | Sequence |
| --- | --- | --- |
| | | CTCCAGCAAGGCCTAACCAGCCTCCAAATCGCCATTGA |
| | | CGCTGACCTCCGGGCCCTTCAGGACTCAATCAGCAAGC |
| | | TAGAGGACTCACTGACTTCCCTATCTGAGGTAGTACTC |
| | | CAAAATAGGAGAGGCCTTGACTTACTATTCCTTAAAGA |
| | | AGGAGGCCTCTGCGCGGCCCTAAAAGAAGAGTGCTGTT |
| | | TTTATGTAGACCACTCAGGTGCAGTACGAGACTCCATG |
| | | AAAAAACTTAAAGAAAGACTAGATAAAAGACAGTTAG |
| | | AGCGCCAGAAAAACCAAAACTGGTATGAAGGGTGGTT |
| | | CAATAACTCCCCTTGGTTTACTACCCTACTATCAACCAT |
| | | CGCTGGGCCCCTATTGCTCCTCCTTTTGTTACTCACTCT |
| | | TGGGCCCTGCATCATCAATAAATTAATCCAATTCATCA |
| | | ATGATAGGATAAGTGCAGTCAAAATTTTAGTCCTTAGA |
| | | CAGAAATATCAGACCCTAGATAACGAGGAAAACCTTT |
| | | AA |
| 55 | Envelope; FUG | ATGGTTCCGCAGGTTCTTTTGTTTGTACTCCTTCTGGGT |
| | | TTTTCGTTGTGTTTCGGGAAGTTCCCCATTTACACGATA |
| | | CCAGACGAACTTGGTCCCTGGAGCCCTATTGACATACA |
| | | CCATCTCAGCTGTCCAAATAACCTGGTTGTGGAGGATG |
| | | AAGGATGTACCAACCTGTCCGAGTTCTCCTACATGGAA |
| | | CTCAAAGTGGGATACATCTCAGCCATCAAAGTGAACGG |
| | | GTTCACTTGCACAGGTGTTGTGACAGAGGCAGAGACCT |
| | | ACACCAACTTTGTTGGTTATGTCACAACCACATTCAAG |
| | | AGAAAGCATTTCCGCCCCACCCCAGACGCATGTAGAGC |
| | | CGCGTATAACTGGAAGATGGCCGGTGACCCCAGATATG |
| | | AAGAGTCCCTACACAATCCATACCCCGACTACCACTGG |
| | | CTTCGAACTGTAAGAACCACCAAAGAGTCCCTCATTAT |
| | | CATATCCCCAAGTGTGACAGATTTGGACCCATATGACA |
| | | AATCCCTTCACTCAAGGGTCTTCCCTGGCGGAAAGTGC |
| | | TCAGGAATAACGGTGTCCTCTACCTACTGCTCAACTAA |
| | | CCATGATTACACCATTTGGATGCCCGAGAATCCGAGAC |
| | | CAAGGACACCTTGTGACATTTTTACCAATAGCAGAGGG |
| | | AAGAGAGCATCCAACGGGAACAAGACTTGCGGCTTTG |
| | | TGGATGAAAGAGGCCTGTATAAGTCTCTAAAAGGAGC |
| | | ATGCAGGCTCAAGTTATGTGGAGTTCTTGGACTTAGAC |
| | | TTATGGATGGAACATGGGTCGCGATGCAAACATCAGAT |
| | | GAGACCAAATGGTGCCCTCCAGATCAGTTGGTGAATTT |
| | | GCACGACTTTCGCTCAGACGAGATCGAGCATCTCGTTG |
| | | TGGAGGAGTTAGTTAAGAAAAGAGAGGAATGTCTGGA |
| | | TGCATTAGAGTCCATCATGACCACCAAGTCAGTAAGTT |
| | | TCAGACGTCTCAGTCACCTGAGAAAACTTGTCCCAGGG |
| | | TTTGGAAAAGCATATACCATATTCAACAAAACCTTGAT |
| | | GGAGGCTGATGCTCACTACAAGTCAGTCCGGACCTGGA |
| | | ATGAGATCATCCCCTCAAAAGGGTGTTTGAAAGTTGGA |
| | | GGAAGGTGCCATCCTCATGTGAACGGGGTGTTTTTCAA |
| | | TGGTATAATATTAGGGCCTGACGACCATGTCCTAATCC |
| | | CAGAGATGCAATCATCCCTCCTCCAGCAACATATGGAG |
| | | TTGTTGGAATCTTCAGTTATCCCCCTGATGCACCCCCTG |
| | | GCAGACCCTTCTACAGTTTTCAAAGAAGGTGATGAGGC |
| | | TGAGGATTTTGTTGAAGTTCACCTCCCCGATGTGTACA |
| | | AACAGATCTCAGGGGTTGACCTGGGTCTCCCGAACTGG |
| | | GGAAAGTATGTATTGATGACTGCAGGGGCCATGATTGG |
| | | CCTGGTGTTGATATTTCCCTAATGACATGGTGCAGAG |
| | | TTGGTATCCATCTTTGCATTAAATTAAAGCACACCAAG |
| | | AAAAGACAGATTTATACAGACATAGAGATGAACCGAC |
| | | TTGGAAAGTAA |
| 56 | Envelope; LCMV | ATGGGTCAGATTGTGACAATGTTTGAGGCTCTGCCTCA |
| | | CATCATCGATGAGGTGATCAACATTGTCATTATTGTGC |
| | | TTATCGTGATCACGGGTATCAAGGCTGTCTACAATTTT |
| | | GCCACCTGTGGGATATTCGCATTGATCAGTTTCCTACTT |
| | | CTGGCTGGCAGGTCCTGTGGCATGTACGGTCTTAAGGG |
| | | ACCCGACATTTACAAAGGAGTTTACCAATTTAAGTCAG |
| | | TGGAGTTTGATATGTCACATCTGAACCTGACCATGCCC |
| | | AACGCATGTTCAGCCAACAACTCCCACCATTACATCAG |
| | | TATGGGGACTTCTGGACTAGAATTGACCTTCACCAATG |
| | | ATTCCATCATCAGTCACAACTTTTGCAATCTGACCTCTG |
| | | CCTTCAACAAAAAGACCTTTGACCACACACTCATGAGT |
| | | ATAGTTTCGAGCCTACACCTCAGTATCAGAGGGAACTC |
| | | CAACTATAAGGCAGTATCCTGCGACTTCAACAATGGCA |
| | | TAACCATCCAATACAACTTGACATTCTCAGATCGACAA |
| | | AGTGCTCAGAGCCAGTGTAGAACCTTCAGAGGTAGAGT |
| | | CCTAGATATGTTTAGAACTGCCTTCGGGGGGAAATACA |

-continued

| Sequences |
|---|

| SEQ ID NO: Description | Sequence |
|---|---|
| | TGAGGAGTGGCTGGGGCTGGACAGGCTCAGATGGCAA |
| | GACCACCTGGTGTAGCCAGACGAGTTACCAATACCTGA |
| | TTATACAAAATAGAACCTGGGAAAACCACTGCACATAT |
| | GCAGGTCCTTTTGGGATGTCCAGGATTCTCCTTTCCCAA |
| | GAGAAGACTAAGTTCTTCACTAGGAGACTAGCGGGCA |
| | CATTCACCTGGACTTTGTCAGACTCTTCAGGGGTGGAG |
| | AATCCAGGTGGTTATTGCCTGACCAAATGGATGATTCT |
| | TGCTGCAGAGCTTAAGTGTTTCGGGAACACAGCAGTTG |
| | CGAAATGCAATGTAAATCATGATGCCGAATTCTGTGAC |
| | ATGCTGCGACTAATTGACTACAACAAGGCTGCTTTGAG |
| | TAAGTTCAAAGAGGACGTAGAATCTGCCTTGCACTTAT |
| | TCAAAACAACAGTGAATTCTTTGATTTCAGATCAACTA |
| | CTGATGAGGAACCACTTGAGAGATCTGATGGGGGTGCC |
| | ATATTGCAATTACTCAAAGTTTTGGTACCTAGAACATG |
| | CAAAGACCGGCGAAACTAGTGTCCCCAAGTGCTGGCTT |
| | GTCACCAATGGTTCTTACTTAAATGAGACCCACTTCAG |
| | TGATCAAATCGAACAGGAAGCCGATAACATGATTACA |
| | GAGATGTTGAGGAAGGATTACATAAAGAGGCAGGGGA |
| | GTACCCCCCTAGCATTGATGGACCTTCTGATGTTTTCCA |
| | CATCTGCATATCTAGTCAGCATCTTCCTGCACCTTGTCA |
| | AAATACCAACACACAGGCACATAAAAGGTGGCTCATG |
| | TCCAAAGCCACACCGATTAACCAACAAAGGAATTTGTA |
| | GTTGTGGTGCATTTAAGGTGCCTGGTGTAAAAACCGTC |
| | TGGAAAAGACGCTGA |
| | |
| 57 Envelope; FPV | ATGAACACTCAAATCCTGGTTTTCGCCCTTGTGGCAGT |
| | CATCCCCACAAATGCAGACAAAATTTGTCTTGGACATC |
| | ATGCTGTATCAAATGGCACCAAAGTAAACACACTCACT |
| | GAGAGAGGAGTAGAAGTTGTCAATGCAACGGAAACAG |
| | TGGAGCGGACAAACATCCCCAAAATTTGCTCAAAAGG |
| | GAAAAGAACCACTGATCTTGGCCAATGCGGACTGTTAG |
| | GGACCATTACCGGACCACCTCAATGCGACCAATTTCTA |
| | GAATTTTCAGCTGATCTAATAATCGAGAGACGAGAAGG |
| | AAATGATGTTTGTTACCCGGGGAAGTTTGTTAATGAAG |
| | AGGCATTGCGACAAATCCTCAGAGGATCAGGTGGGATT |
| | GACAAAGAAACAATGGGATTCACATATAGTGGAATAA |
| | GGACCAACGGAACAACTAGTGCATGTAGAAGATCAGG |
| | GTCTTCATTCTATGCAGAAATGGAGTGGCTCCTGTCAA |
| | ATACAGACAATGCTGCTTTCCCACAAATGACAAAATCA |
| | TACAAAAACACAAGGAGAGAATCAGCTCTGATAGTCT |
| | GGGGAATCCACCATTCAGGATCAACCACCGAACAGAC |
| | CAAACTATATGGGAGTGGAAATAAACTGATAACAGTC |
| | GGGAGTTCCAAATATCATCAATCTTTTGTGCCGAGTCC |
| | AGGAACACGACCGCAGATAAATGGCCAGTCCGGACGG |
| | ATTGATTTTCATTGGTTGATCTTGGATCCCAATGATACA |
| | GTTACTTTTAGTTTCAATGGGGCTTTCATAGCTCCAAAT |
| | CGTGCCAGCTTCTTGAGGGGAAAGTCCATGGGGATCCA |
| | GAGCGATGTGCAGGTTGATGCCAATTGCGAAGGGGAA |
| | TGCTACCACAGTGGAGGGACTATAACAAGCAGATTGCC |
| | TTTTCAAAACATCAATAGCAGAGCAGTTGGCAAATGCC |
| | CAAGATATGTAAAACAGGAAAGTTTATTATTGGCAACT |
| | GGGATGAAGAACGTTCCCGAACCTTCCAAAAAAAGGA |
| | AAAAAGAGGCCTGTTTGGCGCTATAGCAGGGTTTATT |
| | GAAAATGGTTGGGAAGGTCTGGTCGACGGGTGGTACG |
| | GTTTCAGGCATCAGAATGCACAAGGAGAAGGAACTGC |
| | AGCAGACTACAAAAGCACCCAATCGGCAATTGATCAG |
| | ATAACCGGAAAGTTAAATAGACTCATTGAGAAAACCA |
| | ACCAGCAATTTGAGCTAATAGATAATGAATTCACTGAG |
| | GTGGAAAAGCAGATTGGCAATTTAATTAACTGGACCAA |
| | AGACTCCATCACAGAAGTATGGTCTTACAATGCTGAAC |
| | TTCTTGTGGCAATGGAAAACCAGCACACTATTGATTTG |
| | GCTGATTCAGAGATGAACAAGCTGTATGAGCGAGTGA |
| | GGAAACAATTAAGGGAAAATGCTGAAGAGGATGGCAC |
| | TGGTTGCTTTGAAATTTTTCATAAATGTGACGATGATTG |
| | TATGGCTAGTATAAGGAACAATACTTATGATCACAGCA |
| | AATACAGAGAAGAAGCGATGCAAAATAGAATACAAAT |
| | TGACCCAGTCAAATTGAGTAGTGGCTACAAAGATGTGA |
| | TACTTTGGTTTAGCTTCGGGGCATCATGCTTTTTGCTTC |
| | TTGCCATTGCAATGGGCCTTGTTTTCATATGTGTGAAGA |
| | ACGGAAACATGCGGTGCACTATTTGTATATAA |

-continued

| Sequences | |
|---|---|

| SEQ ID NO: | Description | Sequence |
|---|---|---|
| 58 | Envelope; RRV | AGTGTAACAGAGCACTTTAATGTGTATAAGGCTACTAG<br>ACCATACCTAGCACATTGCGCCGATTGCGGGGACGGGT<br>ACTTCTGCTATAGCCCAGTTGCTATCGAGGAGATCCGA<br>GATGAGGCGTCTGATGGCATGCTTAAGATCCAAGTCTC<br>CGCCCAAATAGGTCTGGACAAGGCAGGCACCCACGCC<br>CACACGAAGCTCCGATATATGGCTGGTCATGATGTTCA<br>GGAATCTAAGAGAGATTCCTTGAGGGTGTACACGTCCG<br>CAGCGTGCTCCATACATGGGACGATGGGACACTTCATC<br>GTCGCACACTGTCCACCAGGCGACTACCTCAAGGTTTC<br>GTTCGAGGACGCAGATTCGCACGTGAAGGCATGTAAG<br>GTCCAATACAAGCACAATCCATTGCCGGTGGGTAGAGA<br>GAAGTTCGTGGTTAGACCACACTTTGGCGTAGAGCTGC<br>CATGCACCTCATACCAGCTGACAACGGCTCCCACCGAC |
| 59 | Envelope; MLV 10A1 | AGTGTAACAGAGCACTTTAATGTGTATAAGGCTACTAG<br>ACCATACCTAGCACATTGCGCCGATTGCGGGGACGGGT<br>ACTTCTGCTATAGCCCAGTTGCTATCGAGGAGATCCGA<br>GATGAGGCGTCTGATGGCATGCTTAAGATCCAAGTCTC<br>CGCCCAAATAGGTCTGGACAAGGCAGGCACCCACGCC<br>CACACGAAGCTCCGATATATGGCTGGTCATGATGTTCA<br>GGAATCTAAGAGAGATTCCTTGAGGGTGTACACGTCCG<br>CAGCGTGCTCCATACATGGGACGATGGGACACTTCATC<br>GTCGCACACTGTCCACCAGGCGACTACCTCAAGGTTTC<br>GTTCGAGGACGCAGATTCGCACGTGAAGGCATGTAAG<br>GTCCAATACAAGCACAATCCATTGCCGGTGGGTAGAGA<br>GAAGTTCGTGGTTAGACCACACTTTGGCGTAGAGCTGC<br>CATGCACCTCATACCAGCTGACAACGGCTCCCACCGAC<br>GAGGAGATTGACATGCATACACCGCCAGATATACCGG<br>ATCGCACCCTGCTATCACAGACGGCGGGCAACGTCAAA<br>ATAACAGCAGGCGGCAGGACTATCAGGTACAACTGTA<br>CCTGCGGCCGTGACAACGTAGGCACTACCAGTACTGAC<br>AAGACCATCAACACATGCAAGATTGACCAATGCCATGC<br>TGCCGTCACCAGCCATGACAAATGGCAATTTACCTCTC<br>CATTTGTTCCCAGGGCTGATCAGACAGCTAGGAAAGGC<br>AAGGTACACGTTCCGTTCCCTCTGACTAACGTCACCTG<br>CCGAGTGCCGTTGGCTCGAGCGCCGGATGCCACCTATG<br>GTAAGAAGGAGGTGACCCTGAGATTACACCCAGATCA<br>TCCGACGCTCTTCTCCTATAGGAGTTTAGGAGCCGAAC<br>CGCACCCGTACGAGGAATGGGTTGACAAGTTCTCTGAG<br>CGCATCATCCCAGTGACGGAAGAAGGGATTGAGTACC<br>AGTGGGGCAACAACCCGCCGGTCTGCCTGTGGGCGCA<br>ACTGACGACCGAGGGCAAACCCCATGGCTGGCCACAT<br>GAAATCATTCAGTACTATTATGGACTATACCCCGCCGC<br>CACTATTGCCGCAGTATCCGGGGCGAGTCTGATGGCCC<br>TCCTAACTCTGGCGGCCACATGCTGCATGCTGGCCACC<br>GCGAGGAGAAAGTGCCTAACACCGTACGCCCTGACGC<br>CAGGAGCGGTGGTACCGTTGACACTGGGGCTGCTTTGC<br>TGCGCACCGAGGGCGAATGCA |
| 60 | Envelope; Ebola | ATGGGTGTTACAGGAATATTGCAGTTACCTCGTGATCG<br>ATTCAAGAGGACATCATTCTTTCTTTGGGTAATTATCCT<br>TTTCCAAAGAACATTTTCCATCCCACTTGGAGTCATCCA<br>CAATAGCACATTACAGGTTAGTGATGTCGACAAACTGG<br>TTTGCCGTGACAAACTGTCATCCACAAATCAATTGAGA<br>TCAGTTGGACTGAATCTCGAAGGGAATGGAGTGGCAA<br>CTGACGTGCCATCTGCAACTAAAAGATGGGGCTTCAGG<br>TCCGGTGTCCCACCAAAGGTGGTCAATTATGAAGCTGG<br>TGAATGGGCTGAAAACTGCTACAATCTTGAAATCAAAA<br>AACCTGACGGGAGTGAGTGTCTACCAGCAGCGCCAGA<br>CGGGATTCGGGGCTTCCCCCGGTGCCGGTATGTGCACA<br>AAGTATCAGGAACGGGACCGTGTGCCGGAGACTTTGCC<br>TTCCACAAAGAGGGTGCTTTCTTCCTGTATGACCGACTT<br>GCTTCCACAGTTATCTACCGAGGAACGACTTTCGCTGA<br>AGGTGTCGTTGCATTTCTGATACTGCCCCAAGCTAAGA<br>AGGACTTCTTCAGCTCACACCCCTTGAGAGAGCCGGTC<br>AATGCAACGGAGGACCCGTCTAGTGGCTACTATTCTAC<br>CACAATTAGATATCAAGCTACCGGTTTTGGAACCAATG<br>AGACAGAGTATTTGTTCGAGGTTGACAATTTGACCTAC<br>GTCCAACTTGAATCAAGATTCACACCACAGTTTCTGCT<br>CCAGCTGAATGAGACAATATATACAAGTGGGAAAAGG<br>AGCAATACCACGGGAAAACTAATTTGGAAGGTCAACC<br>CCGAAATTGATACAACAATCGGGGAGTGGGCCTTCTGG<br>GAAACTAAAAAAACCTCACTAGAAAAAATTCGCAGTGA |

-continued

| Sequences | |
|---|---|

SEQ
ID
NO: Description                    Sequence

AGAGTTGTCTTTCACAGCTGTATCAAACAGAGCCAAAA
ACATCAGTGGTCAGAGTCCGGCGCGAACTTCTTCCGAC
CCAGGGACCAACACAACAACTGAAGACCACAAAATCA
TGGCTTCAGAAAATTCCTCTGCAATGGTTCAAGTGCAC
AGTCAAGGAAGGGAAGCTGCAGTGTCGCATCTGACAA
CCCTTGCCACAATCTCCACGAGTCCTCAACCCCCCACA
ACCAAACCAGGTCCGGACAACAGCACCCACAATACAC
CCGTGTATAAACTTGACATCTCTGAGGCAACTCAAGTT
GAACAACATCACCGCAGAACAGACAACGACAGCACAG
CCTCCGACACTCCCCCCGCCACGACCGCAGCCGGACCC
CTAAAAGCAGAGAACACCAACACGAGCAAGGGTACCG
ACCTCCTGGACCCCGCCACCACAACAAGTCCCCAAAAC
CACAGCGAGACCGCTGGCAACAACAACACTCATCACC
AAGATACCGGAGAAGAGAGTGCCAGCAGCGGGAAGCT
AGGCTTAATTACCAATACTATTGCTGGAGTCGCAGGAC
TGATCACAGGCGGGAGGAGAGCTCGAAGAGAAGCAAT
TGTCAATGCTCAACCCAAATGCAACCCTAATTTACATT
ACTGGACTACTCAGGATGAAGGTGCTGCAATCGGACTG
GCCTGGATACCATATTTCGGGCCAGCAGCCGAGGGAAT
TTACATAGAGGGGCTGATGCACAATCAAGATGGTTTAA
TCTGTGGGTTGAGACAGCTGGCCAACGAGACGACTCAA
GCTCTTCAACTGTTCCTGAGAGCCACAACCGAGCTACG
CACCTTTTCAATCCTCAACCGTAAGGCAATTGATTTCTT
GCTGCAGCGATGGGGCGGCACATGCCACATTTTGGGAC
CGGACTGCTGTATCGAACCACATGATTGGACCAAGAAC
ATAACAGACAAAATTGATCAGATTATTCATGATTTTGT
TGATAAAACCCTTCCGGACCAGGGGGACAATGACAATT
GGTGGACAGGATGGAGACAATGGATACCGGCAGGTAT
TGGAGTTACAGGCGTTATAATTGCAGTTATCGCTTTATT
CTGTATATGCAAATTTGTCTTTTAG

61 Control shRNA        GCCGCTTTGTAGGATAGAGCTCGAGCTCTATCCTACAA
   sequence          AGCGGCTTTTT

What is claimed is:

1. A method of treating a subject suffering from Parkinson's disease, comprising administering to the subject a lentiviral particle that comprises:

an envelope protein capable of infecting a cell in the subject; and a shRNA having at least 80% sequence identity with SEQ ID NO.: 6 or 7.

2. The method of claim 1, wherein the cell comprises a neuron.

3. The method of claim 2, wherein the neuron comprises a tyrosine hydroxylase (TH+) neuron.

4. The method of claim 1, further comprising a second therapeutic regimen.

5. The method of claim 1, further comprising a second therapeutic regimen comprising ablative surgical intervention, neural stimulation, administration of L-DOPA or administration of a dopamine agonist.

6. The method of claim 1, wherein the envelope protein comprises a neuron-specific sequence.

7. The method of claim 6, wherein the neuron-specific sequence targets the shRNA to a neuron.

8. The method of claim 6, wherein the neuron-specific sequence encodes at least one of vesicular stomatitis virus G glycoprotein (VSV-G), fusion glycoprotein type C (FUG-C), and gp64.

9. A method of decreasing poly(ADP-ribose) polymerase-1 (PARP-1) expression, comprising administering to a subject a lentiviral particle comprising:

An envelope protein capable of infecting a cell in the subject; and

A shRNA having at least 80% sequence identity with SEQ ID NO: 6 or 7.

10. The method of claim 9, wherein the cell comprises a neuron.

11. The method of claim 10, wherein the cell comprises a tyrosine hydroxylase (TH+) neuron.

12. The method of claim 9, further comprising a second therapeutic regimen.

13. The method of claim 9, further comprising a second therapeutic regimen comprising ablative surgical intervention, neural stimulation, administration of L-DOPA or administration of a dopamine agonist.

14. The method of claim 9, wherein the envelope protein comprises a neuron-specific sequence.

15. The method of claim 14, wherein the neuron-specific sequence encodes at least one of vesicular stomatitis virus G glycoprotein (VSV-G), fusion glycoprotein type C (FUG-C), and gp64.

* * * * *